(12) United States Patent
Quaranta et al.

(10) Patent No.: US 10,906,897 B2
(45) Date of Patent: Feb. 2, 2021

(54) MICROBIOCIDAL HETEROBICYCLIC DERIVATIVES

(71) Applicant: Syngenta Participations AG, Basel (CH)

(72) Inventors: Laura Quaranta, Stein (CH); Stephan Trah, Stein (CH); Matthias Weiss, Stein (CH); Farhan Bou Hamdan, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/751,976

(22) PCT Filed: Aug. 8, 2016

(86) PCT No.: PCT/EP2016/068890
§ 371 (c)(1),
(2) Date: Feb. 12, 2018

(87) PCT Pub. No.: WO2017/025510
PCT Pub. Date: Feb. 16, 2017

(65) Prior Publication Data
US 2018/0237434 A1 Aug. 23, 2018

(30) Foreign Application Priority Data

Aug. 12, 2015 (EP) ..................... 15180771

(51) Int. Cl.
*C07D 401/04* (2006.01)
*C07D 471/04* (2006.01)
*A01N 43/56* (2006.01)

(52) U.S. Cl.
CPC ........... *C07D 471/04* (2013.01); *A01N 43/56* (2013.01)

(58) Field of Classification Search
CPC .................................................. C07D 401/04
USPC ....................................................... 546/144
See application file for complete search history.

(56) References Cited

FOREIGN PATENT DOCUMENTS

| EP | 1736471 A1 | 12/2006 |
|---|---|---|
| JP | 62-294679 A | 12/1987 |
| WO | 2007011022 A1 | 1/2007 |
| WO | 2016156085 A1 | 10/2016 |

OTHER PUBLICATIONS

Database Chemcats, [Online] Jan. 1, 2015, XP002753014 retrieved from chemcats Dataqbase accession No. 2137532535; abstract &"Aurora Building blocks", Jan. 1, 2015.
International Search Report of PCT/EP/2016068890 dated Jan. 4, 2017.
Extended European Search Report for EP15180771.6 dated Jan. 29, 2016.

*Primary Examiner* — Patricia L Morris
(74) *Attorney, Agent, or Firm* — Baker & Hostetler LLP; Toni-Junell Herbert

(57) ABSTRACT

Compounds of the formula (I) wherein $Q_1$, $Q_2$, Y—X, $R_1$, $R_2$, $R_3$, $R_4$, $R_b$, $R_c$, $R_d$, $R_5$, $R_6$, $R_7$, Ra, m and n are as defined in claim 1. Furthermore, the present invention relates to agrochemical compositions which comprise compounds of formula (I), to preparation of these compositions, and to the use of the compounds or compositions in agriculture or horticulture for combating, preventing or controlling infestation of plants, harvested food crops, seeds or non-living materials by phytopathogenic microorganisms, in particular fungi.

13 Claims, No Drawings

MICROBIOCIDAL HETEROBICYCLIC DERIVATIVES

RELATED APPLICATION INFORMATION

This application is a 371 of International Application No. PCT/EP2016/068890, filed Aug. 8, 2016, which claims priority to EP Application No. 15180771.6 filed Aug. 12, 2015, the contents of which are incorporated herein by reference herein.

The present invention relates to microbiocidal heterobicyclic derivatives, e.g. as active ingredients, which have microbiocidal activity, in particular fungicidal activity. The invention also relates to preparation of these heterobicyclic derivatives, to intermediates useful in the preparation of these heterobicyclic derivatives, to the preparation of these intermediates, to agrochemical compositions which comprise at least one of the heterobicyclic derivatives, to preparation of these compositions and to the use of the heterobicyclic derivatives or compositions in agriculture or horticulture for controlling or preventing infestation of plants, harvested food crops, seeds or non-living materials by phytopathogenic microorganisms, in particular fungi.

Certain fungicidal heterobicyclic compounds are described in WO05070917.

It has now surprisingly been found that certain novel heterobicyclic derivatives have favourable fungicidal properties.

The present invention therefore provides compounds of formula (I)

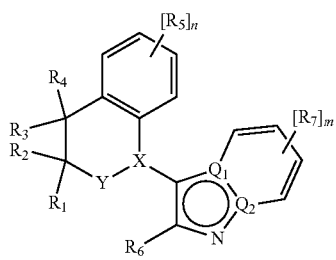

(I)

Wherein $Q_1$ is a nitrogen atom and $Q_2$ is a carbon atom; or
$Q_1$ is a carbon atom and $Q_2$ is a nitrogen atom;
Y—X represents a radical selected from G1, G2, G3 and G4:

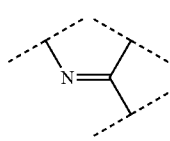

G1

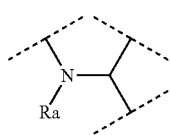

G2

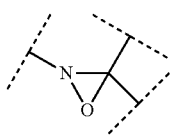

G3

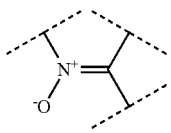

G4

$R_1$ and $R_2$ are each independently selected from hydrogen, cyano, $C_1$-$C_6$ alkyl, $C_3$-$C_7$ cycloalkyl, $C_2$-$C_6$ alkenyl and $C_2$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_1$ and $R_2$ together with the carbon atom to which they are attached represent a $C_3$-$C_{10}$ cycloalkyl group (which may be optionally substituted with 1 to 3 substituents independently selected from the group consisting of halogen, $C_1$-$C_6$ alkyl, $C_1$-$C_6$ alkoxy and $C_1$-$C_6$ alkylthio);

$R_3$ and $R_4$ are each independently selected from hydrogen, halogen, hydroxyl, $C_1$-$C_6$ alkyl, $C_1$-$C_6$ alkoxy, $C_3$-$C_7$ cycloalkyl, $C_2$-$C_6$ alkenyl and $C_2$-$C_6$ alkynyl, in which the alkyl, alkoxy, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_3$ and $R_4$ together with the carbon atom to which they are attached represent C=O, C=NOR$_d$, C=C(R$_b$)(R$_c$) or $C_3$-$C_{10}$ cycloalkyl (which may be optionally substituted with 1 to 3 substituents independently selected from the group consisting of a halogen, $C_1$-$C_6$ alkyl, $C_1$-$C_6$ alkoxy and $C_1$-$C_6$ alkylthio); where R$_b$ and R$_c$ are each independently selected from hydrogen, halogen, cyano, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy and $C_1$-$C_6$ alkylthio, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio, and where R$_d$ is selected from hydrogen, $C_1$-$C_6$ alkyl, $C_3$-$C_7$ cycloalkyl, $C_3$-$C_6$ alkenyl and $C_3$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_2$ and $R_3$ together with the carbon atoms to which they are attached represent a $C_3$-$C_{10}$ cycloalkyl (which may be optionally substituted with 1 to 3 substituents independently selected from the group consisting of halogen, $C_1$-$C_6$ alkyl, $C_1$-$C_6$ alkoxy and $C_1$-$C_6$ alkylthio, and, additionally, a ring carbon unit may be replaced by an oxygen or sulphur atom);

each $R_5$ independently represents halogen, hydroxyl, mercapto, nitro, cyano, formyl, $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(=NOR$_a$) $C_1$-$C_6$alkyl, $C_1$-$C_6$ alkylcarbonyl, aryl, heteroraryl, aryloxy or heteroraryloxy, in which the alkyl, cycloalkyl, alkenyl, alkynyl, alkoxy, alkenyloxy, alkynyloxy, aryl and heteroaryl groups may be optionally substituted with 1 to 5 substituents independently selected from halogen, $C_1$-$C_6$ alkyl, $C_1$-$C_6$ alkoxy, cyano and $C_1$-$C_6$ alkylthio; n is 0, 1, 2, 3 or 4;

$R_6$ is hydrogen, halogen, $C_1$-$C_6$ alkyl, $C_1$-$C_6$ alkoxy or hydroxyl;

each $R_7$ independently represents hydroxyl, mercapto, cyano, halogen, $C_1$-$C_6$ alkyl, $C_1$-$C_6$ haloalkyl, $C_2$-$C_6$ alkenyl, $C_2$-$C_6$ alkynyl, $C_2$-$C_6$ haloalkenyl, $C_3$-$C_6$ haloalkynyl, $C_1$-$C_6$ alkylthio, $C_1$-$C_6$ haloalkoxy, $C_1$-$C_6$ haloalkylthio, $C_1$-$C_6$ alkoxycarbonyl, $C_1$-$C_6$ alkylcarbonyl, $C_3$-$C_7$ cycloalkyl, $C_1$-$C_6$ alkoxy, $C_3$-$C_6$ alkenyloxy or $C_3$-$C_6$ alkynyloxy; m is 0, 1, 2, 3 or 4; and $R_a$ is hydrogen, $C_1$-$C_6$ alkylcarbonyl or $C_1$-$C_6$ alkyl, which may be optionally substituted with 1 to 3 substituents independently selected from the group consisting of halogen, $C_1$-$C_6$ alkoxy, $C_1$-$C_6$ alkylthio and phenoxy; or a salt or N-oxide thereof.

In a second aspect the present invention provides an agrochemical composition comprising a compound of formula (I).

Compounds of formula (I) may be used to control phytopathogenic microorganisms. Thus, in order to control a phytopathogen a compound of formula (I), or a composition comprising a compound of formula (I), according to the invention may be applied directly to the phytopathogen, or to the locus of a phytopathogen, in particular to a plant susceptible to attack by phytopathogens.

Thus, in a third aspect the present invention provides the use of a compound of formula (I), or a composition comprising a compound of formula (I), as described herein to control a phytopathogen.

In a further aspect the present invention provides a method of controlling phytopathogens, comprising applying a compound of formula (I), or a composition comprising a compound of formula (I), as described herein to said phytopathogen, or to the locus of said phytopathogen, in particular to a plant susceptible to attack by a phytopathogen.

Compounds of formula (I) are particularly effective in the control of phytopathogenic fungi.

Thus, in a yet further aspect the present invention provides the use of a compound of formula (I), or a composition comprising a compound of formula (I), as described herein to control phytopathogenic fungi.

In a further aspect the present invention provides a method of controlling phytopathogenic fungi, comprising applying a compound of formula (I), or a composition comprising a compound of formula (I), as described herein to said phytopathogenic fungi, or to the locus of said phytopathogenic fungi, in particular to a plant susceptible to attack by phytopathogenic fungi.

Where substituents are indicated as being optionally substituted, this means that they may or may not carry one or more identical or different substituents, e.g. one to three substituents. Normally not more than three such optional substituents are present at the same time. Where a group is indicated as being substituted, e.g. alkyl, this includes those groups that are part of other groups, e.g. the alkyl in alkylthio.

The term "halogen" refers to fluorine, chlorine, bromine or iodine, preferably fluorine, chlorine or bromine.

Alkyl substituents may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, isopropyl, iso-butyl, sec-butyl, tert-butyl or iso-amyl.

Alkenyl substituents (either alone or as part of a larger group, eg. alkenyloxy) can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents (either alone or as part of a larger group, eg. alkynyloxy) can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Haloalkyl groups (either alone or as part of a larger group, eg. haloalkyloxy) may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Haloalkenyl groups (either alone or as part of a larger group, eg. haloalkenyloxy) are alkenyl groups, respectively, which are substituted with one or more of the same or different halogen atoms and are, for example, 2,2-difluoro-vinyl or 1,2-dichloro-2-fluoro-vinyl.

Haloalkynyl groups (either alone or as part of a larger group, eg. haloalkynyloxy) are alkynyl groups, respectively, which are substituted with one or more of the same or different halogen atoms and are, for example, 1-chloro-prop-2-ynyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Cyano means a —CN group.

Amino means an —$NH_2$ group.

Hydroxyl or hydroxy stands for a —OH group.

Aryl groups (either alone or as part of a larger group, such as e.g. aryloxy, aryl-alkyl) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as e.g. heteroaryloxy, heteroaryl-alkyl) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. [1,2,4] triazolyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkyl) are non-aromatic ring structures containing up to 10 atoms including one or more (preferably one, two or three) heteroatoms selected from O, S and N. Examples of monocyclic groups include, oxetanyl, 4,5-dihydro-isoxazolyl, thietanyl, pyrrolidinyl, tetrahydrofuranyl, [1,3]dioxolanyl, piperidinyl, piperazinyl, [1,4]dioxanyl, imidazolidinyl, [1,3,5]oxadiazinanyl, hexahydro-pyrimidinyl, [1,3,5]triazinanyl and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

The presence of one or more possible asymmetric carbon atoms in a compound of formula (I) means that the compounds may occur in optically isomeric forms, i.e. enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred values of Y—X, $R_1$, $R_2$, $R_3$, $R_4$, $R_b$, $R_c$, $R_d$, $R_5$, $R_6$, $R_7$, $R_a$, m, n, $Q_1$ and $Q_2$ are, in any combination thereof, as set out below:

Preferably Y—X represents the radical G1.

Preferably $R_1$ and $R_2$ are each independently selected from hydrogen, $C_1$-$C_6$ alkyl, $C_3$-$C_7$ cycloalkyl, in which the alkyl and cycloalkyl groups may be optionally substituted with 1 to 3 substituents independently selected from halogen, $C_1$-$C_6$ alkoxy and $C_1$-$C_6$ alkylthio; or $R_1$ and $R_2$ together with the carbon atom to which they are attached represent a $C_3$-$C_6$ cycloalkyl group (which may be optionally substituted with 1 to 3 substituents independently selected from the group consisting of halogen, $C_1$-$C_6$ alkyl and $C_1$-$C_6$ alkoxy).

More preferably $R_1$ and $R_2$ are each independently a hydrogen or $C_1$-$C_4$ alkyl group, in which the alkyl group may be optionally substituted with 1 to 3 substituents independently selected from halogen, and $C_1$-$C_6$ alkoxy; or $R^1$ and $R^2$ together with the carbon atom to which they are attached represent a $C_3$-$C_5$ cycloalkyl group.

Even more preferably $R_1$ and $R_2$ are each independently a $C_1$-$C_3$ alkyl; or $R_1$ and $R_2$ together with the carbon atom to which they are attached represent a $C_3$-$C_4$ cycloalkyl group.

Most preferably $R_1$ and $R_2$ are each independently a $C_1$-$C_2$ alkyl group (especially most preferred is when both are methyl).

Preferably $R_3$ and $R_4$ are each independently selected from hydrogen, halogen, hydroxyl, $C_1$-$C_6$ alkyl, $C_1$-$C_6$ alkoxy and $C_3$-$C_7$ cycloalkyl, in which the alkyl, alkoxy and cycloalkyl groups may be optionally substituted with 1 to 3 substituents independently selected from halogen, $C_1$-$C_6$ alkoxy and $C_1$-$C_6$ alkylthio; or $R_3$ and $R_4$ together with the carbon atom to which they are attached represent C=O, C=NOR$_d$, C=C($R_b$)($R_c$) or $C_3$-$C_6$ cycloalkyl (which may be optionally substituted with 1 to 3 substituents independently selected from the group consisting of a halogen, $C_1$-$C_6$ alkyl, $C_1$-$C_6$ alkoxy and $C_1$-$C_6$ alkylthio), where $R_b$ and $R_c$ are each independently selected from hydrogen, halogen, cyano, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy and $C_1$-$C_6$ alkylthio, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio, and where $R_d$ is selected from hydrogen, $C_1$-$C_6$ alkyl, $C_3$-$C_7$ cycloalkyl, $C_3$-$C_6$ alkenyl and $C_3$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_2$ and $R_3$ together with the carbon atoms to which they are attached represent a $C_3$-$C_7$ cycloalkyl (which may be optionally substituted with 1 to 3 substituents independently selected from the group consisting of halogen, $C_1$-$C_6$ alkyl, $C_1$-$C_6$ alkoxy and $C_1$-$C_6$ alkylthio, and, additionally, a ring carbon unit may be replaced by an oxygen or sulphur atom).

More preferably $R_3$ and $R_4$ are each independently selected from hydrogen, halogen, $C_1$-$C_4$ alkyl and $C_3$-$C_4$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio; or $R_3$ and $R_4$ together with the carbon atom to which they are attached represent C=O, C=NOR$_d$, or $C_3$-$C_6$ cycloalkyl (which may be optionally substituted with 1 to 3 substituents independently selected from the group consisting of a halogen, $C_1$-$C_3$ alkyl, $C_1$-$C_3$ alkoxy and $C_1$-$C_3$ alkylthio), where $R_d$ is selected from hydrogen, $C_1$-$C_4$ alkyl and $C_3$-$C_5$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio (preferably $R_d$ is selected from hydrogen and $C_1$-$C_3$ alkyl, in which the alkyl group may be optionally substituted with 1 to 3 halogen atoms (preferably fluoro atoms)).

Even more preferably $R_3$ and $R_4$ are each independently selected from hydrogen, halogen and $C_1$-$C_4$ alkyl; or $R_3$ and $R_4$ together with the carbon atom to which they are attached represent C=O or $C_3$-$C_4$ cycloalkyl.

Most preferably $R_3$ and $R_4$ are each independently selected from hydrogen, fluoro and $C_1$-$C_2$ alkyl (especially most preferred is if both are methyl or both are fluoro); or $R_3$ and $R_4$ together with the carbon atom to which they are attached represent $C_3$-$C_4$ cycloalkyl.

Preferably each $R_5$ independently represents halogen, cyano, $C_1$-$C_6$ alkyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(=NOR$_a$)$C_1$-$C_6$alkyl, phenyl, heteroraryl (wherein heteroaryl is pyridyl, thiophenyl, thiazolyl, imidazolyl or oxazolyl), phenoxy or heteroraryloxy (wherein heteroaryl is pyridyl, thiophenyl, thiazolyl, imidazolyl or oxazolyl), in which the alkyl, cycloalkyl, alkenyl, alkynyl, alkoxy, alkenyloxy, alkynyloxy, phenyl and heteroaryl groups may be optionally substituted with 1 to 5 substituents independently selected from halogen, $C_1$-$C_6$ alkyl, $C_1$-$C_6$ alkoxy, cyano and $C_1$-$C_6$ alkylthio; n is 0, 1, 2, 3 or 4.

More preferably each $R_5$ independently represents halogen, cyano, $C_1$-$C_4$ alkyl, $C_3$-$C_4$ cycloalkyl, $C_1$-$C_3$ alkoxy, $C_3$-$C_6$ alkenyloxy, $C_3$-$C_6$ alkynyloxy, phenyl, heteroraryl (wherein heteroaryl is pyridyl, thiazolyl or oxazolyl), in which the alkyl, cycloalkyl, alkoxy, alkenyloxy, alkynyloxy, phenyl and heteroaryl groups may be optionally substituted with 1 to 3 substituents independently selected from halogen, $C_1$-$C_3$ alkyl and $C_1$-$C_3$ alkoxy; n is 0, 1 or 2.

Even more preferably each $R_5$ independently represents halogen, cyano, $C_1$-$C_3$ alkyl, $C_3$-$C_4$ cycloalkyl; n is 0, 1 or 2.

Most preferably each $R_5$ independently represents fluoro, chloro, bromo, cyano, or $C_1$-$C_2$ alkyl (especially most preferred is fluoro); n is 0, 1 or 2 (preferably 0 or 1).

Preferably $R_6$ is hydrogen, halogen, or $C_1$-$C_2$ alkyl.
More preferably $R_6$ is hydrogen, fluoro, chloro, or methyl.
Most preferably $R_6$ is hydrogen.

Preferably each $R_7$ independently represents cyano, halogen, $C_1$-$C_6$ alkyl, $C_1$-$C_6$ haloalkyl, $C_2$-$C_6$ alkenyl, $C_2$-$C_6$ alkynyl, $C_2$-$C_6$ haloalkenyl, $C_3$-$C_6$ haloalkynyl, $C_1$-$C_6$ alkylthio, $C_1$-$C_6$ haloalkoxy, $C_1$-$C_6$ haloalkylthio, $C_3$-$C_7$ cycloalkyl, $C_1$-$C_6$ alkoxy, $C_3$-$C_6$ alkenyloxy or $C_3$-$C_6$ alkynyloxy; m is 0, 1, 2, 3 or 4.

More preferably each $R_7$ independently represents cyano, halogen, $C_1$-$C_4$ alkyl, $C_1$-$C_4$ haloalkyl, $C_2$-$C_3$ alkynyl, $C_1$-$C_4$ alkylthio or $C_3$-$C_4$ cycloalkyl; m is 0, 1 or 2.

Even more preferably each $R_7$ independently represents cyano, halogen, $C_1$-$C_3$ alkyl, $C_1$-$C_3$ haloalkyl or $C_3$-$C_4$ cycloalkyl; m is 0, 1 or 2.

Most preferably each $R_7$ independently represents fluoro, chloro or $C_1$-$C_3$ alkyl (especially most preferred is fluoro or methyl); m is 1 or 2.

Preferably $R_a$ is hydrogen or $C_1$-$C_2$ alkyl.

The preferences above apply both when $Q_1$ is a nitrogen atom and when $Q_2$ is a carbon atom, and when $Q_1$ is a carbon atom and $Q_2$ is a nitrogen atom.

Preferably $Q_1$ is a carbon atom and $Q_2$ is a nitrogen atom. Embodiments according to the invention are provided as set out below.

Embodiment 1 provides compounds of formula (I), and a salt or N-oxide thereof, as defined above.

Embodiment 2 provides compounds according to embodiment 1 wherein $R_1$ and $R_2$ are each independently selected from hydrogen, $C_1$-$C_6$ alkyl, $C_3$-$C_7$ cycloalkyl, in which the alkyl and cycloalkyl groups may be optionally substituted with 1 to 3 substituents independently selected from halogen, $C_1$-$C_6$ alkoxy and $C_1$-$C_6$ alkylthio; or $R_1$ and $R_2$ together with the carbon atom to which they are attached represent a $C_3$-$C_6$ cycloalkyl group (which may be optionally substituted with 1 to 3 substituents independently selected from the group consisting of halogen, $C_1$-$C_6$ alkyl and $C_1$-$C_6$ alkoxy).

Embodiment 3 provides compounds according to embodiment 1 or 2 wherein $R_3$ and $R_4$ are each independently selected from hydrogen, halogen, hydroxyl, $C_1$-$C_6$ alkyl, $C_1$-$C_6$ alkoxy and $C_3$-$C_7$ cycloalkyl, in which the alkyl, alkoxy and cycloalkyl groups may be optionally substituted with 1 to 3 substituents independently selected from halogen, $C_1$-$C_6$ alkoxy and $C_1$-$C_6$ alkylthio; or $R_3$ and $R_4$ together with the carbon atom to which they are attached represent C=O, C=$NOR_d$, C=C($R_b$)($R_c$) or $C_3$-$C_6$ cycloalkyl (which may be optionally substituted with 1 to 3 substituents independently selected from the group consisting of a halogen, $C_1$-$C_6$ alkyl, $C_1$-$C_6$ alkoxy and $C_1$-$C_6$ alkylthio), where $R_b$ and $R_c$ are each independently selected from hydrogen, halogen, cyano, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy and $C_1$-$C_6$ alkylthio, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio, and where $R_d$ is selected from hydrogen, $C_1$-$C_6$ alkyl, $C_3$-$C_7$ cycloalkyl, $C_3$-$C_6$ alkenyl and $C_3$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_2$ and $R_3$ together with the carbon atoms to which they are attached represent a $C_3$-$C_7$ cycloalkyl (which may be optionally substituted with 1 to 3 substituents independently selected from the group consisting of halogen, $C_1$-$C_6$ alkyl, $C_1$-$C_6$ alkoxy and $C_1$-$C_6$ alkylthio, and, additionally, a ring carbon unit may be replaced by an oxygen or sulphur atom).

Embodiment 4 provides compounds according to any one of embodiments 1, 2 or 3 wherein each $R_5$ independently represents halogen, cyano, $C_1$-$C_6$ alkyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(=$NOR_a$)$C_1$-$C_6$alkyl, phenyl, heteroaryl (wherein heteroaryl is pyridyl, thiophenyl, thiazolyl, imidazolyl or oxazolyl), phenoxy or heteroraryloxy (wherein heteroaryl is pyridyl, thiophenyl, thiazolyl, imidazolyl or oxazolyl), in which the alkyl, cycloalkyl, alkenyl, alkynyl, alkoxy, alkenyloxy, alkynyloxy, phenyl and heteroaryl groups may be optionally substituted with 1 to 5 substituents independently selected from halogen, $C_1$-$C_6$ alkyl, $C_1$-$C_6$ alkoxy, cyano and $C_1$-$C_6$ alkylthio; n is 0, 1, 2, 3 or 4.

Embodiment 5 provides compounds according to any one of embodiments 1, 2, 3 or 4 wherein $R_6$ is hydrogen, halogen, or $C_1$-$C_2$ alkyl.

Embodiment 6 provides compounds according to any one of embodiments 1, 2, 3, 4, or 5 wherein each $R_7$ independently represents cyano, halogen, $C_1$-$C_6$ alkyl, $C_1$-$C_6$ haloalkyl, $C_2$-$C_6$ alkenyl, $C_2$-$C_6$ alkynyl, $C_2$-$C_6$ haloalkenyl, $C_3$-$C_6$ haloalkynyl, $C_1$-$C_6$ alkylthio, $C_1$-$C_6$ haloalkoxy, $C_1$-$C_6$ haloalkylthio, $C_3$-$C_7$ cycloalkyl, $C_1$-$C_6$ alkoxy, $C_3$-$C_6$alkenyloxy or $C_3$-$C_6$ alkynyloxy; m is 0, 1, 2, 3 or 4.

Embodiment 7 provides compounds according to any one of embodiments 1, 2, 3, 4, 5, or 6 wherein $R_1$ and $R_2$ are each independently a hydrogen or $C_1$-$C_4$ alkyl group, in which the alkyl group may be optionally substituted with 1 to 3 substituents independently selected from halogen, and $C_1$-$C_6$ alkoxy; or $R^1$ and $R^2$ together with the carbon atom to which they are attached represent a $C_3$-$C_5$ cycloalkyl group.

Embodiment 8 provides compounds according to any one of embodiments 1, 2, 3, 4, 5, 6, or 7 wherein $R_3$ and $R_4$ are each independently selected from hydrogen, halogen, $C_1$-$C_4$ alkyl and $C_3$-$C_4$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio; or $R_3$ and $R_4$ together with the carbon atom to which they are attached represent C=O, C=$NOR_d$, or $C_3$-$C_6$ cycloalkyl (which may be optionally substituted with 1 to 3 substituents independently selected from the group consisting of a halogen, $C_1$-$C_3$ alkyl, $C_1$-$C_3$ alkoxy and $C_1$-$C_3$ alkylthio), where $R_d$ is selected from hydrogen, $C_1$-$C_4$ alkyl and $C_3$-$C_5$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio (preferably $R_d$ is selected from hydrogen and $C_1$-$C_3$ alkyl, in which the alkyl group may be optionally substituted with 1 to 3 halogen atoms (preferably fluoro atoms)).

Embodiment 9 provides compounds according to any one of embodiments 1, 2, 3, 4, 5, 6, 7, or 8 wherein each $R_5$ independently represents halogen, cyano, $C_1$-$C_4$ alkyl, $C_3$-$C_4$ cycloalkyl, $C_1$-$C_3$ alkoxy, $C_3$-$C_6$ alkenyloxy, $C_3$-$C_6$ alkynyloxy, phenyl, heteroraryl (wherein heteroaryl is pyridyl, thiazolyl or oxazolyl), in which the alkyl, cycloalkyl, alkoxy, alkenyloxy, alkynyloxy, phenyl and heteroaryl groups may be optionally substituted with 1 to 3 substituents independently selected from halogen, $C_1$-$C_3$ alkyl and $C_1$-$C_3$ alkoxy; n is 0, 1 or Embodiment 10 provides compounds according to any one of embodiments 1, 2, 3, 4, 5, 6, 7, 8, or 9 wherein $R_6$ is hydrogen, fluoro, chloro, or methyl.

Embodiment 11 provides compounds according to any one of embodiments 1, 2, 3, 4, 5, 6, 7, 8, 9 or 10 wherein each $R_7$ independently represents cyano, halogen, $C_1$-$C_4$ alkyl, $C_1$-$C_4$ haloalkyl, $C_2$-$C_3$ alkynyl, $C_1$-$C_4$ alkylthio or $C_3$-$C_4$ cycloalkyl; m is 0, 1 or 2.

Embodiment 12 provides compounds according to any one of embodiments 1, 2, 3, 4, 5, 6, 7, 8, 9, 10 or 11 wherein $R_1$ and $R_2$ are each independently a $C_1$-$C_3$ alkyl; or $R_1$ and $R_2$ together with the carbon atom to which they are attached represent a $C_3$-$C_4$ cycloalkyl group.

Embodiment 13 provides compounds according to any one of embodiments 1, 2, 3, 4, 5, 6, 7, 8, 9, 10, 11 or 12 wherein $R_3$ and $R_4$ are each independently selected from hydrogen, halogen and $C_1$-$C_4$ alkyl; or $R_3$ and $R_4$ together with the carbon atom to which they are attached represent C=O or $C_3$-$C_4$ cycloalkyl.

Embodiment 14 provides compounds according to any one of embodiments 1, 2, 3, 4, 5, 6, 7, 8, 9, 10, 11, 12 or 13 wherein each $R_5$ independently represents halogen, cyano, $C_1$-$C_3$ alkyl, $C_3$-$C_4$ cycloalkyl; n is 0, 1 or 2.

Embodiment 15 provides compounds according to any one of embodiments 1, 2, 3, 4, 5, 6, 7, 8, 9, 10, 11, 12, 13 or 14 wherein $R_6$ is hydrogen.

Embodiment 16 provides compounds according to any one of embodiments 1, 2, 3, 4, 5, 6, 7, 8, 9, 10, 11, 12, 13, 14 or 15 wherein each $R_7$ independently represents cyano, halogen, $C_1$-$C_3$ alkyl, $C_1$-$C_3$ haloalkyl or $C_3$-$C_4$ cycloalkyl; m is 0, 1 or 2.

Embodiment 17 provides compounds according to any one of embodiments 1, 2, 3, 4, 5, 6, 7, 8, 9, 10, 11, 12, 13, 14, 15 or 16 wherein $R_1$ and $R_2$ are each independently a $C_1$-$C_2$ alkyl group (preferably both are methyl).

Embodiment 18 provides compounds according to any one of embodiments 1, 2, 3, 4, 5, 6, 7, 8, 9, 10, 11, 12, 13, 14, 15, 16 or 17 wherein $R_3$ and $R_4$ are each independently selected from hydrogen, fluoro and $C_1$-$C_2$ alkyl (preferably both are methyl or both are fluoro); or $R_3$ and $R_4$ together with the carbon atom to which they are attached represent $C_3$-$C_4$ cycloalkyl.

Embodiment 19 provides compounds according to any one of embodiments 1, 2, 3, 4, 5, 6, 7, 8, 9, 10, 11, 12, 13, 14, 15, 16, 17 or 18 wherein each $R_5$ independently represents fluoro, chloro, bromo, cyano, or $C_1$-$C_2$ alkyl (preferably fluoro); n is 0, 1 or 2 (preferably 0 or 1).

Embodiment 20 provides compounds according to any one of embodiments 1, 2, 3, 4, 5, 6, 7, 8, 9, 10, 11, 12, 13, 14, 15, 16, 17, 18 or 19 wherein each $R_7$ independently represents fluoro, chloro or $C_1$-$C_3$ alkyl (preferably fluoro or methyl); m is 1 or 2.

Embodiment 21 provides compounds according to any one of embodiments 1, 2, 3, 4, 5, 6, 7, 8, 9, 10, 11, 12, 13, 14, 15, 16, 17, 18, 19 or 20 wherein Y—X represents the radical G1.

Embodiment 22 provides compounds according to any one of embodiments 1, 2, 3, 4, 5, 6, 7, 8, 9, 10, 11, 12, 13, 14, 15, 16, 17, 18, 19, 20 or 21 wherein $Q_1$ is a nitrogen atom and when $Q_2$ is a carbon atom Embodiment 23 provides compounds according to any one of embodiments 1, 2, 3, 4, 5, 6, 7, 8, 9, 10, 11, 12, 13, 14, 15, 16, 17, 18, 19, 20 or 21 wherein $Q_1$ is a carbon atom and $Q_2$ is a nitrogen atom.

One group of compounds according to the invention are those of formula (I'):

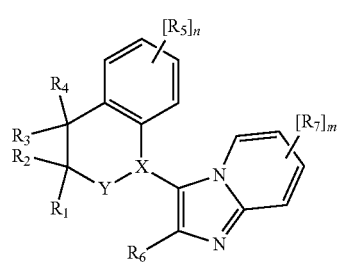

wherein Y—X, $R^1$, $R^2$, $R^3$, $R^4$, $R^5$, $R^6$, $R^7$, m and n are as defined for compounds of formula (I), or a salt or N-oxide thereof. Preferred definitions of Y—X, $R^1$, $R^2$, $R^3$, $R^4$, $R^5$, $R^6$, $R^7$, m and n are as defined for compounds of formula (I).

Another group of compounds according to the invention are those of formula (I''):

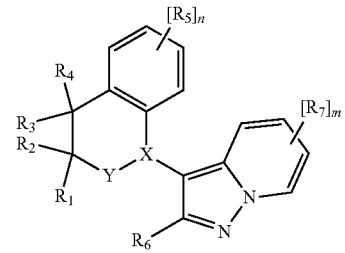

wherein Y—X, $R^1$, $R^2$, $R^3$, $R^4$, $R^5$, $R^6$, $R^7$, m and n are as defined for compounds of formula (I), or a salt or N-oxide thereof. Preferred definitions of Y—X, $R^1$, $R^2$, $R^3$, $R^4$, $R^5$, $R^6$, $R^7$, m and n are as defined for compounds of formula (I).

A preferred group of compounds according to the invention are those of formula (I-1):

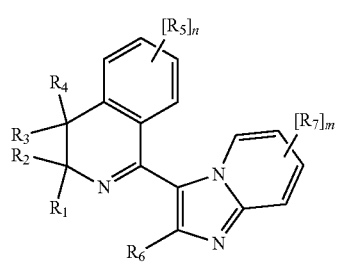

wherein $R^1$, $R^2$, $R^3$, $R^4$, $R^5$, $R^6$, $R^7$, m and n are as defined for compounds of formula (I), or a salt or N-oxide thereof. Preferred definitions of $R^1$, $R^2$, $R^3$, $R^4$, $R^5$, $R^6$, $R^7$, m and n are as defined for compounds of formula (I).

Another preferred group of compounds according to the invention are those of formula (I-2):

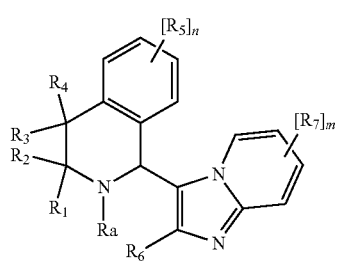

wherein $R^1$, $R^2$, $R^3$, $R^4$, $R^5$, $R^6$, $R^7$, $R_a$, m and n are as defined for compounds of formula (I), or a salt or N-oxide thereof. Preferred definitions of $R^1$, $R^2$, $R^3$, $R^4$, $R^5$, $R^6$, $R^7$, $R_a$, m and n are as defined for compounds of formula (I).

Another preferred group of compounds according to the invention are those of formula (I-3):

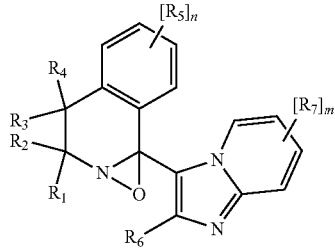

(I-3)

wherein $R^1$, $R^2$, $R^3$, $R^4$, $R^5$, $R^6$, $R^7$, m and n are as defined for compounds of formula (I), or a salt or N-oxide thereof. Preferred definitions of $R^1$, $R^2$, $R^3$, $R^4$, $R^5$, $R^6$, $R^7$, m and n are as defined for compounds of formula (I).

Another preferred group of compounds according to the invention are those of formula (I-4):

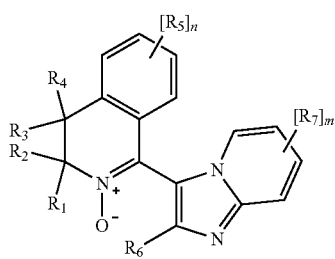

(I-4)

wherein $R^1$, $R^2$, $R^3$, $R^4$, $R^5$, $R^6$, $R^7$, m and n are as defined for compounds of formula (I), or a salt or N-oxide thereof. Preferred definitions of $R^1$, $R^2$, $R^3$, $R^4$, $R^5$, $R^6$, $R^7$, m and n are as defined for compounds of formula (I).

Another preferred group of compounds according to the invention are those of formula (I-5):

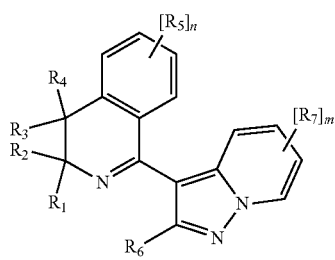

(I-5)

wherein $R^1$, $R^2$, $R^3$, $R^4$, $R^5$, $R^6$, $R^7$, m and n are as defined for compounds of formula (I), or a salt or N-oxide thereof. Preferred definitions of $R^1$, $R^2$, $R^3$, $R^4$, $R^5$, $R^6$, $R^7$, m and n are as defined for compounds of formula (I).

Another preferred group of compounds according to the invention are those of formula (I-6):

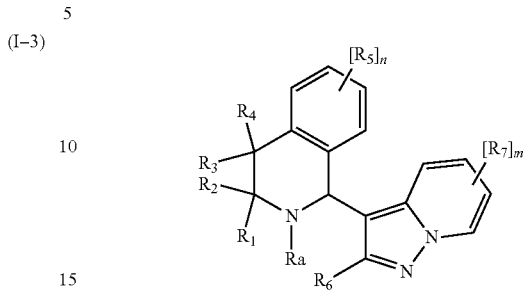

(I-6)

wherein $R^1$, $R^2$, $R^3$, $R^4$, $R^5$, $R^6$, $R^7$, $R_a$, m and n are as defined for compounds of formula (I), or a salt or N-oxide thereof. Preferred definitions of $R^1$, $R^2$, $R^3$, $R^4$, $R^5$, $R^6$, $R^7$, $R_a$, m and n are as defined for compounds of formula (I).

Another preferred group of compounds according to the invention are those of formula (I-7):

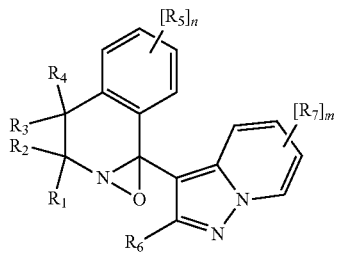

(I-7)

wherein $R^1$, $R^2$, $R^3$, $R^4$, $R^5$, $R^6$, $R^7$, m and n are as defined for compounds of formula (I), or a salt or N-oxide thereof. Preferred definitions of $R^1$, $R^2$, $R^3$, $R^4$, $R^5$, $R^6$, $R^7$, m and n are as defined for compounds of formula (I).

Another preferred group of compounds according to the invention are those of formula (I-8):

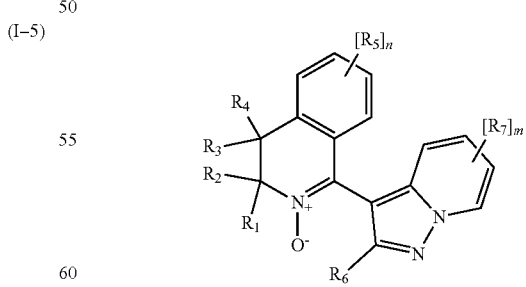

(I-8)

wherein $R^1$, $R^2$, $R^3$, $R^4$, $R^5$, $R^6$, $R^7$, m and n are as defined for compounds of formula (I), or a salt or N-oxide thereof. Preferred definitions of $R^1$, $R^2$, $R^3$, $R^4$, $R^5$, $R^6$, $R^7$, m and n are as defined for compounds of formula (I).

A further preferred group of compounds according to the invention are those of formula (I-9) which are compounds of formula (I) wherein Y—X is as defined for compounds of formula (I); $R_1$ and $R_2$ are each independently selected from hydrogen, $C_1$-$C_6$ alkyl, $C_3$-$C_7$ cycloalkyl, in which the alkyl and cycloalkyl groups may be optionally substituted with 1 to 3 substituents independently selected from halogen, $C_1$-$C_6$ alkoxy and $C_1$-$C_6$ alkylthio; or $R_1$ and $R_2$ together with the carbon atom to which they are attached represent a $C_3$-$C_6$ cycloalkyl group (which may be optionally substituted with 1 to 3 substituents independently selected from the group consisting of halogen, $C_1$-$C_6$ alkyl and $C_1$-$C_6$ alkoxy); $R_3$ and $R_4$ are each independently selected from hydrogen, halogen, hydroxyl, $C_1$-$C_6$ alkyl, $C_1$-$C_6$ alkoxy and $C_3$-$C_7$ cycloalkyl, in which the alkyl, alkoxy and cycloalkyl groups may be optionally substituted with 1 to 3 substituents independently selected from halogen, $C_1$-$C_6$ alkoxy and $C_1$-$C_6$ alkylthio; or $R_3$ and $R_4$ together with the carbon atom to which they are attached represent C=O, C=NOR$_d$, C=C(R$_b$)(R$_c$) or $C_3$-$C_6$ cycloalkyl (which may be optionally substituted with 1 to 3 substituents independently selected from the group consisting of a halogen, $C_1$-$C_6$ alkyl, $C_1$-$C_6$ alkoxy and $C_1$-$C_6$ alkylthio), where R$_b$ and R$_c$ are each independently selected from hydrogen, halogen, cyano, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy and $C_1$-$C_6$ alkylthio, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio, and where R$_d$ is selected from hydrogen, $C_1$-$C_6$ alkyl, $C_3$-$C_7$ cycloalkyl, $C_3$-$C_6$ alkenyl and $C_3$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_2$ and $R_3$ together with the carbon atoms to which they are attached represent a $C_3$-$C_7$ cycloalkyl (which may be optionally substituted with 1 to 3 substituents independently selected from the group consisting of halogen, $C_1$-$C_6$ alkyl, $C_1$-$C_6$ alkoxy and $C_1$-$C_6$ alkylthio, and, additionally, a ring carbon unit may be replaced by an oxygen or sulphur atom); each $R_5$ independently represents halogen, cyano, $C_1$-$C_6$ alkyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(=NOR$_a$)$C_1$-$C_6$alkyl, phenyl, heterorary (wherein heteroaryl is pyridyl, thiophenyl, thiazolyl, imidazolyl or oxazolyl), phenoxy or heteroraryloxy (wherein heteroaryl is pyridyl, thiophenyl, thiazolyl, imidazolyl or oxazolyl), in which the alkyl, cycloalkyl, alkenyl, alkynyl, alkoxy, alkenyloxy, alkynyloxy, phenyl and heteroaryl groups may be optionally substituted with 1 to 5 substituents independently selected from halogen, $C_1$-$C_6$ alkyl, $C_1$-$C_6$ alkoxy, cyano and $C_1$-$C_6$ alkylthio; n is 0, 1, 2, 3 or 4; $R_6$ is hydrogen, halogen, or $C_1$-$C_2$ alkyl; each $R_7$ independently represents cyano, halogen, $C_1$-$C_6$ alkyl, $C_1$-$C_6$ haloalkyl, $C_2$-$C_6$ alkenyl, $C_2$-$C_6$ alkynyl, $C_2$-$C_6$ haloalkenyl, $C_3$-$C_6$ haloalkynyl, $C_1$-$C_6$ alkylthio, $C_1$-$C_6$ haloalkoxy, $C_1$-$C_6$ haloalkylthio, $C_3$-$C_7$ cycloalkyl, $C_1$-$C_6$ alkoxy, $C_3$-$C_6$ alkenyloxy or $C_3$-$C_6$ alkynyloxy; m is 0, 1, 2, 3 or 4; and R$_a$ is hydrogen or $C_1$-$C_2$ alkyl; or a salt or N-oxide thereof.

One group of compounds according to this embodiment are compounds of formula (I-9a) which are compounds of formula (I-9) wherein $Q_1$ is a nitrogen atom and $Q_2$ is a carbon atom.

A preferred group of compounds according to this embodiment are compounds of formula (I-9b) which are compounds of formula (I-9) wherein $Q_1$ is a carbon atom and $Q_2$ is a nitrogen atom.

A further preferred group of compounds according to the invention are those of formula (I-10) which are compounds of formula (I) wherein Y—X represents the radical G1; $R_1$ and $R_2$ are each independently a hydrogen or $C_1$-$C_4$ alkyl group, in which the alkyl group may be optionally substituted with 1 to 3 substituents independently selected from halogen, and $C_1$-$C_6$ alkoxy; or $R^1$ and $R^2$ together with the carbon atom to which they are attached represent a $C_3$-$C_5$ cycloalkyl group; $R_3$ and $R_4$ are each independently selected from hydrogen, halogen, $C_1$-$C_4$ alkyl and $C_3$-$C_4$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio; or $R_3$ and $R_4$ together with the carbon atom to which they are attached represent C=O, C=NOR$_d$, or $C_3$-$C_6$ cycloalkyl (which may be optionally substituted with 1 to 3 substituents independently selected from the group consisting of a halogen, $C_1$-$C_3$ alkyl, $C_1$-$C_3$ alkoxy and $C_1$-$C_3$ alkylthio), where R$_d$ is selected from hydrogen, $C_1$-$C_4$ alkyl and $C_3$-$C_5$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio (preferably R$_d$ is selected from hydrogen and $C_1$-$C_3$ alkyl, in which the alkyl group may be optionally substituted with 1 to 3 halogen atoms (preferably fluoro atoms)); each $R_5$ independently represents halogen, cyano, $C_1$-$C_4$ alkyl, $C_3$-$C_4$ cycloalkyl, $C_1$-$C_3$ alkoxy, $C_3$-$C_6$ alkenyloxy, $C_3$-$C_6$ alkynyloxy, phenyl, heteroraryl (wherein heteroaryl is pyridyl, thiazolyl or oxazolyl), in which the alkyl, cycloalkyl, alkoxy, alkenyloxy, alkynyloxy, phenyl and heteroaryl groups may be optionally substituted with 1 to 3 substituents independently selected from halogen, $C_1$-$C_3$ alkyl and $C_1$-$C_3$ alkoxy; n is 0, 1 or 2; $R_6$ is hydrogen, fluoro, chloro, or methyl; each $R_7$ independently represents cyano, halogen, $C_1$-$C_4$ alkyl, $C_1$-$C_4$ haloalkyl, $C_2$-$C_3$ alkynyl, $C_1$-$C_4$ alkylthio or $C_3$-$C_4$ cycloalkyl; and m is 0, 1 or 2; or a salt or N-oxide thereof.

One group of compounds according to this embodiment are compounds of formula (I-10a) which are compounds of formula (I-10) wherein $Q_1$ is a nitrogen atom and $Q_2$ is a carbon atom.

A preferred group of compounds according to this embodiment are compounds of formula (I-10b) which are compounds of formula (I-10) wherein $Q_1$ is a carbon atom and $Q_2$ is a nitrogen atom.

A further preferred group of compounds according to the invention are those of formula (I-11) which are compounds of formula (I) wherein Y—X represents the radical G1; $R_1$ and $R_2$ are each independently a $C_1$-$C_3$ alkyl; or $R_1$ and $R_2$ together with the carbon atom to which they are attached represent a $C_3$-$C_4$ cycloalkyl group; $R_3$ and $R_4$ are each independently selected from hydrogen, halogen and $C_1$-$C_4$ alkyl; or $R_3$ and $R_4$ together with the carbon atom to which they are attached represent C=O or $C_3$-$C_4$ cycloalkyl; each $R_5$ independently represents halogen, cyano, $C_1$-$C_3$ alkyl, $C_3$-$C_4$ cycloalkyl; n is 0, 1 or 2; $R_6$ is hydrogen, fluoro, chloro, or methyl; each $R_7$ independently represents cyano, halogen, $C_1$-$C_3$ alkyl, $C_1$-$C_3$ haloalkyl or $C_3$-$C_4$ cycloalkyl; and m is 0, 1 or 2; or a salt or N-oxide thereof.

One group of compounds according to this embodiment are compounds of formula (I-11a) which are compounds of formula (I-11) wherein $Q_1$ is a nitrogen atom and $Q_2$ is a carbon atom.

A preferred group of compounds according to this embodiment are compounds of formula (I-11 b) which are compounds of formula (I-11) wherein $Q_1$ is a carbon atom and $Q_2$ is a nitrogen atom.

A further preferred group of compounds according to the invention are those of formula (I-12) which are compounds of formula (I) wherein Y—X represents the radical G1; $R_1$ and $R_2$ are each independently a $C_1$-$C_2$ alkyl group (preferably both are methyl); $R_3$ and $R_4$ are each independently selected from hydrogen, fluoro and $C_1$-$C_2$ alkyl (preferably both are methyl or both are fluoro); or $R_3$ and $R_4$ together with the carbon atom to which they are attached represent $C_3$-$C_4$ cycloalkyl; each $R_5$ independently represents fluoro, chloro, bromo, cyano, or $C_1$-$C_2$ alkyl (preferably fluoro); n is 0, 1 or 2 (preferably 0 or 1); $R_6$ is hydrogen; each $R_7$ independently represents fluoro, chloro or $C_1$-$C_3$ alkyl (preferably fluoro or methyl); and m is 1 or 2; or a salt or N-oxide thereof.

One group of compounds according to this embodiment are compounds of formula (I-12a) which are compounds of formula (I-12) wherein $Q_1$ is a nitrogen atom and $Q_2$ is a carbon atom.

A preferred group of compounds according to this embodiment are compounds of formula (I-12b) which are compounds of formula (I-12) wherein $Q_1$ is a carbon atom and $Q_2$ is a nitrogen atom.

A particularly preferred group of compounds are compounds of formula (IK):

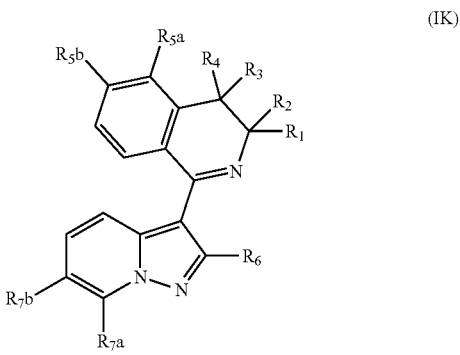

(IK)

wherein $R_1$ is methyl; $R_2$ is methyl; $R_3$ is methyl or fluoro; $R_4$ is methyl or fluoro; $R_5a$ is fluoro or hydrogen; $R_5b$ is fluoro or hydrogen; $R_6$ is hydrogen; $R_7a$ is methyl or hydrogen; and $R_7b$ is methyl, fluoro or hydrogen; or a salt or N-oxide thereof.

In compounds of formula (IK) special preference is given to compounds wherein $R_1$ is methyl, $R_2$ is methyl, $R_6$ is hydrogen and $R_3$, $R_4$, $R_5a$, $R_5b$, $R_7a$ and $R_7b$ are as defined below:

| Compound | $R_3$ | $R_4$ | $R_5a$ | $R_5b$ | $R_7a$ | $R_7b$ |
| --- | --- | --- | --- | --- | --- | --- |
| IK-1 | methyl | methyl | fluoro | hydrogen | methyl | methyl |
| IK-2 | fluoro | fluoro | fluoro | hydrogen | methyl | methyl |
| IK-3 | fluoro | fluoro | hydrogen | fluoro | methyl | methyl |
| IK-4 | fluoro | fluoro | hydrogen | hydrogen | methyl | methyl |
| IK-5 | fluoro | fluoro | hydrogen | hydrogen | methyl | fluoro |
| IK-6 | fluoro | fluoro | hydrogen | hydrogen | methyl | hydrogen |
| IK-7 | fluoro | fluoro | hydrogen | hydrogen | hydrogen | methyl |
| IK-8 | methyl | methyl | fluoro | hydrogen | methyl | hydrogen |
| IK-9 | fluoro | fluoro | hydrogen | fluoro | methyl | hydrogen |
| IK-10 | fluoro | fluoro | hydrogen | fluoro | hydrogen | methyl |

Compounds according to the invention may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

Specific examples of compounds of formula (I) are illustrated in the Tables A1 to A17 and B1 to B17 below:

Table A1 provides 195 compounds of formula Ia

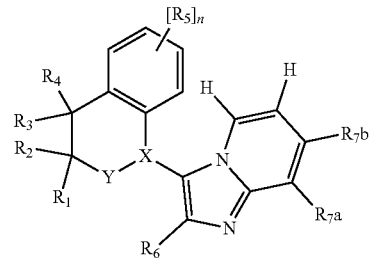

wherein $R_6$, $R_{7a}$ and $R_{7b}$ are all H
and wherein the values of $R_1$, $R_2$, $R_3$, $R_4$, $R_5$ and the radical Y—X (and when Y—X is G2 the corresponding Ra) are as defined in Table Z below:

TABLE Z

| Entry | $R_1$ | $R_2$ | $R_3$ | $R_4$ | $R_5$ | Y-X* | $R_a$ |
|---|---|---|---|---|---|---|---|
| 1 | CH$_3$ | CH$_3$ | H | H | H [n = 0] | G1 | — |
| 2 | CH$_3$ | CH$_3$ | H | H | 5-F | G1 | — |
| 3 | CH$_3$ | CH$_3$ | H | H | 6-F | G1 | — |
| 4 | CH$_3$ | CH$_3$ | H | H | 7-F | G1 | — |
| 5 | CH$_3$ | CH$_3$ | H | H | 8-F | G1 | — |
| 6 | CH$_3$ | CH$_3$ | H | H | 5-Cl | G1 | — |
| 7 | CH$_3$ | CH$_3$ | H | H | 6-Cl | G1 | — |
| 8 | CH$_3$ | CH$_3$ | H | H | 7-Cl | G1 | — |
| 9 | CH$_3$ | CH$_3$ | H | H | 8-Cl | G1 | — |
| 10 | CH$_3$ | CH$_3$ | H | H | 5-Br | G1 | — |
| 11 | CH$_3$ | CH$_3$ | H | H | 6-Br | G1 | — |
| 12 | CH$_3$ | CH$_3$ | H | H | 5-I | G1 | — |
| 13 | CH$_3$ | CH$_3$ | H | H | 5,6-F$_2$ | G1 | — |
| 14 | CH$_3$ | CH$_3$ | H | H | 5,6-Cl$_2$ | G1 | — |
| 15 | CH$_3$ | CH$_3$ | H | H | 5-F-6-Cl | G1 | — |
| 16 | CH$_3$ | CH$_3$ | H | H | 5-CH$_3$ | G1 | — |
| 17 | CH$_3$ | CH$_3$ | H | H | 6-CH$_3$ | G1 | — |
| 18 | CH$_3$ | CH$_3$ | H | H | 7-CH$_3$ | G1 | — |
| 19 | CH$_3$ | CH$_3$ | H | H | 5-CH$_2$CH$_3$ | G1 | — |
| 20 | CH$_3$ | CH$_3$ | H | H | 5-cyclopropyl | G1 | — |
| 21 | CH$_3$ | CH$_3$ | H | H | 5-CN | G1 | — |
| 22 | CH$_3$ | CH$_3$ | H | H | 5-OCH$_3$ | G1 | — |
| 23 | CH$_3$ | CH$_3$ | H | H | 5-OC$_6$H$_5$ | G1 | — |
| 24 | CH$_3$ | CH$_3$ | H | H | 5-O-(pyrid-2-yl) | G1 | — |
| 25 | CH$_3$ | CH$_3$ | H | H | 5-CF$_3$ | G1 | — |
| 26 | CH$_3$ | CH$_3$ | H | H | 5-C$_6$H$_6$ | G1 | — |
| 27 | CH$_3$ | CH$_3$ | H | H | 5-(2-F—C$_6$H$_5$) | G1 | — |
| 28 | CH$_3$ | CH$_3$ | H | H | 5-(thiazol-2-yl) | G1 | — |
| 29 | CH$_3$ | CH$_3$ | H | H | H [n = 0] | G2 | H |
| 30 | CH$_3$ | CH$_3$ | H | H | 5-F | G2 | H |
| 31 | CH$_3$ | CH$_3$ | H | H | H [n = 0] | G2 | CH$_3$ |
| 32 | CH$_3$ | CH$_3$ | H | H | 5-F | G2 | CH$_3$ |
| 33 | CH$_3$ | CH$_3$ | H | H | H [n = 0] | G3 | — |
| 34 | CH$_3$ | CH$_3$ | H | H | 5-F | G3 | — |
| 35 | CH$_3$ | CH$_3$ | H | H | H [n = 0] | G4 | — |
| 36 | CH$_3$ | CH$_3$ | H | H | 5-F | G4 | — |
| 37 | CH$_3$ | CH$_3$ | H | CH$_3$ | H [n = 0] | G1 | — |
| 38 | CH$_3$ | CH$_3$ | H | CH$_3$ | 5-F | G1 | — |
| 39 | CH$_3$ | CH$_3$ | H | OH | H [n = 0] | G1 | — |
| 40 | CH$_3$ | CH$_3$ | H | OH | 5-F | G1 | — |
| 41 | CH$_3$ | CH$_3$ | H | OCH$_3$ | H [n = 0] | G1 | — |
| 42 | CH$_3$ | CH$_3$ | H | OCH$_3$ | 5-F | G1 | — |
| 43 | CH$_3$ | CH$_3$ | H | F | H [n = 0] | G1 | — |
| 44 | CH$_3$ | CH$_3$ | H | F | 5-F | G1 | — |
| 45 | CH$_3$ | CH$_3$ | H | F | 6-F | G1 | — |
| 46 | CH$_3$ | CH$_3$ | H | F | 5-Cl | G1 | — |
| 47 | CH$_3$ | CH$_3$ | H | F | 6-Cl | G1 | — |
| 48 | CH$_3$ | CH$_3$ | H | F | 5-CH$_3$ | G1 | — |
| 49 | CH$_3$ | CH$_3$ | CH$_3$ | CH$_3$ | H [n = 0] | G1 | — |
| 50 | CH$_3$ | CH$_3$ | CH$_3$ | CH$_3$ | 5-F | G1 | — |
| 51 | CH$_3$ | CH$_3$ | CH$_3$ | CH$_3$ | 6-F | G1 | — |
| 52 | CH$_3$ | CH$_3$ | CH$_3$ | CH$_3$ | 7-F | G1 | — |
| 53 | CH$_3$ | CH$_3$ | CH$_3$ | CH$_3$ | 8-F | G1 | — |
| 54 | CH$_3$ | CH$_3$ | CH$_3$ | CH$_3$ | 5-Cl | G1 | — |

TABLE Z-continued

| Entry | $R_1$ | $R_2$ | $R_3$ | $R_4$ | $R_5$ | Y-X* | $R_a$ |
|---|---|---|---|---|---|---|---|
| 55 | $CH_3$ | $CH_3$ | $CH_3$ | $CH_3$ | 6-Cl | G1 | — |
| 56 | $CH_3$ | $CH_3$ | $CH_3$ | $CH_3$ | 5-Br | G1 | — |
| 57 | $CH_3$ | $CH_3$ | $CH_3$ | $CH_3$ | 5,6-$F_2$ | G1 | — |
| 58 | $CH_3$ | $CH_3$ | $CH_3$ | $CH_3$ | 5,6-$Cl_2$ | G1 | — |
| 59 | $CH_3$ | $CH_3$ | $CH_3$ | $CH_3$ | 5-F-6-Cl | G1 | — |
| 60 | $CH_3$ | $CH_3$ | $CH_3$ | $CH_3$ | 5-$CH_3$ | G1 | — |
| 61 | $CH_3$ | $CH_3$ | $CH_3$ | $CH_3$ | 5-$CH_2CH_3$ | G1 | — |
| 62 | $CH_3$ | $CH_3$ | $CH_3$ | $CH_3$ | 5-cyclopropyl | G1 | — |
| 63 | $CH_3$ | $CH_3$ | $CH_3$ | $CH_3$ | 5-CN | G1 | — |
| 64 | $CH_3$ | $CH_3$ | $CH_3$ | $CH_3$ | 5-$OC_6H_5$ | G1 | — |
| 65 | $CH_3$ | $CH_3$ | $CH_3$ | $CH_3$ | 5-O-(pyrid-2-yl) | G1 | — |
| 66 | $CH_3$ | $CH_3$ | $CH_3$ | $CH_3$ | 5-$C_6H_6$ | G1 | — |
| 67 | $CH_3$ | $CH_3$ | $CH_3$ | $CH_3$ | 5-(2-F—$C_6H_5$) | G1 | — |
| 68 | $CH_3$ | $CH_3$ | $CH_3$ | $CH_3$ | 5-(thiazol-2-yl) | G1 | — |
| 69 | $CH_3$ | $CH_3$ | $CH_3$ | $CH_3$ | H [n = 0] | G2 | H |
| 70 | $CH_3$ | $CH_3$ | $CH_3$ | $CH_3$ | 5-F | G2 | H |
| 71 | $CH_3$ | $CH_3$ | $CH_3$ | $CH_3$ | H [n = 0] | G2 | $CH_3$ |
| 72 | $CH_3$ | $CH_3$ | $CH_3$ | $CH_3$ | 5-F | G2 | $CH_3$ |
| 73 | $CH_3$ | $CH_3$ | $CH_3$ | $CH_3$ | H [n = 0] | G3 | — |
| 74 | $CH_3$ | $CH_3$ | $CH_3$ | $CH_3$ | 5-F | G3 | — |
| 75 | $CH_3$ | $CH_3$ | $CH_3$ | $CH_3$ | H [n = 0] | G4 | — |
| 76 | $CH_3$ | $CH_3$ | $CH_3$ | $CH_3$ | 5-F | G4 | — |
| 77 | $CH_3$ | $CH_3$ | | =O | H [n = 0] | G1 | — |
| 78 | $CH_3$ | $CH_3$ | | =O | 5-F | G1 | — |
| 79 | $CH_3$ | $CH_3$ | | =O | 6-F | G1 | — |
| 80 | $CH_3$ | $CH_3$ | | =O | 5-Cl | G1 | — |
| 81 | $CH_3$ | $CH_3$ | | =O | 6-Cl | G1 | — |
| 82 | $CH_3$ | $CH_3$ | | =O | 5-Br | G1 | — |
| 83 | $CH_3$ | $CH_3$ | | =O | 5-CN | G1 | — |
| 84 | $CH_3$ | $CH_3$ | | =O | 5-$CH_3$ | G1 | — |
| 85 | $CH_3$ | $CH_3$ | | =O | 5-CH2CH3 | G1 | — |
| 86 | $CH_3$ | $CH_3$ | | =NOH | H [n = 0] | G1 | — |
| 87 | $CH_3$ | $CH_3$ | | =NOH | 5-F | G1 | — |
| 88 | $CH_3$ | $CH_3$ | | =NOH | 5-$CH_3$ | G1 | — |
| 89 | $CH_3$ | $CH_3$ | | =$NOCH_3$ | H [n = 0] | G1 | — |
| 90 | $CH_3$ | $CH_3$ | | =$NOCH_3$ | 5-F | G1 | — |
| 91 | $CH_3$ | $CH_3$ | | =$NOCH_3$ | 5-$CH_3$ | G1 | — |
| 92 | $CH_3$ | $CH_3$ | | =$NOCH_3$ | 5-Cl | G1 | — |
| 93 | $CH_3$ | $CH_3$ | F | F | H [n = 0] | G1 | — |
| 94 | $CH_3$ | $CH_3$ | F | F | 5-F | G1 | — |
| 95 | $CH_3$ | $CH_3$ | F | F | 6-F | G1 | — |
| 96 | $CH_3$ | $CH_3$ | F | F | 5-Cl | G1 | — |
| 97 | $CH_3$ | $CH_3$ | F | F | 6-Cl | G1 | — |
| 98 | $CH_3$ | $CH_3$ | F | F | 5-Br | G1 | — |
| 99 | $CH_3$ | $CH_3$ | F | F | 5,6-F2 | G1 | — |
| 100 | $CH_3$ | $CH_3$ | F | F | 5-F-6-Cl | G1 | — |
| 101 | $CH_3$ | $CH_3$ | F | F | 5-CN | G1 | — |
| 102 | $CH_3$ | $CH_3$ | F | F | 5-$CH_3$ | G1 | — |
| 103 | $CH_3$ | $CH_3$ | | cyclopropyl | H [n = 0] | G1 | — |
| 104 | $CH_3$ | $CH_3$ | | cyclopropyl | 5-F | G1 | — |
| 105 | $CH_3$ | $CH_3$ | | cyclopropyl | 5-Cl | G1 | — |
| 106 | $CH_3$ | $CH_3$ | | cyclopropyl | 5-CN | G1 | — |
| 107 | $CH_3$ | $CH_3$ | | cyclopropyl | 5-$CH_3$ | G1 | — |
| 108 | $CH_3$ | $CH_3$ | | cyclobutyl | H [n = 0] | G1 | — |
| 109 | $CH_3$ | $CH_3$ | | cyclobutyl | 5-F | G1 | — |
| 110 | $CH_3$ | $CH_3$ | | cyclopentyl | H [n = 0] | G1 | — |
| 111 | $CH_3$ | $CH_3$ | | cyclopentyl | 5-F | G1 | — |
| 112 | H | H | $CH_3$ | $CH_3$ | H [n = 0] | G1 | — |
| 113 | H | H | | cyclopropyl | H [n = 0] | G1 | — |
| 114 | H | H | | cyclopropyl | 5-F | G1 | — |
| 115 | H | H | | cyclobutyl | H [n = 0] | G1 | — |
| 116 | H | H | | cyclobutyl | 5-F | G1 | — |
| 117 | H | H | | cyclopentyl | H [n = 0] | G1 | — |
| 118 | H | H | | cyclopentyl | 5-F | G1 | — |
| 119 | $CH_3$ | $CH_2CH_3$ | H | H | H [n = 0] | G1 | — |
| 120 | $CH_3$ | $CH_2CH_3$ | H | H | 5-F | G1 | — |
| 121 | $CH_3$ | $CH_2CH_3$ | H | H | 5-Cl | G1 | — |
| 122 | $CH_3$ | $CH_2CH_3$ | H | H | 5-Br | G1 | — |
| 123 | $CH_3$ | $CH_2CH_3$ | H | H | 5-$CH_3$ | G1 | — |
| 124 | $CH_2CH_3$ | $CH_2CH_3$ | H | H | H [n = 0] | G1 | — |
| 125 | $CH_2CH_3$ | $CH_2CH_3$ | H | H | 5-F | G1 | — |
| 126 | $CH_2CH_3$ | $CH_2CH_3$ | H | H | 5-Cl | G1 | — |
| 127 | $CH_2CH_3$ | $CH_2CH_3$ | H | H | 5-Br | G1 | — |
| 128 | $CH_2CH_3$ | $CH_2CH_3$ | H | H | 5-$CH_3$ | G1 | — |
| 129 | $CH_3$ | $CH_2Cl$ | H | H | H [n = 0] | G1 | — |
| 130 | $CH_3$ | $CH_2Cl$ | H | H | 5-F | G1 | — |
| 131 | $CH_3$ | $CH_2Cl$ | $CH_3$ | $CH_3$ | H [n = 0] | G1 | — |
| 132 | $CH_3$ | $CH_2Cl$ | $CH_3$ | $CH_3$ | 5-F | G1 | — |

TABLE Z-continued

| Entry | $R_1$ | $R_2$ | $R_3$ | $R_4$ | $R_5$ | Y—X* | $R_a$ |
|---|---|---|---|---|---|---|---|
| 133 | $CH_3$ | $CH_2OCH_3$ | H | H | H [n = 0] | G1 | — |
| 134 | $CH_3$ | $CH_2OCH_3$ | H | H | 5-F | G1 | — |
| 135 | $CH_3$ | $CH_2OCH_3$ | $CH_3$ | $CH_3$ | H [n = 0] | G1 | — |
| 136 | $CH_3$ | $CH_2OCH_3$ | $CH_3$ | $CH_3$ | 5-F | G1 | — |
| 137 | $CH_3$ | H | H | H | H [n = 0] | G1 | — |
| 138 | $CH_3$ | H | H | H | 5-F | G1 | — |
| 139 | $CH_3$ | $CH(CH_3)_2$ | H | H | H [n = 0] | G1 | — |
| 140 | $CH_3$ | $CH(CH_3)_2$ | H | H | 5-F | G1 | — |
| 141 | $CH_3$ | $CH_2CH_2CH_3$ | H | H | H [n = 0] | G1 | — |
| 142 | $CH_3$ | $CH_2CH_2CH_3$ | H | H | 5-F | G1 | — |
| 143 | | cyclopropyl | H | H | H [n = 0] | G1 | — |
| 144 | | cyclopropyl | $CH_3$ | $CH_3$ | H [n = 0] | G1 | — |
| 145 | | cyclopropyl | =O | | H [n = 0] | G1 | — |
| 146 | | cyclopropyl | F | F | H [n = 0] | G1 | — |
| 147 | | cyclopropyl | cyclopropyl | | H [n = 0] | G1 | — |
| 148 | | cyclopropyl | H | H | 5-F | G1 | — |
| 149 | | cyclopropyl | $CH_3$ | $CH_3$ | 5-F | G1 | — |
| 150 | | cyclopropyl | =O | | 5-F | G1 | — |
| 151 | | cyclopropyl | F | F | 5-F | G1 | — |
| 152 | | cyclopropyl | cyclopropyl | | 5-F | G1 | — |
| 153 | | cyclopropyl | H | H | 5-Cl | G1 | — |
| 154 | | cyclopropyl | H | H | 5-Br | G1 | — |
| 155 | | cyclobutyl | H | H | H [n = 0] | G1 | — |
| 156 | | cyclobutyl | =O | | H [n = 0] | G1 | — |
| 157 | | cyclobutyl | F | F | H [n = 0] | G1 | — |
| 158 | | cyclobutyl | H | H | 5-F | G1 | — |
| 159 | | cyclobutyl | =O | | 5-F | G1 | — |
| 160 | | cyclobutyl | F | F | 5-F | G1 | — |
| 161 | | cyclobutyl | H | H | 5-Br | G1 | — |
| 162 | | cyclopentyl | H | H | H [n = 0] | G1 | — |
| 163 | | cyclopentyl | =O | | H [n = 0] | G1 | — |
| 164 | | cyclopentyl | F | F | H [n = 0] | G1 | — |
| 165 | | cyclopentyl | H | H | 5-F | G1 | — |
| 166 | | cyclopentyl | =O | | 5-F | G1 | — |
| 167 | | cyclopentyl | F | F | 5-F | G1 | — |
| 168 | | cyclopentyl | H | H | 5-Br | G1 | — |
| 169 | | cyclohexyl | H | H | H [n = 0] | G1 | — |
| 170 | | cyclohexyl | =O | | H [n = 0] | G1 | — |
| 171 | | cyclohexyl | F | F | H [n = 0] | G1 | — |
| 172 | | cyclohexyl | H | H | 5-F | G1 | — |
| 173 | | cyclohexyl | =O | | 5-F | G1 | — |
| 174 | | cyclohexyl | F | F | 5-F | G1 | — |
| 175 | | cyclohexyl | H | H | 5-Br | G1 | — |
| 176 | H | | cyclopropyl | H | H [n = 0] | G1 | — |
| 177 | $CH_3$ | | cyclopropyl | H | H [n = 0] | G1 | — |
| 178 | $CH_3$ | | cyclopropyl | $CH_3$ | H [n = 0] | G1 | — |
| 179 | $CH_3$ | | cyclopropyl | F | H [n = 0] | G1 | — |
| 180 | H | | cyclopropyl | H | 5-F | G1 | — |
| 181 | $CH_3$ | | cyclopropyl | H | 5-F | G1 | — |
| 182 | $CH_3$ | | cyclopropyl | $CH_3$ | 5-F | G1 | — |
| 183 | H | | cyclobutyl | H | H [n = 0] | G1 | — |
| 184 | $CH_3$ | | cyclobutyl | H | H [n = 0] | G1 | — |
| 185 | $CH_3$ | | cyclobutyl | $CH_3$ | H [n = 0] | G1 | — |
| 186 | $CH_3$ | | cyclobutyl | F | H [n = 0] | G1 | — |
| 187 | H | | cyclobutyl | H | 5-F | G1 | — |
| 188 | $CH_3$ | | cyclobutyl | H | 5-F | G1 | — |
| 189 | $CH_3$ | | cyclobutyl | $CH_3$ | 5-F | G1 | — |
| 190 | H | | cyclopentyl | H | H [n = 0] | G1 | — |
| 191 | $CH_3$ | | cyclopentyl | H | H [n = 0] | G1 | — |
| 192 | $CH_3$ | | cyclopentyl | $CH_3$ | H [n = 0] | G1 | — |
| 193 | H | | cyclohexyl | H | H [n = 0] | G1 | — |
| 194 | $CH_3$ | | cyclohexyl | H | H [n = 0] | G1 | — |
| 195 | $CH_3$ | | cyclohexyl | $CH_3$ | H [n = 0] | G1 | — |

*Radicals G1, G2, G3 and G4 are as defined for compounds of formula (I).

Table A2 provides 195 compounds of formula Ia wherein $R_7a$ and $R_7b$ are H, $R_6$ is methyl and wherein the values of $R_1$, $R_2$, $R_3$, $R_4$, $R_5$ and the radical Y—X (and when Y—X is G2 the corresponding Ra) are as defined in Table Z above.
Table A3 provides 195 compounds of formula Ia wherein $R_7a$ and $R_7b$ are H, $R_6$ is chloro and wherein the values of $R_1$, $R_2$, $R_3$, $R_4$, $R_5$ and the radical Y—X (and when Y—X is G2 the corresponding Ra) are as defined in Table Z above.
Table A4 provides 195 compounds of formula Ia wherein $R_6$ and $R_7a$ are H, $R_7b$ is methyl and wherein the values of $R_1$, $R_2$, $R_3$, $R_4$, $R_5$ and the radical Y—X (and when Y—X is G2 the corresponding Ra) are as defined in Table Z above.
Table A5 provides 195 compounds of formula Ia wherein $R_6$ and $R_7b$ are H, $R_7a$ is fluoro and wherein the values of $R_1$, $R_2$, $R_3$, $R_4$, $R_5$ and the radical Y—X (and when Y—X is G2 the corresponding Ra) are as defined in Table Z above.
Table A6 provides 195 compounds of formula Ia wherein $R_6$ and $R_7b$ are H, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table A7 provides 195 compounds of formula Ia wherein $R_6$ and $R_7b$ are H, $R_7a$ is chloro and wherein the values of $R_1$, $R_2$, $R_3$, $R_4$, $R_5$ and the radical Y—X (and when Y—X is G2 the corresponding Ra) are as defined in Table Z above.

Table A8 provides 195 compounds of formula Ia wherein $R_6$ and $R_7b$ are H, $R_7a$ is bromo and wherein the values of $R_1$, $R_2$, $R_3$, $R_4$, $R_5$ and the radical Y—X (and when Y—X is G2 the corresponding Ra) are as defined in Table Z above.

Table A9 provides 195 compounds of formula Ia wherein $R_6$ and $R_7b$ are H, $R_7a$ is ethyl and wherein the values of $R_1$, $R_2$, $R_3$, $R_4$, $R_5$ and the radical Y—X (and when Y—X is G2 the corresponding Ra) are as defined in Table Z above.

Table A10 provides 195 compounds of formula Ia wherein $R_6$ and $R_7b$ are H, $R_7a$ is cyclopropyl and wherein the values of $R_1$, $R_2$, $R_3$, $R_4$, $R_5$ and the radical Y—X (and when Y—X is G2 the corresponding Ra) are as defined in Table Z above.

Table A11 provides 195 compounds of formula Ia wherein $R_6$ is H, $R_7b$ is methyl, $R_7a$ is fluoro and wherein the values of $R_1$, $R_2$, $R_3$, $R_4$, $R_5$ and the radical Y—X (and when Y—X is G2 the corresponding Ra) are as defined in Table Z above.

Table A12 provides 195 compounds of formula Ia wherein $R_6$ is H, $R_7b$ is chloro, $R_7a$ is chloro and wherein the values of $R_1$, $R_2$, $R_3$, $R_4$, $R_5$ and the radical Y—X (and when Y—X is G2 the corresponding Ra) are as defined in Table Z above.

Table A13 provides 195 compounds of formula Ia wherein $R_6$ is H, $R_7b$ is fluoro, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table A14 provides 195 compounds of formula Ia wherein $R_6$ is H, $R_7b$ is methyl, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table A15 provides 195 compounds of formula Ia wherein $R_6$ is H, $R_7b$ is chloro, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table A16 provides 195 compounds of formula Ia wherein $R_6$ is H, $R_7b$ is methyl, $R_7a$ is chloro and wherein the values of $R_1$, $R_2$, $R_3$, $R_4$, $R_5$ and the radical Y—X (and when Y—X is G2 the corresponding Ra) are as defined in Table Z above.

Table A17 provides 195 compounds of formula Ia wherein $R_6$ is H, $R_7b$ is fluoro, $R_7a$ is cyclopropyl and wherein the values of $R_1$, $R_2$, $R_3$, $R_4$, $R_5$ and the radical Y—X (and when Y—X is G2 the corresponding Ra) are as defined in Table Z above.

Table B1 discloses 195 compounds of formula Ib

Ib wherein $R_6$, $R_7a$ and $R_7b$ are H
and wherein the values of $R_1$, $R_2$, $R_3$, $R_4$, $R_5$ and the radical Y—X (and when Y—X is G2 the corresponding Ra) are as defined in Table Z above.

Table B2 provides 195 compounds of formula Ib wherein $R_7a$ and $R_7b$ are H, $R_6$ is methyl and wherein the values of $R_1$, $R_2$, $R_3$, $R_4$, $R_5$ and the radical Y—X (and when Y—X is G2 the corresponding Ra) are as defined in Table Z above.

Table B3 provides 195 compounds of formula Ib wherein $R_7a$ and $R_7b$ are H, $R_6$ is chloro and wherein the values of $R_1$, $R_2$, $R_3$, $R_4$, $R_5$ and the radical Y—X (and when Y—X is G2 the corresponding Ra) are as defined in Table Z above.

Table B4 provides 195 compounds of formula Ib wherein $R_6$ and $R_7a$ are H, $R_7b$ is methyl and wherein the values of $R_1$, $R_2$, $R_3$, $R_4$, $R_5$ and the radical Y—X (and when Y—X is G2 the corresponding Ra) are as defined in Table Z above.

Table B5 provides 195 compounds of formula Ib wherein $R_6$ and $R_7b$ are H, $R_7a$ is fluoro and wherein the values of $R_1$, $R_2$, $R_3$, $R_4$, $R_5$ and the radical Y—X (and when Y—X is G2 the corresponding Ra) are as defined in Table Z above.

Table B6 provides 195 compounds of formula Ib wherein $R_6$ and $R_7b$ are H, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table B7 provides 195 compounds of formula Ib wherein $R_6$ and $R_7b$ are H, $R_7a$ is chloro and wherein the values of $R_1$, $R_2$, $R_3$, $R_4$, $R_5$ and the radical Y—X (and when Y—X is G2 the corresponding Ra) are as defined in Table Z above.

Table B8 provides 195 compounds of formula Ib wherein $R_6$ and $R_7b$ are H, $R_7a$ is bromo and wherein the values of $R_1$, $R_2$, $R_3$, $R_4$, $R_5$ and the radical Y—X (and when Y—X is G2 the corresponding Ra) are as defined in Table Z above.

Table B9 provides 195 compounds of formula Ib wherein $R_6$ and $R_7b$ are H, $R_7a$ is ethyl and wherein the values of $R_1$, $R_2$, $R_3$, $R_4$, $R_5$ and the radical Y—X (and when Y—X is G2 the corresponding Ra) are as defined in Table Z above.

Table B10 provides 195 compounds of formula Ib wherein $R_6$ and $R_7b$ are H, $R_7a$ is cyclopropyl and wherein the values of $R_1$, $R_2$, $R_3$, $R_4$, $R_5$ and the radical Y—X (and when Y—X is G2 the corresponding Ra) are as defined in Table Z above.

Table B11 provides 195 compounds of formula Ib wherein $R_6$ is H, $R_7b$ is methyl, $R_7a$ is fluoro and wherein the values of $R_1$, $R_2$, $R_3$, $R_4$, $R_5$ and the radical Y—X (and when Y—X is G2 the corresponding Ra) are as defined in Table Z above.

Table B12 provides 195 compounds of formula Ib wherein $R_6$ is H, $R_7b$ is chloro, $R_7a$ is chloro and wherein the values of $R_1$, $R_2$, $R_3$, $R_4$, $R_5$ and the radical Y—X (and when Y—X is G2 the corresponding Ra) are as defined in Table Z above.

Table B13 provides 195 compounds of formula Ib wherein $R_6$ is H, $R_7b$ is fluoro, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table B14 provides 195 compounds of formula Ib wherein $R_6$ is H, $R_7b$ is methyl, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table B15 provides 195 compounds of formula Ib wherein $R_6$ is H, $R_7b$ is chloro, $R_7a$ is methyl and wherein the values of $R_1$, $R_2$, $R_3$, $R_4$, $R_5$ and the radical Y—X (and when Y—X is G2 the corresponding Ra) are as defined in Table Z above.

Table B16 provides 195 compounds of formula Ib wherein $R_6$ is H, $R_7b$ is methyl, $R_7a$ is chloro and wherein the values of $R_1$, $R_2$, $R_3$, $R_4$, $R_5$ and the radical Y—X (and when Y—X is G2 the corresponding Ra) are as defined in Table Z above.

Table B17 provides 195 compounds of formula Ib wherein $R_6$ is H, $R_7b$ is fluoro, $R_7a$ is cyclopropyl and wherein the values of $R_1$, $R_2$, $R_3$, $R_4$, $R_5$ and the radical Y—X (and when Y—X is G2 the corresponding Ra) are as defined in Table Z above.

Compounds of the present invention can be made as shown in the following schemes, in which, unless otherwise stated, the definition of each variable is as defined above for a compound of formula (I).

The compounds of formula I-1, wherein $R_1$, $R_2$, $R_3$, $R_4$, $R_5$, $R_6$, $R_7$, m and n are as defined for compounds of formula (I), can be obtained by transformation of a compound of formula II, wherein $R_6$, $R_7$ and m are as defined for compounds of formula (I), with a compound of formula III, wherein $R_1$, $R_2$, $R_3$, $R_4$, $R_5$ and n are as defined for compounds of formula (I), under acidic conditions, e.g. with sulphuric acid, trifluoroacetic acid or trifluoromethansulfonic acid. This is shown in Scheme 1.

Compounds of formula III can be obtained by a variety of known methods, e.g. by addition of a Grignard reagent onto the corresponding phenyl acetic esters (see for example: Journal of the American Chemical Society, 1989, 111(12), 4392-8).

Scheme 1

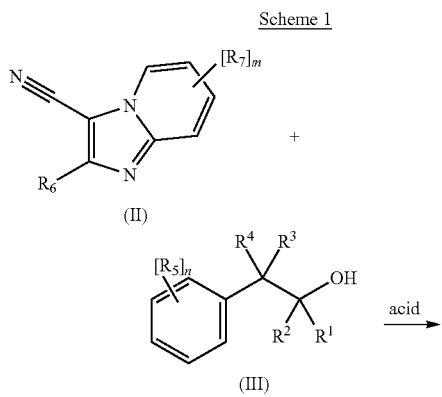

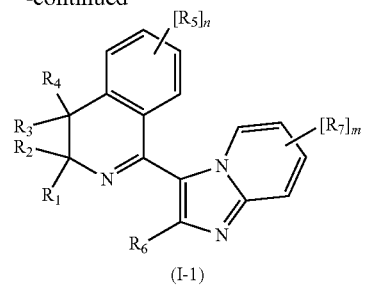
(I-1)

The compounds of formula II, wherein $R_6$, $R_7$ and m are as defined for compounds of formula I, can be obtained by transformation of an aminopyridine of formula IV (which are commercially available or obtainable by a variety of known methods), wherein $R_7$ and m are as defined for compounds of formula I, with a compound of formula V (which are commercially available or obtainable by a variety of known methods), wherein $R_6$ is as defined for compounds of formula I, under oxidative conditions, e.g. with Iodobenzene 1,1-diacetate. Alternatively, the compounds of formula II, wherein $R_6$ is H and $R_7$ and m are as defined for compounds of formula I, can be obtained by transformation of an amidine of formula VI (which are commercially available or obtainable by a variety of known methods), wherein $R^7$ and m are as defined for compounds of formula I, with a compound of formula VII (which are commercially available or obtainable by a variety of known methods), wherein Hal is a halogen, preferably chloro or bromo, under basic conditions, e.g. with sodium carbonate. This is shown in Scheme 2.

Scheme 2

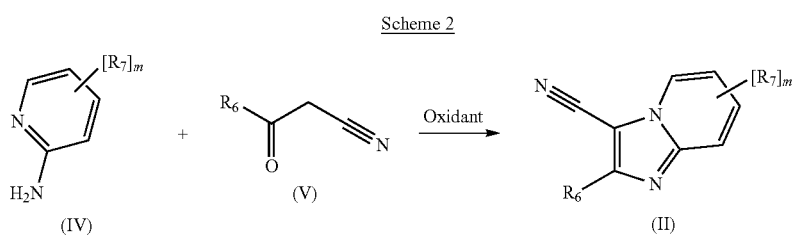

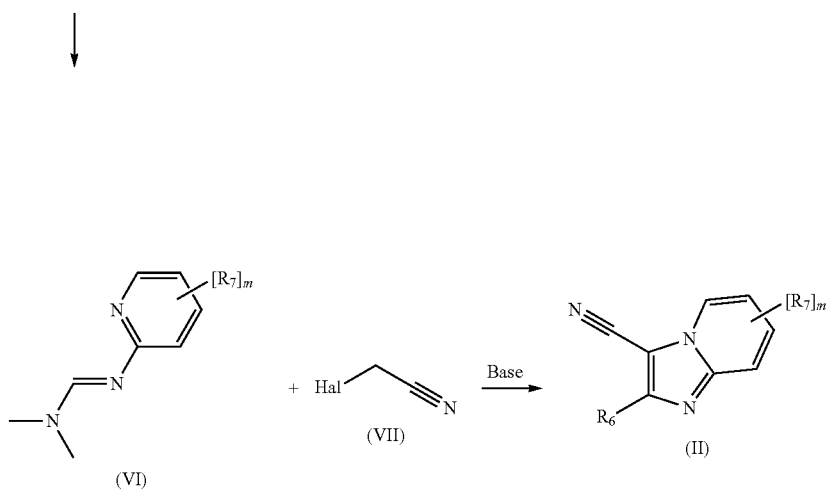

The compounds of formula I-1, wherein $R_1$, $R_2$, $R_3$, $R_4$, $R_5$, $R_6$, $R_7$, m and n are as defined for compounds of formula I, can also be obtained by transformation of a compound of formula VIII, wherein $R_6$, $R_7$ and m are as defined for compounds of formula (I) and $R_8$ is hydroxyl or two $R^8$ together with the interjacent boron atom form a five- or six membered saturated heterocyclic ring, with a compound of formula IX, wherein $R_1$, $R_2$, $R_3$, $R_4$, $R_5$ and n are as defined for compounds of formula (I) and Hal is halogen, preferably chloro or bromo, under conditions of the Suzuki-Miyaura reaction. This is shown in Scheme 3.

Compounds of formula VIII can be prepared by known methods (see for example: Eur. J. Org. Chem. 2011, 24, 4654 or in Tetrahedron 2008, 64, 4596).

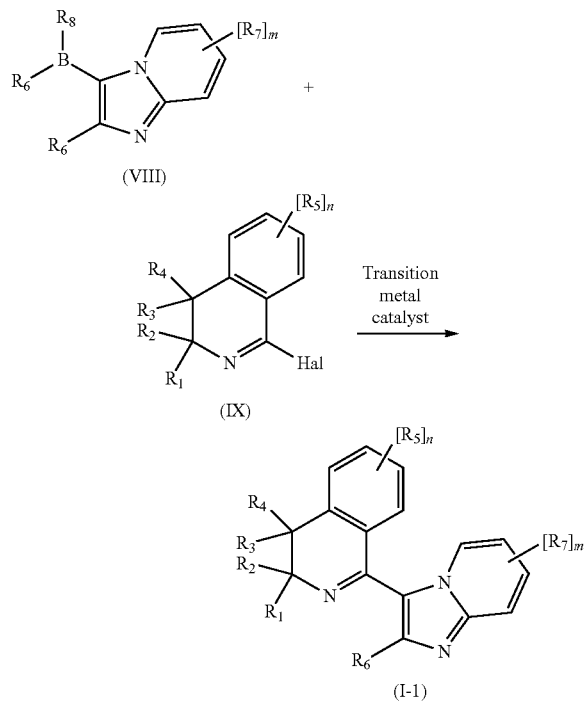

The compounds of formula IX, wherein $R_1$, $R_2$, $R_3$, $R_4$, $R_5$ and n are as defined for compounds of formula (I) and Hal is halogen, preferably chloro or bromo, can be obtained by transformation of a compound of formula X, wherein $R_1$, $R_2$, $R_3$, $R_4$, $R_5$ and n are as defined for compounds of formula I, with a halogenation reagent, such as phosphorus oxychloride phosphorus oxybromide, thionyl chloride, thionyl bromide or Vilsmeier reagent. This is shown in Scheme 4.

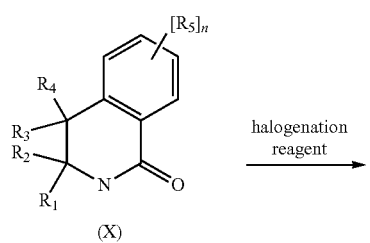

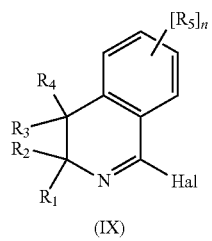

The compounds of formula X, wherein $R_1$, $R_2$, $R_3$, $R_4$, $R_5$ and n are as defined for compounds of formula I, can be obtained by several transformation known to the person skilled in the art, for instance they can be prepared by transformation of a compound of formula XI, wherein $R_1$, $R_2$, $R_3$, $R_4$, $R_5$ and n are as defined for compounds of formula (I) and $R_9$ is $C_1$-$C_6$ alkyl, with sodium acetate in acetic acid as described in the literature (Yu. B. Vikharev et al. Pharmaceutical Chemistry Journal, 2005, 39, 405-408). This is shown in Scheme 5.

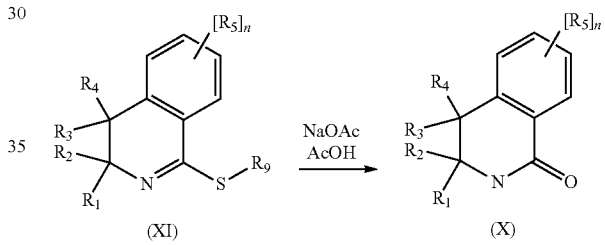

The compounds of formula XI, wherein $R_1$, $R_2$, $R_3$, $R_4$, $R_5$ and n are as defined for compounds of formula (I) and $R_9$ is $C_1$-$C_6$ alkyl, can be obtained by transformation of a compound of formula III-a, III-b or III-c, wherein $R_1$, $R_2$, $R_3$, $R_4$, $R_5$ and n are as defined for compounds of formula (I) and R' is either H or $C_1$-$C_6$ alkyl, with a $C_1$-$C_6$ alkyl thiocyanate under acidic conditions, e.g. with sulfuric acid as described in the literature (Yu. B. Vikharev et al. Pharmaceutical Chemistry Journal, 2005, 39, 405-408). This is shown in Scheme 6.

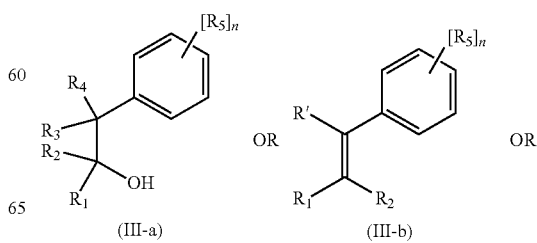

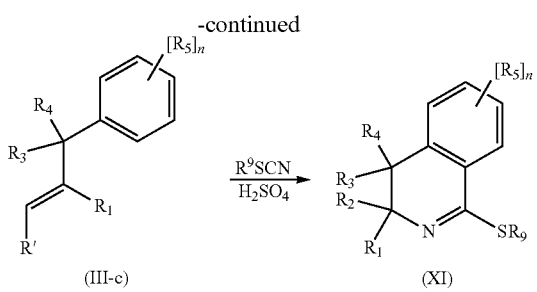

Alternatively, the compounds of formula I-1, wherein $R_1$, $R_2$, $R_3$, $R_4$, $R_5$, $R_6$, $R_7$, m and n are as defined for compounds of formula I, can be obtained by transformation of a compound of formula XII, wherein $R_6$, $R_7$ and m are as defined for formula (I) and $R_{10}$ is $C_1$-$C_6$ alkyl, with a compound of formula IX, wherein $R_1$, $R_2$, $R_3$, $R_4$, $R_5$ and n are as defined for compounds of formula (I) and Hal is halogen, preferably chloro or bromo, under conditions of the Stille reaction. This is shown in Scheme 7.

Compounds of formula XII can be prepared by known methods (see for example: Bioorg. Med. Chem. Lett. 2013, 23, 2793).

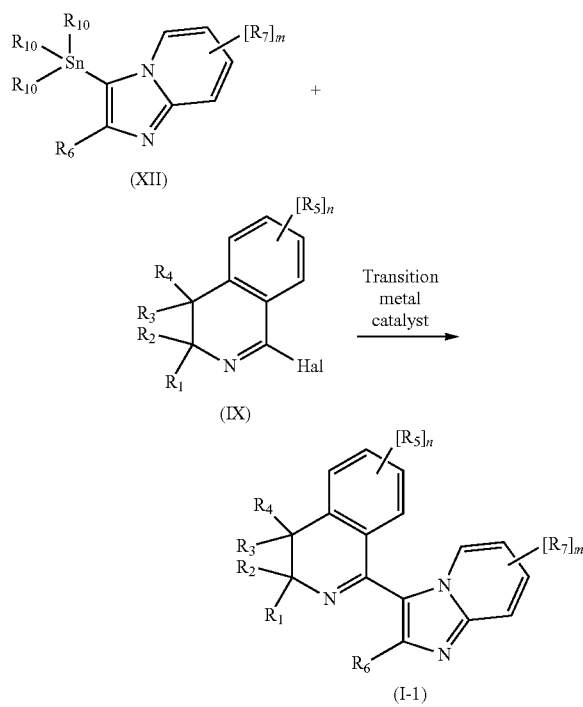

The compounds of formula III-a, III-b or III-c, wherein $R_1$, $R_2$, $R_3$, $R_4$, $R_5$ and n are as defined for compounds of formula (I) and R' is either H or $C_1$-$C_6$ alkyl, are either commercially available or easily prepared using the methods known by persons who are skilled in the art.

Alternatively, the compounds of formula X, wherein $R_1$, $R_2$, $R_3$, $R_4$, $R_5$ and n are as defined for compounds of formula I, can be obtained by transformation of a compound of formula XIII, wherein $R_1$, $R_2$, $R_3$, $R_4$, $R_5$ and n are as defined for compounds of formula I, under acidic conditions, e.g. with sulfuric acid or polyphosphoric acid as described in the literature (Jun-ichi Minamikawa, Bioorganic & Medicinal Chemistry, 2003, 11, 2205-2209). This is shown in Scheme 8.

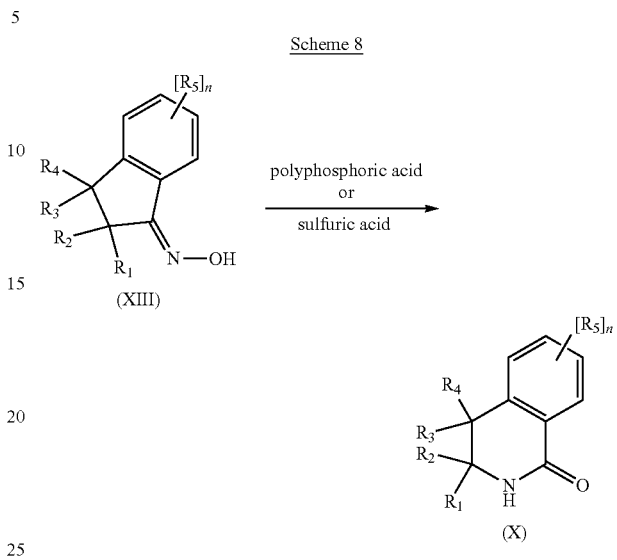

The compounds of formula XIII, wherein $R_1$, $R_2$, $R_3$, $R_4$, $R_5$ and n are as defined for compounds of formula I, can be obtained by transformation of a compound of formula XIV, wherein $R_1$, $R_2$, $R_3$, $R_4$, $R_5$ and n are as defined for compounds of formula I, upon treatment with hydroxylamine or hydroxylamine hydrochloride in a solvent such as ethanol or pyridine in the presence or absence of a base such as sodium acetate at temperatures ranging from ambient temperature to heating. This is shown in Scheme 9.

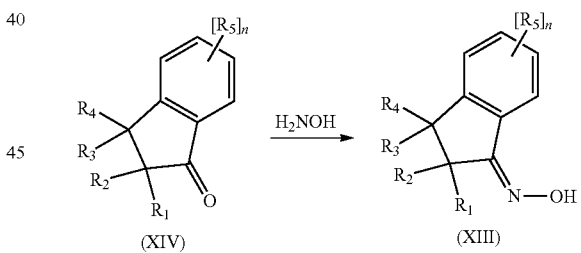

The compounds of formula XIV, wherein $R_1$, $R_2$, $R_3$, $R_4$, $R_5$ and n are as defined for compounds of formula I, are either commercially available or easily prepared using the methods known by persons who are skilled in the art.

Alternatively, the compounds of formula X, wherein $R_1$, $R_2$, $R_3$, $R_4$, $R_5$ and n are as defined for compounds of formula I, can be obtained by transformation of a compound of formula XV-a, wherein $R_1$, $R_2$, $R_3$, $R_4$, $R_5$ and n are as defined for compounds of formula I, upon treatment with carbonylating agents such as phosgene, triphosgene or carbonyl diimidazole and subsequent heating or utilizing directed catalytic C—H activation-carbonylation in the presence of carbon monoxide gas, a palladium catalyst such as palladium acetate and an oxidant such benzoquinone as reported in the literature (Jaume Granell et al. Chem. Commun., 2011, 47, 1054-1056). This is shown in Scheme 10.

Scheme 10

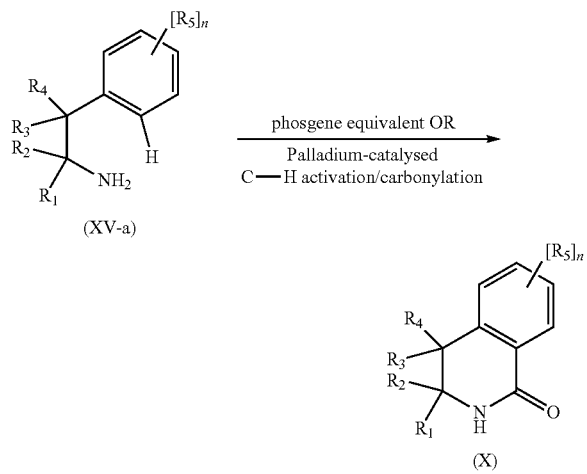

Alternatively, the compounds of formula X, wherein $R_1$, $R_2$, $R_3$, $R_4$, $R_5$ and n are as defined for compounds of formula I, can be obtained by transformation of a compound of formula XV-b, wherein $R_1$, $R_2$, $R_3$, $R_4$, $R_5$ and n are as defined for compounds of formula (I) and Hal is halogen, preferably chloro, bromo, or iodo, utilizing an intramolecular aminocarbonylation in the presence of carbon monoxide gas, a palladium catalyst such as Dichlorobis(tricyclohexylphosphine)palladium(11) or Dichlorobis(triphenlphosphine) palladium(II) and an organic base such as triethyl amine, pyrrolidine or an inorganic base such cesium carbonte or potassium carbonate as reported in the literature (Ruimao Hua et al. *Tetrahedron Letters*, 2013, 54, 5159-5161). This is shown in Scheme 11.

Scheme 11

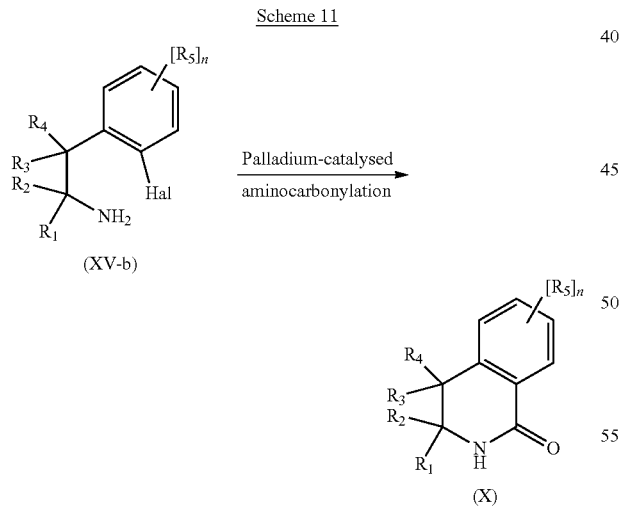

Alternatively, the compounds of formula X, wherein $R_1$, $R_2$, $R_3$, $R_4$, $R_5$ and n are as defined for compounds of formula I, can be obtained by transformation of a compound of formula XVI, wherein $R_1$, $R_2$, $R_3$, $R_4$, $R_5$ and n are as defined for compounds of formula (I) and $R_9$ is $C_1$-$C_6$ alkyl, under acid conditions e.g. sulfuric acid or triflic acid as described in the literature (Tomohiko Ohwada et al. Journal of Organic Chemistry, 2012, 77, 9313). This is shown in Scheme 12.

Scheme 12

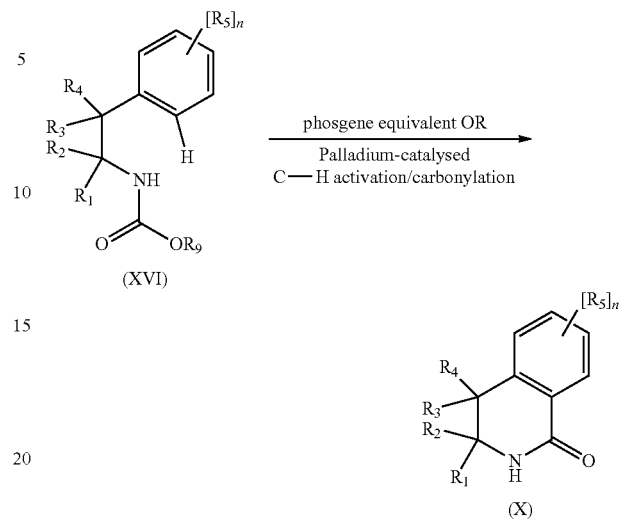

The compounds of formula I-5, wherein $R_1$, $R_2$, $R_3$, $R_4$, $R_5$, $R_6$, $R_7$ and m and n are as defined for compounds of formula I, can be obtained by transformation of a compound of formula XVII, wherein $R_6$, $R_7$ and m are as defined for compounds of formula I, with a compound of formula III, wherein $R_1$, $R_2$, $R_3$, $R_4$, $R_5$ and n are as defined for compounds of formula I, under acidic conditions, e.g. with sulphuric acid, trifluoroacetic acid or trifluoromethansulfonic acid. This is shown in Scheme 13.

Scheme 13

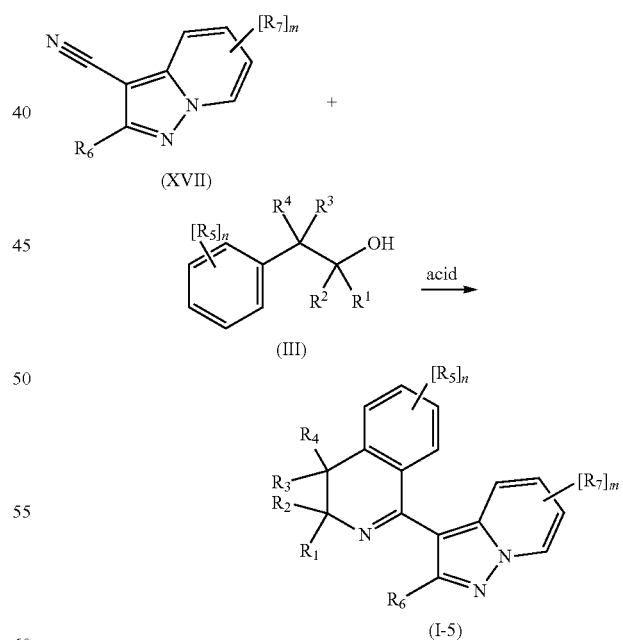

The compounds of formula XVII wherein $R_6$, $R_7$ and m are as defined for compounds of formula (I) can be obtained by known methods (see, for example: A. Kakehi et al *Chemical & Pharmaceutical Bulletin*, 1987, 35, 156-169; P. Gmeiner and J. Schunemann *Archiv de Pharmazie* 1988, 321, 517-20). As an example, compounds XVII can be prepared by reaction of 3-methoxyprop-2-enenitrile with N-amino pyridinium salts of formula XVIII (which are commercially available or can be obtained by known methods) wherein $R^7$ and m are as defined for formula (I) and the anion $A^-$ can be of different nature (e. g. iodide or 2,4,6-trimethylbenzenesulfonate), in the presence of a base, e. g. with potassium carbonate. This is shown in Scheme 14.

Scheme 14

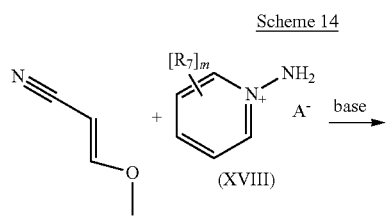

(XVIII)

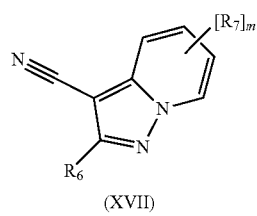

(XVII)

The compounds of formula I-5, wherein $R_1$, $R_2$, $R_3$, $R_4$, $R_5$, $R_6$, $R_7$ and m and n are as defined for compounds of formula I, can be obtained by transformation of a compound of formula XIX, wherein $R_6$, $R_7$ and m are as defined for compounds of formula (I) and $R_8$ is hydroxyl or two $R^8$ together with the interjacent boron atom form a five- or six membered saturated heterocyclic ring, with a compound of formula IX, wherein $R_1$, $R_2$, $R_3$, $R_4$, $R_5$ and n are as defined for compounds of formula (I) and Hal is halogen, preferably chloro or bromo, under conditions of the Suzuki-Miyaura reaction. This is shown in Scheme 15.

Scheme 15

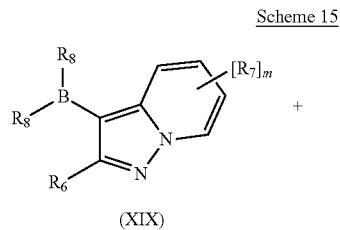

(XIX)

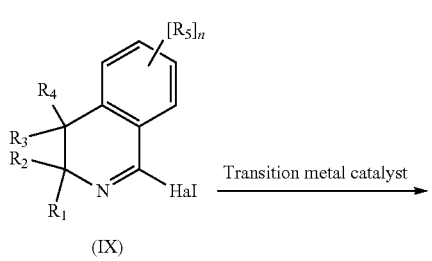

(IX)

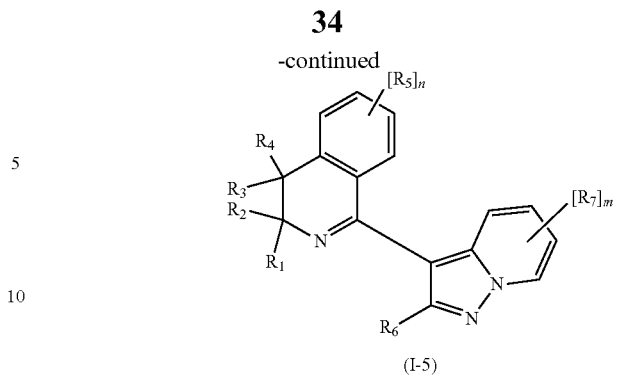

(I-5)

Alternatively, the compounds of formula I-5, wherein $R_1$, $R_2$, $R_3$, $R_4$, $R_5$, $R_6$, $R_7$ and m and n are as defined for compounds of formula I, can be obtained by transformation of a compound of formula XX, wherein $R_6$, $R_7$ and m are as defined for compounds of formula (I) and $R_{10}$ is $C_1$-$C_6$ alkyl, with a compound of formula IX, wherein $R_1$, $R_2$, $R_3$, $R_4$, $R_5$ and n are as defined for compounds of formula (I) and Hal is halogen, preferably chloro or bromo, under conditions of the Stille reaction. This is shown in Scheme 16.

Scheme 16

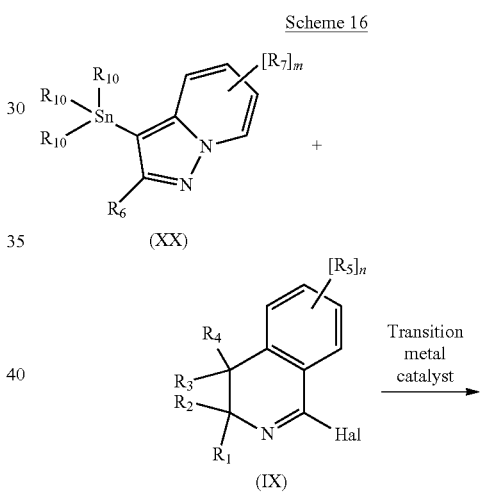

(XX)

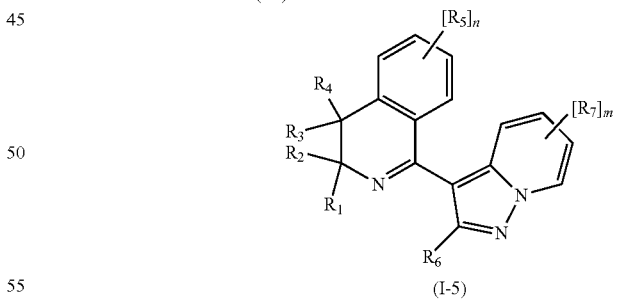

(I-5)

Alternatively, the compounds of formula I-5, wherein $R_1$, $R_2$, $R_3$, $R_4$, $R_5$, $R_6$, $R_7$ and m and n are as defined for compounds of formula I, can be obtained by treatment of a compound of formula IX-c, wherein $R_1$, $R_2$, $R_3$, $R_4$, $R_5$, $R_6$ and n are as defined for compounds of formula I, with a compound of formula XVIII, wherein $A^-$ is as defined in scheme 14, $R_7$ and m are as defined for compounds of formula I, in the presence of a base such as potassium carbonate in inert solvent such as dimethylformamide. This is shown in Scheme 17.

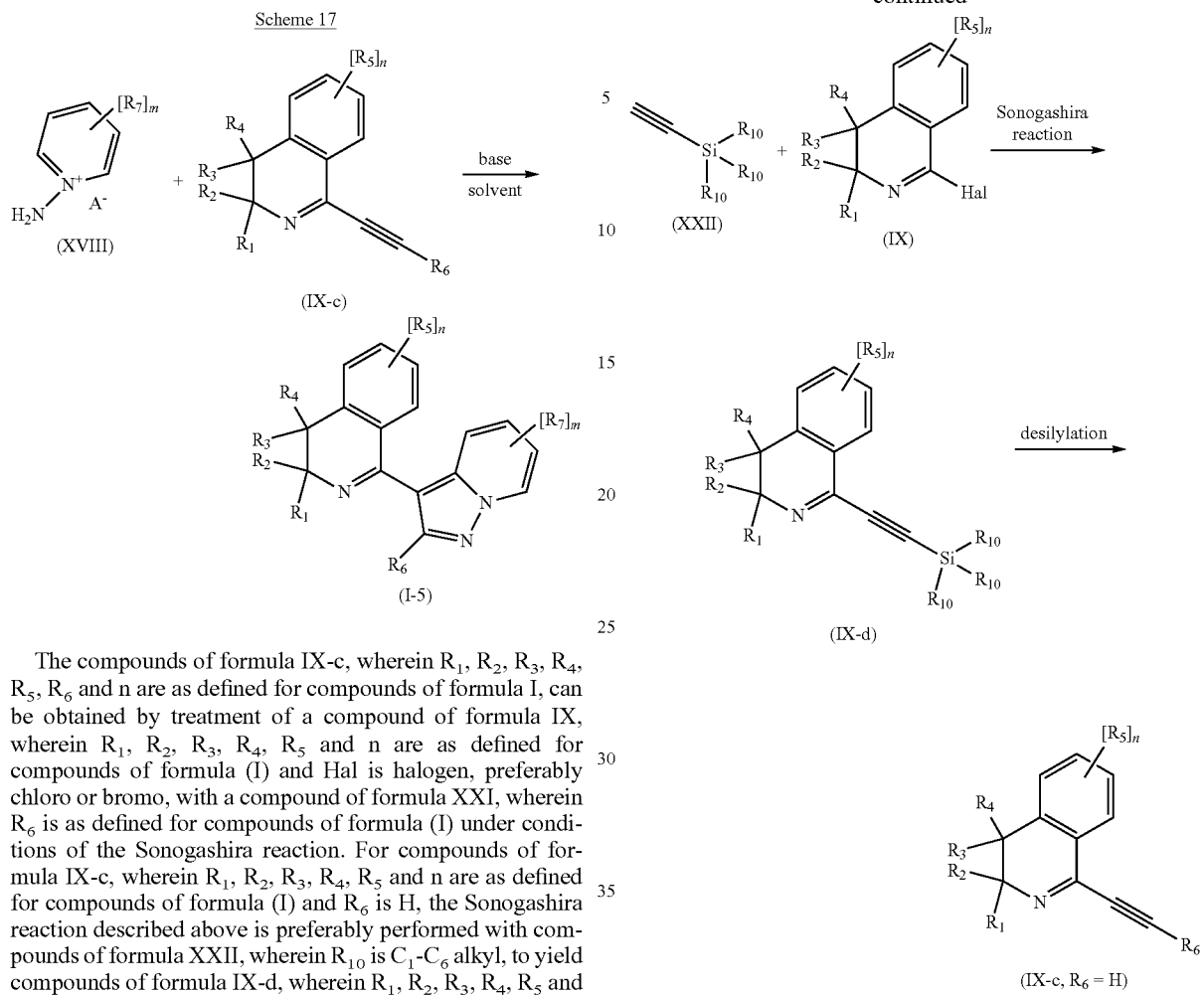

The compounds of formula IX-c, wherein $R_1$, $R_2$, $R_3$, $R_4$, $R_5$, $R_6$ and n are as defined for compounds of formula I, can be obtained by treatment of a compound of formula IX, wherein $R_1$, $R_2$, $R_3$, $R_4$, $R_5$ and n are as defined for compounds of formula (I) and Hal is halogen, preferably chloro or bromo, with a compound of formula XXI, wherein $R_6$ is as defined for compounds of formula (I) under conditions of the Sonogashira reaction. For compounds of formula IX-c, wherein $R_1$, $R_2$, $R_3$, $R_4$, $R_5$ and n are as defined for compounds of formula (I) and $R_6$ is H, the Sonogashira reaction described above is preferably performed with compounds of formula XXII, wherein $R_{10}$ is $C_1$-$C_6$ alkyl, to yield compounds of formula IX-d, wherein $R_1$, $R_2$, $R_3$, $R_4$, $R_5$ and n are as defined for compounds of formula (I) and $R_{10}$ is $C_1$-$C_6$ alkyl, followed by desilylation under conditions well known to a person skilled in the art such as potassium carbonate in an alcohol solvents such as methanol. This is shown in Scheme 18.

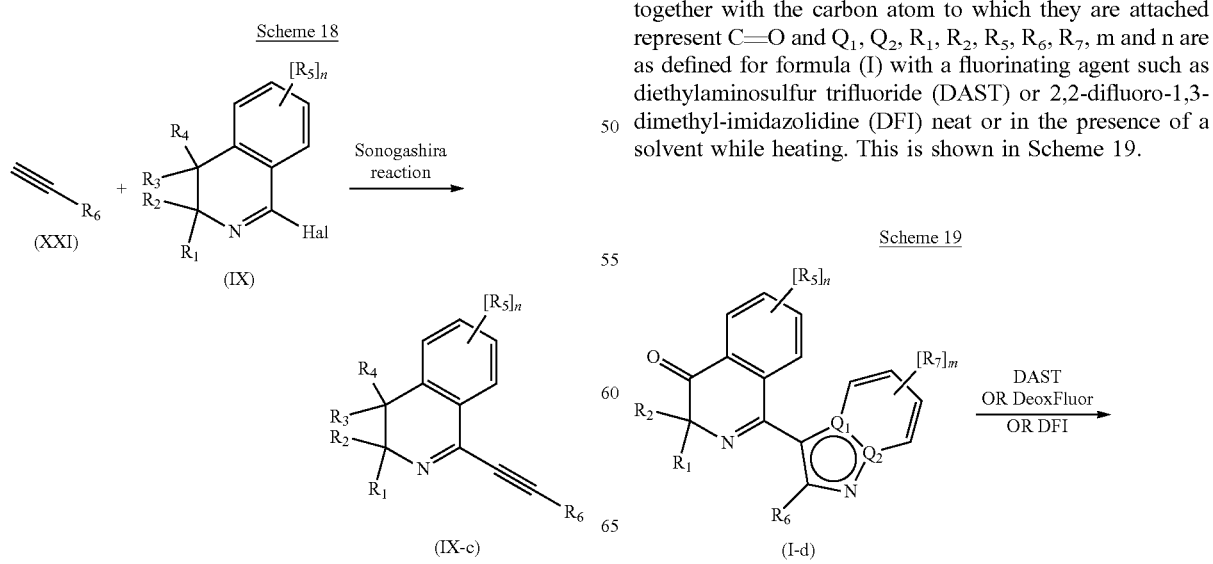

The compounds of formula I-c, wherein $R_3$ and $R_4$ are fluoro and $Q_1$, $Q_2$, $R_1$, $R_2$, $R_5$, $R_6$, $R_7$, m and n are as defined for compounds of formula I, can be obtained by transformation of a compound of formula I-d wherein $R_3$ and $R_4$ together with the carbon atom to which they are attached represent C=O and $Q_1$, $Q_2$, $R_1$, $R_2$, $R_5$, $R_6$, $R_7$, m and n are as defined for formula (I) with a fluorinating agent such as diethylaminosulfur trifluoride (DAST) or 2,2-difluoro-1,3-dimethyl-imidazolidine (DFI) neat or in the presence of a solvent while heating. This is shown in Scheme 19.

-continued

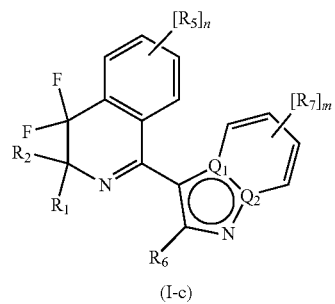

(I-c)

The compounds of formula I-d wherein $R_3$ and $R_4$ together with the carbon atom to which they are attached represent C=O and $Q_1$, $Q_2$, $R_1$, $R_2$, $R_5$, $R_6$, $R_7$, m and n are as defined for formula I, can be obtained by transformation of a compound of formula I-e wherein $R^3$ is hydrogen and $R^4$ is hydroxy and $Q_1$, $Q_2$, $R_1$, $R_2$, $R_5$, $R_6$, $R_7$, m and n are as defined for formula (I) with an oxidizing agent such as 1,1,1-triacetoxy-1,1-dihydro-1,2-benziodoxol3(1H)-one (Dess-Martin periodinane) or using oxalyl chloride, dimethyl sulfoxide (DMSO) and an organic base, such as triethylamine (Swern oxidation). This is shown in Scheme 20.

Scheme 20

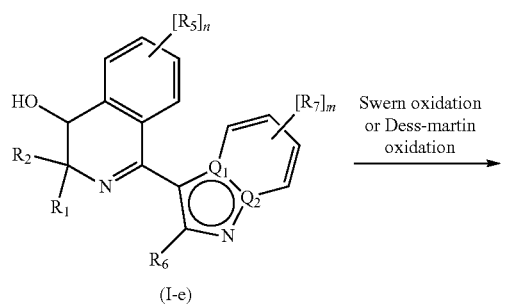

(I-d)

The compounds of formula I-e wherein $R_3$ is hydrogen and $R_4$ is hydroxy and $Q_1$, $Q_2$, $R_1$, $R_2$, $R_5$, $R_6$, $R_7$, m and n are as defined for formula I, can be obtained by transformation of a compound of formula I-f wherein $R_3$ is hydrogen and $R_4$ is halogen (hal) such as bromo or chloro and $Q_1$, $Q_2$, $R_1$, $R_2$, $R_5$, $R_6$, $R_7$, m and n are as defined for formula (I) under hydrolysis condition such as aqueous $K_2CO_3$. This is shown in Scheme 21.

Scheme 21

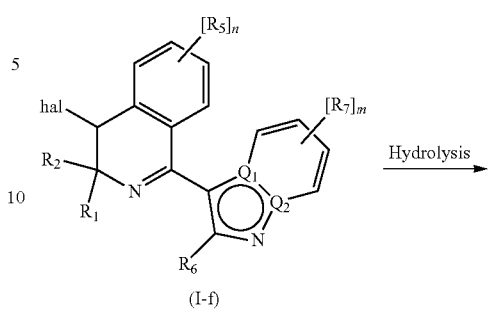

(I-e)

The compound of formula I-f wherein $R_3$ is hydrogen and $R_4$ is halogen (hal) such as bromo or chloro and $Q_1$, $Q_2$, $R_1$, $R_2$, $R_5$, $R_6$, $R_7$, m and n are as defined for formula I, can be obtained by transformation of a compound of formula I-g wherein $R^3$ and $R^4$ are hydrogen and $Q_1$, $Q_2$, $R_1$, $R_2$, $R_5$, $R_6$, $R_7$, m and n are as defined for formula (I) with an halogenating agent such as N-bromo succinimide (NBS) or N-chloro succinimide or 1,3-dibromo-5,5-dimethylhydantoin in the presence of a radical initiator such as azobisisobutyronitrile (AIBN). This is shown in Scheme 22.

Scheme 22

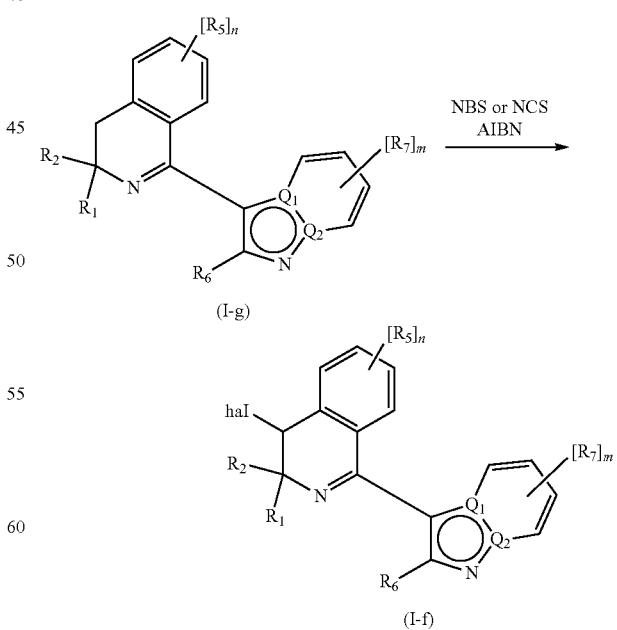

(I-f)

The compounds of formula I-g can be obtained according to the method described in Schemes 1, 3, 4, 12, 14 and 15.

Alternatively, the compounds of formula I-d wherein $R_3$ and $R_4$ together with the carbon atom to which they are attached represent C=O and $Q_1$, $Q_2$, $R_1$, $R_2$, $R_5$, $R_6$, $R_7$, m and n are as defined for formula I, can be obtained by transformation of a compound of formula VIII or XII or XIX or XX wherein $R_6$, $R_7$ and m are as defined for compounds of formula (I) and $R_8$ is hydroxyl or two $R_8$ together with the interjacent boron atom form a five- or six membered saturated heterocyclic ring or $R_{10}$ is $C_1$-$C_6$ alkyl, with a compound of formula IX-a, wherein $R_3$ and $R_4$ together with the carbon atom to which they are attached represent C=O and $R_1$, $R_2$, $R_5$ and n are as defined for compounds of formula (I) and Hal is halogen, preferably chloro or bromo, under conditions of the Suzuki-Miyaura reaction or Stille reaction. This is shown in scheme 23.

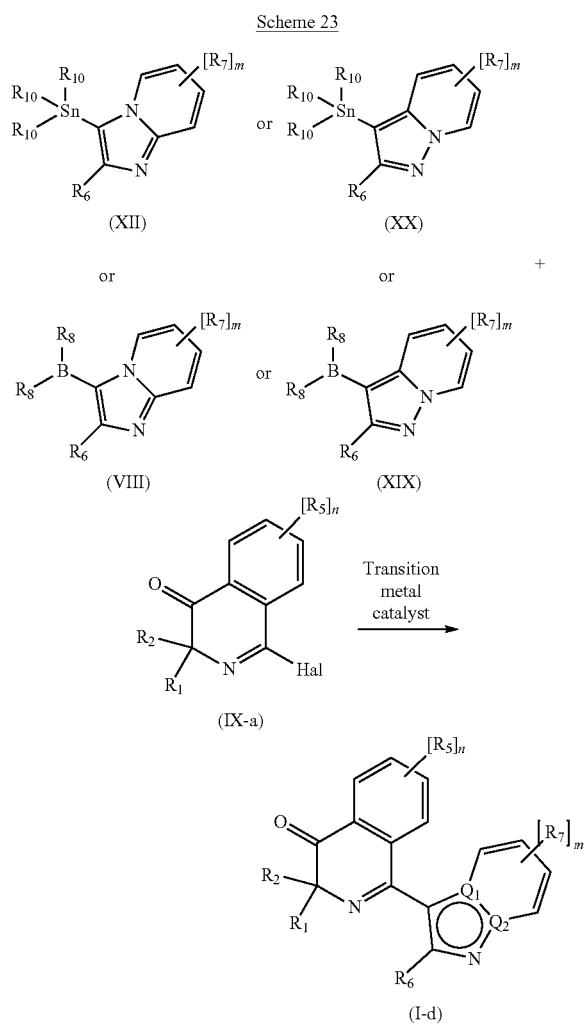

(I-d)

Alternatively, the compounds of formula I-c wherein $R_3$ and $R_4$ are fluoro and $Q_1$, $Q_2$, $R_1$, $R_2$, $R_5$, $R_6$, $R_7$, m and n are as defined for compounds of formula I, can be obtained by transformation of a compound of formula VIII or XII or XIX or XX wherein $R_6$, $R_7$ and m are as defined for compounds of formula (I) and $R_8$ is hydroxyl or two $R_8$ together with the interjacent boron atom form a five- or six membered saturated heterocyclic ring or $R_{10}$ is $C_1$-$C_6$ alkyl, with a compound of formula IX-b, wherein $R_3$ and $R_4$ are fluoro and $R_1$, $R_2$, $R_5$ and n are as defined for compounds of formula (I) and Hal is halogen, preferably chloro or bromo, under conditions of the Suzuki-Miyaura reaction or Stille reaction. This is shown in scheme 24.

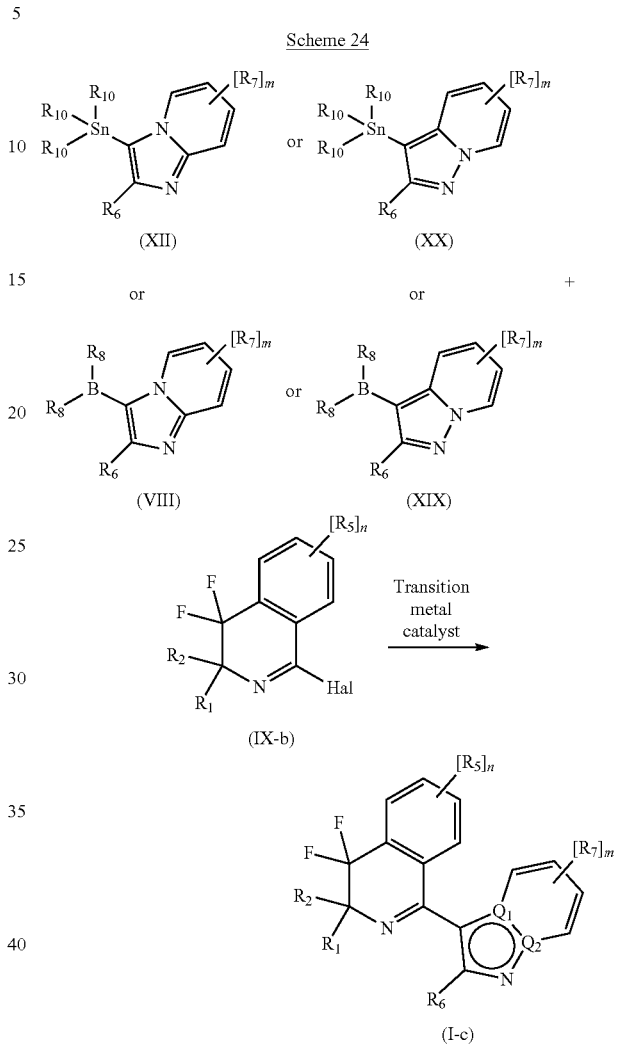

The compound of formula IX-a and IX-b can be prepared by analogy to schemes 20, 21 and 22 starting from a compound of formula X wherein $R_3$ and $R_4$ are hydrogen and $R_1$, $R_2$, $R_5$ and n are as defined for compounds of formula I.

Alternatively, the compounds of formula I, wherein $Q_1$, $Q_2$, $R_1$, $R_2$, $R_3$, $R_4$, $R_5$, $R_6$, $R_7$, m and n are as defined for compounds of formula I, can be obtained by transformation of a compound of formula I-h, wherein $Q_1$, $Q_2$, $R_1$, $R_2$, $R_3$, $R_4$, $R_6$, $R_7$, m and n are as defined for formula (I) and Z represents chlorine, bromine or iodine in a solvent, in the presence of or absence of a base, and in the presence of a coupling reagent and a metal catalyst. There are no particular limitations on the coupling agent, catalyst, solvent and bases, provided it is used in ordinary coupling reactions, such as those described in "Cross-Coupling Reactions: A Practical Guide (Topics in Current Chemistry)", edited by Norio Miyaura and S. L. Buchwald (editions Springer), or "Metal-Catalyzed Cross-Coupling Reactions", edited by Armin de Meijere and François Diederich (editions WILEY-VCH). This is shown in Scheme 25.

Scheme 25

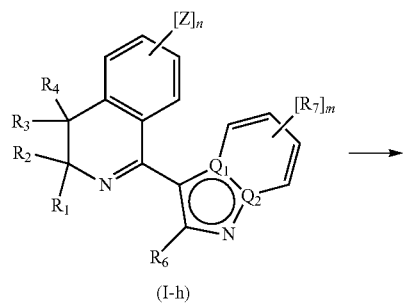

(I-h)

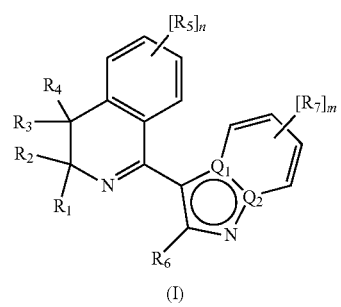

(I)

Alternatively, the compounds of formula I, wherein $Q_1$, $Q_2$, $R_1$, $R_2$, $R_3$, $R_4$, $R_5$, $R_6$, $R_7$, m and n are as defined for compounds of formula I, can be obtained by transformation of a compound of formula I-i, wherein $Q_1$, $Q_2$, $R_1$, $R_2$, $R_3$, $R_4$, $R_5$, $R_6$, m and n are as defined for compounds of formula (I) and Y represents chlorine, bromine or iodine in a solvent, in the presence of or absence of a base, and in the presence of a coupling reagent and a metal catalyst. There are no particular limitations on the coupling agent, catalyst, solvent and bases, provided it is used in ordinary coupling reactions, such as those described in "Cross-Coupling Reactions: A Practical Guide (Topics in Current Chemistry)", edited by Norio Miyaura and S. L. Buchwald (editions Springer), or "Metal-Catalyzed Cross-Coupling Reactions", edited by Armin de Meijere and François Diederich (editions WILEY-VCH). This is shown in Scheme 26.

Scheme 26

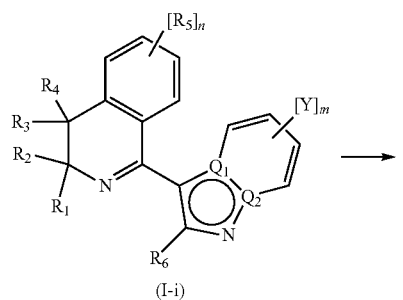

(I-i)

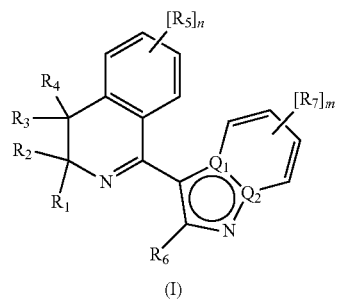

(I)

Alternatively, the compounds of formula (I) wherein $Q_1$, $Q_2$, $R_1$, $R_2$, $R_3$, $R_4$, $R_5$, $R_6$, $R_7$, m and n are as defined above, can be obtained by transformation of another, closely related, compound of formula (I) (or an analogue thereof) using standard synthesis techniques known to the person skilled in the art. Non-exhaustive examples include oxidation reactions, reduction reactions, hydrolysis reactions, coupling reactions, aromatic nucleophilic or electrophilic substitution reactions, nucleophilic substitution reactions, nucleophilic addition reactions, and halogenation reactions.

The compounds of formula I-2 and I-6, wherein $R_1$, $R_2$, $R_3$, $R_4$, $R_5$, $R_6$, $R_7$, $R_a$, m and n are as defined for compounds of formula I, can be obtained by transformation of a compound of formula I-1 or 1-5, wherein $R_1$, $R_2$, $R_3$, $R_4$, $R_5$, $R_6$, $R_7$, m and n are as defined for compounds of formula I, under reductive reaction conditions, e.g. with hydrogen and a catalyst. The ring nitrogen of the tetrahydroisoquinoline in the compounds of formulas I-2 and I-6 (when $R^a$=H) can further be alkylated (to give $R^a$=$C_1$-$C_6$ alkyl) by reaction with a $C_1$-$C_6$ alkylhalide and a base, or acylated (to give $R^a$=$C_1$-$C_6$ alkylcarbonyl) by transformation with a $C_1$-$C_6$ alkylcarbonylhalide and a base. This is shown in Scheme 27.

Scheme 27

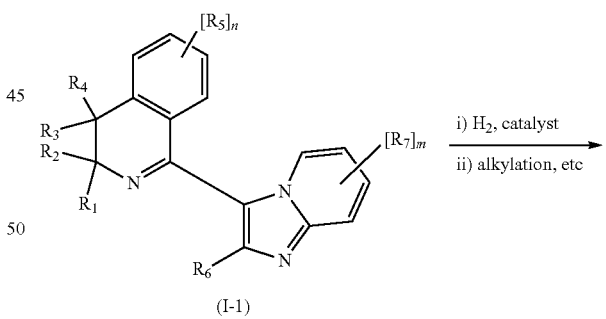

(I-1)

(I-2)

43
-continued

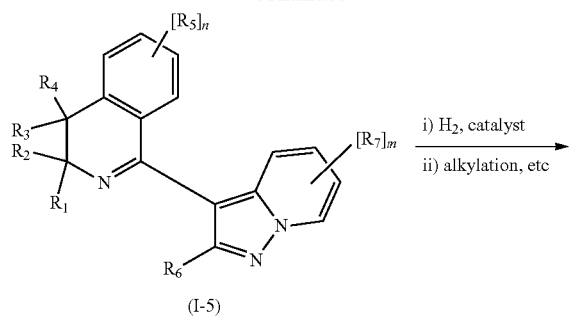

(I-5)

i) H$_2$, catalyst
ii) alkylation, etc

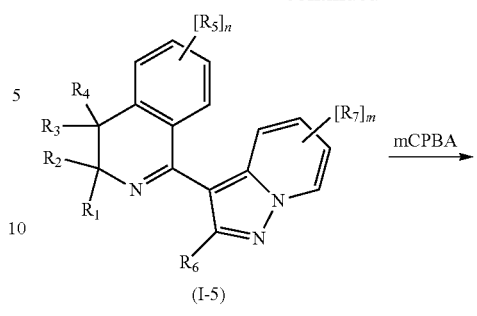

(I-5)

mCPBA

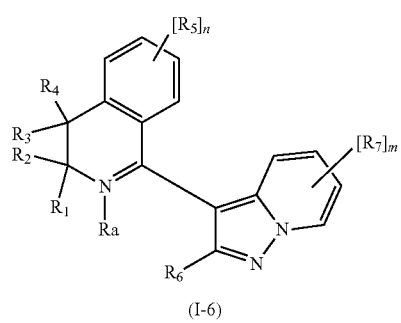

(I-6)

44
-continued

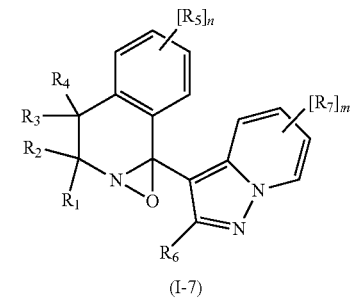

(I-7)

The compounds of formula I-3 and I-7, wherein R$_1$, R$_2$, R$_3$, R$_4$, R$_5$, R$_6$, R$_7$, m and n are as defined for compounds of formula I, can be obtained by transformation of a compound of formula I-1 or 1-5, wherein R$_1$, R$_2$, R$_3$, R$_4$, R$_5$, R$_6$, R$_7$, m and n are as defined for compounds of formula I, under oxidative reaction conditions, e.g. with meta-chloroperbenzoic acid. This is shown in Scheme 28.

The compounds of formula I-4 and 1-8, wherein R$_1$, R$_2$, R$_3$, R$_4$, R$_5$, R$_6$, R$_7$, m and n are as defined for compounds of formula I, can be obtained by transformation of a compound of formula I-1 or 1-5, wherein R$_1$, R$_2$, R$_3$, R$_4$, R$_5$, R$_6$, R$_7$, m and n are as defined for compounds of formula I, under oxidative reaction conditions, e.g. with methyltrioxorhenium and urea hydrogen peroxide. This is shown in Scheme 29.

Scheme 28

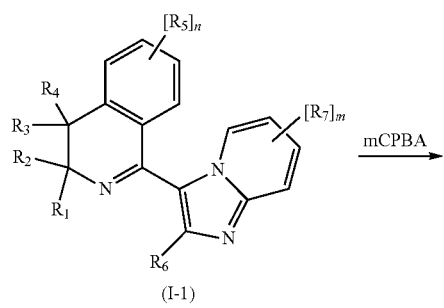

(I-1)

mCPBA

Scheme 29

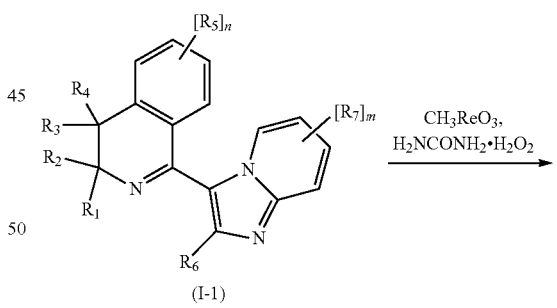

(I-1)

CH$_3$ReO$_3$,
H$_2$NCONH$_2$·H$_2$O$_2$

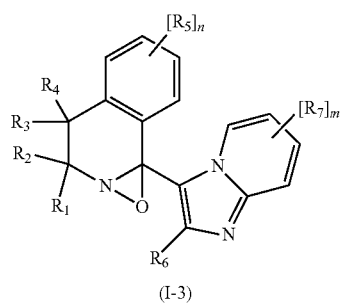

(I-3)

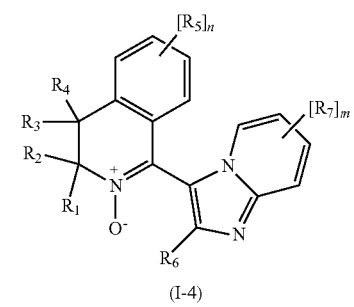

(I-4)

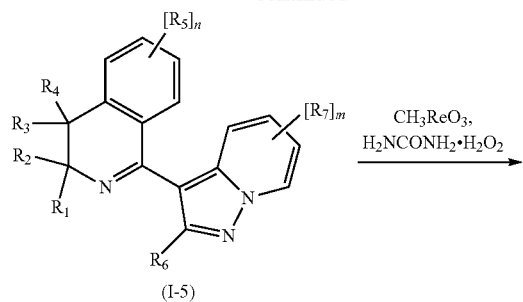

(I-5)

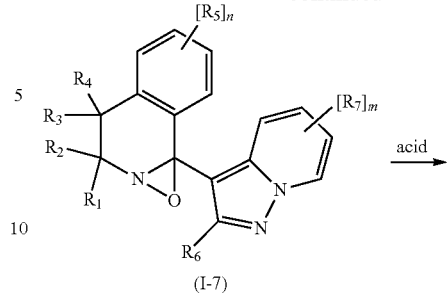

(I-7)

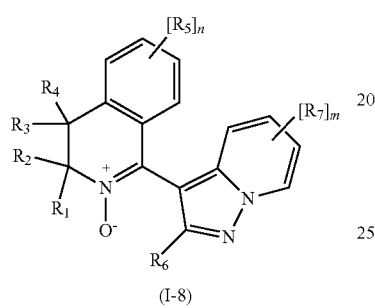

(I-8)

Alternatively, the compounds of formula I-4 and I-8, wherein R $R_1$, $R_2$, $R_3$, $R_4$, $R_5$, $R_6$, $R_7$, m and n are as defined for compounds of formula I, can be obtained by transformation of a compound of formula I-3 and I-7, wherein $R_1$, $R_2$, $R_3$, $R_4$, $R_5$, $R_6$, $R_7$, m and n are as defined for compounds of formula I, under acidic conditions, e.g. with methanesulfonic acid. This is shown in Scheme 30.

Scheme 30

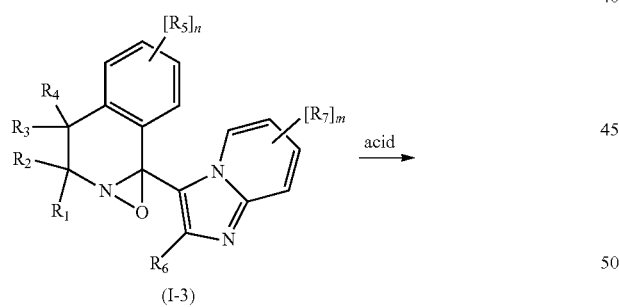

(I-3)

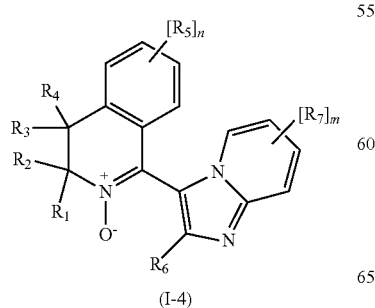

(I-4)

Certain intermediates described in the above schemes are novel and as such form a further aspect of the invention.

One group of novel intermediates are compounds of formula (XA):

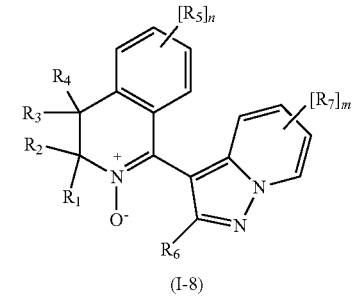

(XA)

wherein $R_5a$ is fluoro or hydrogen; and $R_5b$ is fluoro or hydrogen; and compounds of formula (XB):

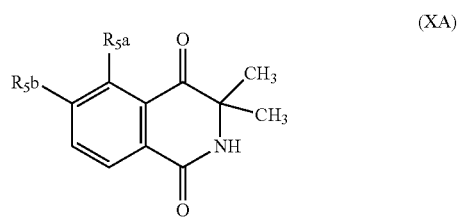

(XB)

wherein $R_5a$ is fluoro or hydrogen; and $R_5b$ is fluoro or hydrogen; and compounds of formula (XC):

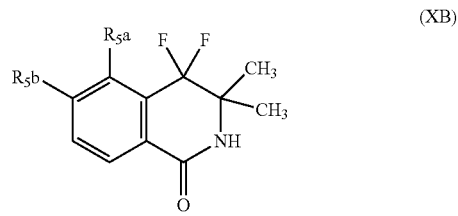

(XC)

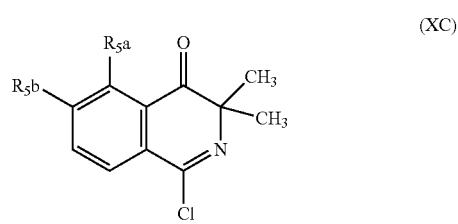

wherein R$_5$a is fluoro or hydrogen; and R$_5$b is fluoro or hydrogen; and compounds of formula (XD):

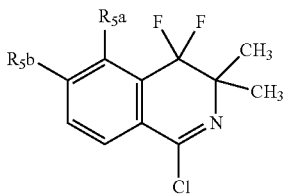

wherein R$_5$a is fluoro or hydrogen; and R$_5$b is fluoro or hydrogen.

Particularly preferred novel intermediates are:

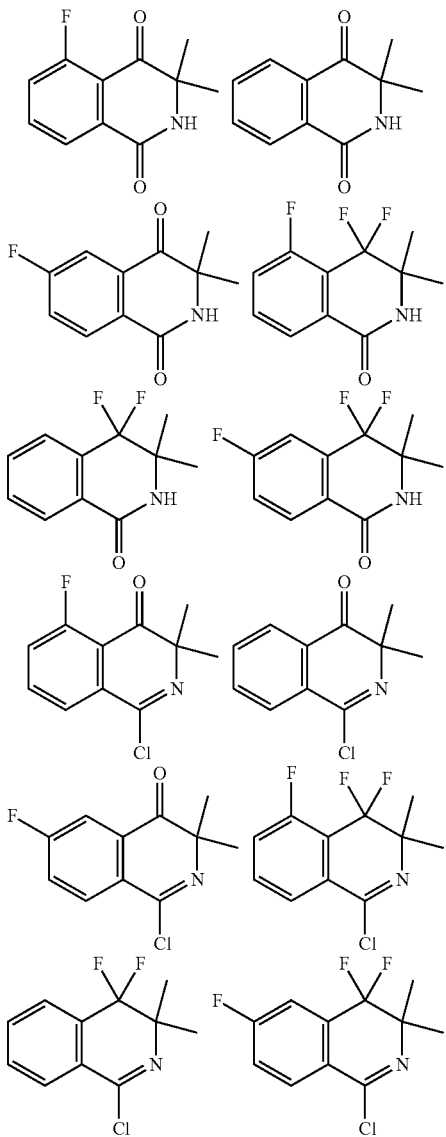

The compounds of formula (I) can be used in the agricultural sector and related fields of use e.g. as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (for example rice), for the protection against fungal infections as well as against phytopathogenic fungi occurring in the soil. The propagation material can be treated with a composition comprising a compound of formula (I) before planting: seed, for example, can be dressed before being sown. The compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore the compounds according to present invention can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

Compounds of formula (I) and fungicidal compositions containing them may be used to control plant diseases caused by a broad spectrum of fungal plant pathogens. They are effective in controlling a broad spectrum of plant diseases, such as foliar pathogens of ornamental, turf, vegetable, field, cereal, and fruit crops.

These fungi and fungal vectors of disease, as well as phytopathogenic bacteria and viruses, which may be controlled are for example:

*Absidia corymbifera*, *Alternaria* spp, *Aphanomyces* spp, *Ascochyta* spp, *Aspergillus* spp. including *A. flavus*, *A. fumigatus*, *A. nidulans*, *A. niger*, *A. terrus*, *Aureobasidium* spp. including *A. pullulans*, *Blastomyces dermatitidis*, *Blumeria graminis*, *Bremia lactucae*, *Botryosphaeria* spp. including *B. dothidea*, *B. obtusa*, *Botrytis* spp. inclusing *B. cinerea*, *Candida* spp. including *C. albicans*, *C. glabrata*, *C. krusei*, *C. lusitaniae*, *C. parapsilosis*, *C. tropicalis*, *Cephaloascus fragrans*, *Ceratocystis* spp, *Cercospora* spp. including *C. arachidicola*, *Cercosporidium personatum*, *Cladosporium* spp, *Claviceps purpurea*,

*Coccidioides immitis*, *Cochliobolus* spp, *Colletotrichum* spp. including *C. musae*,

*Cryptococcus neoformans, Diaporthe* spp, *Didymella* spp, *Drechslera* spp, *Elsinoe* spp,

*Epidermophyton* spp, *Erwinia amylovora, Erysiphe* spp. including *E. cichoracearum,*

*Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi,*

*Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp, *Stereum hirsutum, Thanatephorus cucumeris, Thielaviopsis basicola, Tilletia* spp, *Trichoderma* spp. including *T. harzianum, T. pseudokoningii, T. viride,*

*Trichophyton* spp, *Typhula* spp, *Uncinula necator, Urocystis* spp, *Ustilago* spp, *Venturia* spp. including *V. inaequalis, Verticillium* spp, and *Xanthomonas* spp.

In particular, compounds of formula (I) and fungicidal compositions containing them may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

These pathogens may include:

Oomycetes, including *Phytophthora* diseases such as those caused by *Phytophthora capsici, Phytophthora infestans, Phytophthora sojae, Phytophthora fragariae, Phytophthora nicotianae, Phytophthora cinnamomi, Phytophthora citricola, Phytophthora citrophthora* and *Phytophthora erythroseptica; Pythium* diseases such as those caused by *Pythium aphanidermatum, Pythium arrhenomanes, Pythium graminicola, Pythium irregulare* and *Pythium ultimum*; diseases caused by Peronosporales such as *Peronospora destructor, Peronospora parasitica, Plasmopara viticola, Plasmopara halstedii, Pseudoperonospora cubensis, Albugo candida, Sclerophthora macrospora* and *Bremia lactucae*; and others such as *Aphanomyces cochlioides, Labyrinthula zosterae, Peronosclerospora sorghi* and *Sclerospora graminicola.*

Ascomycetes, including blotch, spot, blast or blight diseases and/or rots for example those caused by Pleosporales such as *Stemphylium solani, Stagonospora tainanensis, Spilocaea oleaginea, Setosphaeria turcica, Pyrenochaeta lycoperisici, Pleospora herbarum, Phoma destructiva, Phaeosphaeria herpotrichoides, Phaeocryptocus gaeumannii, Ophiosphaerella graminicola, Ophiobolus graminis, Leptosphaeria maculans, Hendersonia creberrima, Helminthosporium triticirepentis, Setosphaeria turcica, Drechslera glycines, Didymella bryoniae, Cycloconium oleagineum, Corynespora cassiicola, Cochliobolus sativus, Bipolaris cactivora, Venturia inaequalis, Pyrenophora teres, Pyrenophora tritici-repentis, Alternaria alternata, Alternaria brassicicola, Alternaria solani* and *Alternaria tomatophila,* Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycovellosiella koepkeii, Phaeoisariopsis bataticola, Pseudocercospora vitis, Pseudocercosporella herpotrichoides, Ramularia beticola, Ramularia collo-cygni,* Magnaporthales such as *Gaeumannomyces graminis, Magnaporthe grisea, Pyricularia oryzae,* Diaporthales such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma*, and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petrieffidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor, Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis*; powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia gut-*

*tata* and *Oidium arachidis*; molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum*; anthracnoses for example those caused by Glommerelales such as *Colletotrichum gloeosporioides, Colletotrichum lagenarium, Colletotrichum gossypii, Glomerella cingulata*, and *Colletotrichum graminicola*; and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f.sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum*, and *Verticillium theobromae*.

Basidiomycetes, including smuts for example those caused by Ustilaginales such as *Ustilaginoidea virens, Ustilago nuda, Ustilago tritici, Ustilago zeae*, rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f.sp. *Hordei, Puccinia striiformis* f.sp. *Secalis, Pucciniastrum coryli*, or Uredinales such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries*.

Blastocladiomycetes, such as *Physoderma maydis*.

Mucoromycetes, such as *Choanephora cucurbitarum; Mucor* spp.; *Rhizopus arrhizus*, As well as diseases caused by other species and genera closely related to those listed above.

In addition to their fungicidal activity, the compounds and compositions comprising them may also have activity against bacteria such as *Erwinia amylovora, Erwinia caratovora, Xanthomonas campestris, Pseudomonas syringae, Streptomyces* scabies and other related species as well as certain protozoa.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The useful plants and/or target crops in accordance with the invention include conventional as well as genetically enhanced or engineered varieties such as, for example, insect resistant (e.g. Bt. and VIP varieties) as well as disease resistant, herbicide tolerant (e.g. glyphosate- and glufosinate-resistant maize varieties commercially available under the trade names RoundupReady® and LibertyLink®) and nematode tolerant varieties. By way of example, suitable genetically enhanced or engineered crop varieties include the Stoneville 5599BR cotton and Stoneville 4892BR cotton varieties.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi. An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Toxins that can be expressed by transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1 Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO03/018810).

More examples of such toxins or transgenic plants capable of synthesising such toxins are disclosed, for example, in EP-A-0 374 753, WO93/07278, WO95/34656, EP-A-0 427 529, EP-A-451 878 and WO03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603 MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

Normally, in the management of a crop a grower would use one or more other agronomic chemicals in addition to the compound of the present invention. Examples of agronomic chemicals include pesticides, such as acaricides, bactericides, fungicides, herbicides, insecticides, nematicides, as well as plant nutrients and plant fertilizers.

Accordingly, the present invention provides a composition comprising a compound of formula (I) according to the present invention together with one or more pesticides, plant nutrients or plant fertilizers. The combination may also encompass specific plant traits incorporated into the plant using any means, for example conventional breeding or genetic modification. Such compositions may also contain one or more inert carriers as described above.

The invention also provides for the use of a composition comprising a compound of formula (I) according to the present invention together with one or more pesticides, plant nutrients or plant fertilizers. The combination may also encompass specific plant traits incorporated into the plant using any means, for example conventional breeding or genetic modification.

Suitable examples of plant nutrients or plant fertilizers are calcium sulfate ($CaSO_4$), calcium nitrate ($Ca(NO_3)_2.4H_2O$), calcium carbonate ($CaCO_3$), potassium nitrate ($KNO_3$), magnesium sulfate ($MgSO_4$), potassium hydrogen phosphate ($KH_2PO_4$), manganese sulfate ($MnSO_4$), copper sulfate ($CuSO_4$), zinc sulfate ($ZnSO_4$), nickel chloride ($NiCl_2$), cobalt sulfate ($CoSO_4$), potassium hydroxide (KOH), sodium chloride (NaCl), boric acid ($H_3BO_3$) and metal salts thereof ($Na_2MoO_4$). The nutrients may be present in an amount of 5% to 50% by weight, preferably of 10% to 25% by weight or of 15% to 20% by weight each. Preferred additional nutrients are urea (($NH_2)_2CO$), melamine ($C_3H_6N_6$), potassium oxide ($K_2O$), and inorganic nitrates. The most preferred additional plant nutrient is potassium oxide. Where the preferred additional nutrient is urea, it is present in an amount of generally 1% to 20% by weight, preferably 2% to 10% by weight or of 3% to 7% by weight.

Suitable examples of pesticides are acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, zinc fungicides, Benzoylureas, carbamates, chloronicotinyls, diacylhydrazines, diamides, fiproles, macrolides, nitroimines, nitromethylenes, organochlorines, organophosphates, organosilicons, organotins, phenylpyrazoles, phosphoric esters, pyrethroids, spinosyns, tetramic acid derivatives, tetronic acid derivatives, Antibiotic nematicides, avermectin nematicides, botanical nematicides, carbamate nematicides, oxime carbamate nematicides, organophosphorus nematicides, nematophagous fungi or bacteria, amide herbicides, anilide herbicides, arsenical herbicides, arylalanine herbicides, aryloxyphenoxypropionic herbicides, benzofuranyl herbicides, benzoic acid herbicides, benzothiazole herbicides, benzoylcyclohexanedione herbicides, carbamate herbicides, carbanilate herbicides, chloroacetanilide herbicides, chlorotriazine herbicides, cyclohexene oxmie herbicides, cyclopropylisoxazole herbicides, dicarboximide herbicides, dinitroaniline herbicides, dinitrophenol herbicides, diphenyl ether herbicides, dithiocarbamate herbicides, fluoroalkyltriazine herbicides, halogenated aliphatic herbicides, imidazolinone herbicides, inorganic herbicides, methoxytriazine herbicides, methylthiotriazine herbicides, nitrile herbicides, nitrophenyl ether herbicides, organophosphorous herbicides, oxadiazolone herbicides, oxazole herbicides, phenoxy herbicides, phenoxyacetic herbicides, phenoxybutyric herbicides, phenoxypropionic herbicides, phenylenediamine herbicides, phenylurea herbicides, phthalic acid herbicides, picolinic acid herbicides, pyrazole herbicides, pyridazine herbicides, pyridazinone herbicides, pyridine herbicides, pyrimidinediamine herbicides, pyrimidinyloxybenzylamine herbicides, pyrimidinylsulfonylurea herbicides, quaternary ammonium herbicides, quinolinecarboxylic acid herbicides, sulfonamide herbicides, sulfonanilide herbicides, sulfonylurea herbicides, thiadiazolylurea herbicides, thioamide herbicides, thiocarbamate herbicides, thiocarbonate herbicides, thiourea herbicides, triazine herbicides, triazinone herbicides, triazinylsulfonylurea herbicides, triazole herbicides, triazolone herbicides, triazolopyrimidine herbicides, uracil herbicides, urea herbicides, microbials, plant extracts, pheromones, macrobials and other biologicals.

A further aspect of invention is related to a method of controlling or preventing an infestation of plants, e.g. useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is preferably 1 g to 2000 g of active ingredient per hectare, more preferably 10 to 1000 g/ha, most preferably 10 to 600 g/ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, δ ppm, 3 ppm, 1.5 ppm, 0.8 ppm or 0.2 ppm.

Throughout this description, temperatures are given in degrees Celsius and "m.p." means melting point. LC/MS means Liquid Chromatography Mass Spectroscopy and the description of the apparatus and the methods are:

Method G:

Spectra were recorded on a Mass Spectrometer (ACQUITY UPLC) from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

Method H:

Spectra were recorded on a Mass Spectrometer (ACQUITY UPLC) from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (ml/min) 0.85

FORMULATION EXAMPLES

| Wettable powders | a) | b) | c) |
| --- | --- | --- | --- |
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

Emulsifiable Concentrate

| active ingredient [compound of formula (I)] | 10% |
|---|---|
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| Active ingredient [compound of formula (I)] | 15% |
|---|---|
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| Active ingredient [compound of formula (I)] | 8% |
|---|---|
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| active ingredient [compound of formula (I)] | 40% |
|---|---|
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredient [compound of formula (I)] | 40% |
|---|---|
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

PREPARATION EXAMPLES

Using the techniques described both above and below compounds of formula (I) may be prepared.

Example 1: This Example Illustrates the Preparation of 5-fluoro-1-[8-fluoroimidazo(1,2-a)pyrimidin-3-yl]-3,3,4,4-tetramethyl-isoquinoline Step 1: N'-(3-fluoro-2-pyridyl)-N,N-dimethyl-formamidine 1.50 g (13.4 mmol) 2-amino-3-fluoro-pyridine and 1.99 g (16.2 mmol) N,N-dimethylformamide dimethylacetal in 15 ml methanol were heated under reflux during 2 h. The reaction mixture was concentrated under reduced pressure and the residue was purified by flash chromatography (heptane/ethylacetate=1:1) to give N'-(3-fluoro-2-pyridyl)-N,N-dimethyl-formamidine as a colourless oil.

Step 2: 8-fluoroimidazo(1,2-a)pyrimidin-3-carbonitrile

To 2.11 g (12.6 mmol) N'-(3-fluoro-2-pyridyl)-N,N-dimethyl-formamidine in 30 ml isopropanol was added 1.54 g (18.3 mmol) sodium bicarbonate and 1.1 ml (14.9 mmol) bromoacetonitrile and the mixture was stirred at 80° C. overnight. The reaction mixture was concentrated, extracted with water/ethylacetate, dried over sodium sulfate and concentrated under reduced pressure. The residue was purified by flash chromatography (heptane/ethylacetate=1:1) to give 8-fluoroimidazo(1,2-a)pyrimidin-3-carbonitrile as an oil, which crystallised from tert-butylmethylether/heptane (1:2) as a beige powder, m.p. 157-158° C.

Step 3: 5-fluoro-1-(8-fluoroimidazo(1,2-a)pyrimidin-3-yl)-3,3,4,4-tetramethyl-isoquinoline To a cooled suspension (0° C.) of 0.13 g (0.80 mmol) 8-fluoroimidazo(1,2-a)pyrimidin-3-carbonitrile in 1.8 ml conc. sulfuric acid, 0.17 g (0.89 mmol) 3-(2-fluorophenyl)-2,3-dimethyl-butan-2-ol was added within 20 min. and the mixture was stirred for 1 h at this temperature. The reaction mixture was poured into ice-water and the pH was adjusted to 8 using sodium hydroxide. The aqueous phase was extracted with ethylacetate, dried over sodium sulfate and concentrated under reduced pressure. The residue was purified by flash chromatography (heptane/ethylacetate=4:1) to give 5-fluoro-1-(8-fluoroimidazo(1,2-a)pyrimidin-3-yl)-3,3,4,4-tetramethyl-isoquinoline as a beige powder, m.p. 156-157° C.

Preparation of
3-(2-fluorophenyl)-2,3-dimethyl-butan-2-ol

Step 1:
ethyl-2-(2-fluorophenyl)-2-methyl-propanoate

To the suspension of 27.4 g (0.69 mol) sodium hydride in 220 ml tetrahydrofuran was added dropwise a mixture of 50.0 g (0.27 mol) ethyl-2-(2-fluorophenyl)acetate and 117.9 g (0.82 mmol) iodomethane in 60 ml tetrahydrofuran at room temperature. After stirring overnight 70 ml saturated ammoniumchloride solution was slowly added. The reaction mixture was poured into 300 ml ice-water and extracted with ethylacetate, dried over sodium sulfate and concentrated under reduced pressure. The residue was purified by flash chromatography (heptane/ethylacetate=19:1) to give ethyl-2-(2-fluorophenyl)-2-methyl-propanoate as a yellowish oil.

Step 2: 3-(2-fluorophenyl)-2,3-dimethyl-butan-2-ol 52.1 g (0.25 mol) ethyl-2-(2-fluorophenyl)-2-methyl-propanoate and 207 ml (0.12 mol) lanthanum(III) chloride bis(lithium chloride) complex solution (0.6 M in THF) were stirred for 1.5 h at room temperature. Then 248 ml (0.74 mol) methylmagnesium bromide solution (3.0 M in diethyl ether) was added dropwise at 0° C. After stirring overnight at room temperature 60 ml saturated ammoniumchloride solution was slowly added under cooling. 200 ml water was added and stirring continued for 30 min. The reaction mixture was extracted with tert-butyl methylether, filtered over Celite, the phases separated and the waterphase extracted with tert-butyl methylether. The organic phases were washed with brine, dried over sodium sulfate and concentrated under reduced pressure to give 3-(2-fluorophenyl)-2,3-dimethyl-butan-2-ol as a yellowish solid, m.p. 42-43° C.

Example 2: This Example Illustrates the Preparation of 5-fluoro-3,3,4,4-tetramethyl-1-pyrazolo[1,5-a]pyridin-3-yl-isoquinoline Step 1: pyrazolo[1,5-a]pyridine-3-carbonitrile To a solution of 0.2 g (0.8967 mmol) pyridin-1-ium-1-amine hydroiodide and 0.18 g (1.3003 mmol) potassium carbonate in 2 mL N,N-dimethylformamide, 0.085 mL (0.9869 mmol, 0.082 g) (E)-3-methoxyprop-2-enenitrile at room temperature were added dropwise. The reaction mixture was stirred over night at 80° C. The reaction mixture was concentrated under reduced pressure and the residue was extracted with diethylether/water. The combined organic phase was washed with brine, dried with sodium sulfate, filtered and concentrated under reduced pressure. The residue was purified by flash chromatography (cyclohexane/ethyl acetate=1:1) to give 0.07 g (0.489 mmol) pyrazolo[1,5-a]pyridine-3-carbonitrile as beige solid, m.p. 124-127° C.

Step 2: 5-fluoro-3,3,4,4-tetramethyl-1-pyrazolo[1,5-a]pyridin-3-yl-isoquinoline

To a solution of 0.07 g (0.489 mmol) pyrazolo[1,5-a]pyridine-3-carbonitrile in 0.8 mL sulfuric acid 0.115 g (0.5868 mmol) 3-(2-fluorophenyl)-2,3-dimethyl-butan-2-ol was added dropwise at 0° C. The reaction mixture was stirred at 0° C. for three hours then it was poured on cold water, basified with 8M NaOH to pH 10 and washed three times with dichloromethane. The organic phase was washed with brine, dried over sodium sulfate, filtered and concentrated under reduced pressure. The residue was purified by flash chromatography (cyclohexane/ethyl acetate=3:1) to give 0.0573 g (0.169 mmol) 5-fluoro-3,3,4,4-tetramethyl-1-pyrazolo[1,5-a]pyridin-3-yl-isoquinoline as beige solid, m.p. 105-108° C.

Example 3: This Example Illustrates the Preparation of 4,4-difluoro-3,3-dimethyl-1-(8-methylimidazo[1,2-a]pyridin-3-yl)isoquinoline Step 1: 1-(8-bromoimidazo[1,2-a]pyridin-3-yl)-3,3-dimethyl-4H-isoquinoline To an ice cooled (0° C.) solution of 1.00 g (4.50 mmol) 8-bromoimidazo[1,2-a]pyridine-3-carbonitrile in 9.8 mL conc. sulfuric acid was slowly added 1.01 g (6.76 mmol) 2-methyl-1-phenyl-propan-2-ol over 15 min and the resulting solution was stirred for additional 60 min at 0-5° C. The reaction mixture was poured into ice-water and the pH was adjusted to 9 with 4 N sodium hydroxide solution. The aqueous phase was extracted with ethyl acetate, dried over sodium sulfate, filtrated and concentrated under reduced pressure. The residue was purified by flash chromatography (heptane/ethyl acetate=3:1) to give 1.04 g (2.94 mmol) 1-(8-bromoimidazo[1,2-a]pyridin-3-yl)-3,3-dimethyl-4H-isoquinoline as light yellow powder.

Step 2: 1-(8-bromoimidazo[1,2-a]pyridin-3-yl)-3,3-dimethyl-isoquinolin-4-one

To a solution of 0.625 g (1.77 mmol) 1-(8-bromoimidazo[1,2-a]pyridin-3-yl)-3,3-dimethyl-4H-isoquinoline in 50 mL carbon tetrachloride was added 0.661 g (3.52 mmol) N-bromosuccinimide and 0.076 g (0.44 mmol) azoisobutyronitrile at RT. The resulting mixture was warmed to 77° C. and stirred for 120 min at this temperature. After cooling to RT, the reaction was diluted with dichloromethane, successively washed with water and brine, dried over sodium sulfate, filtrated and concentrated under reduced pressure. The residue was purified by flash chromatography (heptane/ethyl acetate=2:1) to give 0.634 g (1.73 mmol) 1-(8-bromoimidazo[1,2-a]pyridin-3-yl)-3,3-dimethyl-isoquinolin-4-one as off-white solid, m.p. 204-208° C.

Step 3: 1-(8-bromoimidazo[1,2-a]pyridin-3-yl)-4,4-difluoro-3,3-dimethyl-isoquinoline 0.33 g (0.81 mmol) 1-(8-bromoimidazo[1,2-a]pyridin-3-yl)-3,3-dimethyl-isoquinolin-4-one was suspended in 0.51 mL 2,2-difluoro-1,3-dimethylimidazoline at RT, warmed to 100° C. and stirred over night at this temperature. The resulting solution was cooled to RT and slowly added into ice-cold, saturated bicarbonate solution. This mixture was extracted with ethyl acetate; the organic layer was washed with brine, dried over sodium sulfate, filtrated and concentrated under reduced pressure. The residue was purified by flash chromatography (toluene/ethyl acetate=1:0-9:1) to afford 0.136 g (0.35 mmol) 1-(8-bromoimidazo[1,2-a]pyridin-3-yl)-4,4-difluoro-3,3-dimethyl-isoquinoline as white solid, m.p. 173° C.

Step 4: 4,4-difluoro-3,3-dimethyl-1-(8-methylimidazo[1,2-a]pyridin-3-yl)isoquinoline To a solution of 0.09 g (0.23 mmol) 1-(8-bromoimidazo[1,2-a]pyridin-3-yl)-4,4-difluoro-3,3-dimethyl-isoquinoline in 3 mL dioxane (degassed) was added 0.072 mL (0.25 mmol) trimethylboroxine (3.5 M in THF), 0.307 g (0.92 mmol) cesium carbonate and 0.020 g (0.02 mmol) [Pd(dppf)Cl2] at RT. The resulting suspension was warmed to 95° C. and maintained for 90 min at this temperature. After cooling to RT, the reaction was diluted with water and extracted with ethyl acetate. The organic layer was washed with brine, dried over sodium sulfate, filtrated and concentrated under reduced pressure. The residue was purified by flash chromatography (heptane/ethyl acetate=3:2-2:1) to afford 0.073 g (0.22 mmol) 4,4-difluoro-3,3-dimethyl-1-(8-methylimidazo[1,2-a]pyridin-3-yl)isoquinoline as light brown oil.

Example 4: This Example Illustrates the Preparation of 1-(6,7-dimethylpyrazolo[1,5-a]pyridin-3-yl)-4,4-difluoro-3,3-dimethyl-isoquinoline Step 1: Preparation of 3,3-dimethyl-2H-isoquinoline-1,4-dione 1) To a solution of 3,3-dimethyl-2,4-dihydroisoquinolin-1-one (57.1 mmol, 10.0 g) in 0014 (285 mL) at room temperature was added N-bromosuccinimide (171 mmol, 30.5 g) and AIBN (8.5 mmol, 1.43 g) and the reaction mixture was stirred at 70° C. for 3 hours. The reaction mixture was allowed to cool down to room temperature, concentrated under vacuo and diluted with EtOAc, washed with water and brine, dried over Na2SO4, filtered and concentrated to give 4,4-dibromo-3,3-dimethyl-2H-isoquinolin-1-one (25.2 g) as a light yellow solid which was used directly in the next step without further purification: LC-MS (Method H) UV Detection: 220 nm, Rt=1.34; MS: (M+1)=332-334-336; $^1$H NMR (400 MHz, CHLOROFORM-d) δ ppm 1.57 (s, 6H) 7.21 (br. s, 1H) 7.70-7.77 (m, 1H) 7.78-7.85 (m, 1H) 8.06-8.14 (m, 1H) 8.23-8.30 (m, 1H).

2) To a solution of 4,4-dibromo-3,3-dimethyl-2H-isoquinolin-1-one (20.0 g) in a mixture of water (450 mL) and tetrahydrofuran (225 mL) was added sodium carbonate (135 mmol, 14.3 g) and the mixture was stirred at room temperature for 12 h and at 70° C. for 4 h 30 min. The reaction mixture was allowed to cool down to room temperature, diluted with water, acidified to pH 3-4 with 90 mL of a 2 M solution of hydrochloric acid and extracted with dichloromethane. The combined organic extracts were dried over Na2SO4, filtered and concentrated to give 3,3-dimethyl-2H-isoquinoline-1,4-dione (9.95 g) as a yellow solid: LC-MS (Method H) UV Detection: 220 nm, Rt=0.81; MS: (M+1)=190; $^1$H NMR (400 MHz, CHLOROFORM-d) δ ppm 1.77 (s, 3H) 1.97 (s, 3H) 7.39 (s, 1H) 7.46-7.58 (m, 1H) 7.60-7.71 (m, 1H) 7.98-8.22 (m, 2H).

Step 2: Preparation of 1-chloro-3,3-dimethyl-isoquinolin-4-one

To a solution of N,N-dimethylformamide (2.3 mL, 30 mmol) in dichloromethane (52 mL) at room temperature was added oxalyl chloride (20 mmol, 1.8 mL) dropwise over a period of 35 min and the white suspension was vigorously stirred for 15 min until the gas evolution stopped. A solution of 3,3-dimethyl-2H-isoquinoline-1,4-dione (2.5 g, 13 mmol) in dichloromethane (25 mL) was then added dropwise and the mixture was stirred at room temperature for 1 h. The reaction mixture was poured into an ice-cooled mixture of saturated aqueous NaHCO$_3$ solution and pentane, and the organic phase was separated. The aqueous phase was then extracted with pentane, and the combined organic phases were washed with brine, dried over Na$_2$SO$_4$, filtered and concentrated to give 1-chloro-3,3-dimethyl-isoquinolin-4-one (2.5 g) as a yellow solid: LC-MS (Method H) UV Detection: 220 nm, Rt=1.34; MS: (M+1)=208-210; $^1$H NMR (400 MHz, CHLOROFORM-d) δ ppm 1.47 (s, 6H) 7.62-7.69 (m, 1H) 7.73-7.81 (m, 1H) 7.90 (dd, J=8.07, 0.73 Hz, 1H) 8.04 (dd, J=7.50, 0.90 Hz, 1H).

Step 3: Preparation of 3,3-dimethyl-1-(2-trimethylsilylethynyl)isoquinolin-4-one To a solution of 1-chloro-3,3-dimethyl-isoquinolin-4-one (2.10 g, 9.1 mmol) in triethylamine (20 mL) was added at room temperature CuI (0.17 g, 0.9 mmol), bis-triphenylphosphine Palladium(II) dichloride (320 mg, 0.46 mmol) followed by dropwise addition of ethynyltrimethylsilane (1.9 mL, 14 mmol). The black solution was stirred at room temperature for 1 hour. The reaction mixture was quenched with saturated aqueous NH$_4$Cl and the extracted twice with ethyl acetate. The organic phase was washed with brine, dried over anhydrous Na$_2$SO$_4$, filtered and concentrated. Purification by flash chromatography gave 3,3-dimethyl-1-(2-trimethylsilylethynyl)isoquinolin-4-one (2.35 g) as a dark yellow oil: LC-MS (Method G), Rt=1.21 UV Detection: 220 nm; MS: (M+1)=270; $^1$H NMR (400 MHz, CHLOROFORM-d) δ ppm 0.32 (s, 9H) 1.51 (s, 6H) 7.63-7.69 (m, 1H) 7.79-7.83 (m, 1H) 7.98 (dd, 2H) 8.05 (dd, 1H).

Step 4: Preparation of 1-ethynyl-3,3-dimethyl-isoquinolin-4-one

To a solution of 3,3-dimethyl-1-(2-trimethylsilylethynyl)isoquinolin-4-one (1.0 g, 3.7 mmol) in methanol (7.5 mL) was added at room temperature K$_2$CO$_3$ (570 mg, 4.1 mmol). The reaction mixture was stirred at room temperature for 1 h, quenched with water (pH 8/9), and extracted twice with ethyl acetate. The combined organic phases were washed with brine, dried over anhydrous Na$_2$SO$_4$, filtered and concentrated. Purification by flash chromatography gave 1-ethynyl-3,3-dimethyl-isoquinolin-4-one (700 mg) as a brown oil: LC-MS (Method G), Rt=0.84, UV Detection: 220 nm; MS: (M+1)=198; $^1$H NMR (400 MHz, CHLORO- FORM-d) δ ppm 1.50 (s, 6H) 3.28 (s, 1H) 7.65-7.70 (m, 1H) 7.79-7.85 (m, 1H) 7.98-8.04 (m, 1H) 8.06-8.12 (s, 1H).

Step 5: Preparation of 1-(6,7-dimethylpyrazolo[1,5-a]pyridin-3-yl)-3,3-dimethyl-isoquinolin-4-one To a white suspension of 2,3-dimethylpyridin-1-ium-1-amine iodide (1.0 g, 4.1 mmol) in dichloromethane (20 mL) was added diazabicycleundecene (623 mg, 4.1 mmol) followed by dropwise addition of 1-ethynyl-3,3-dimethyl-isoquinolin-4-one (700 mg, 3.2 mmol) dissolved in dichloromethane (10 mL), over a period of 30 min. The resulting brown mixture was stirred at room temperature for 1 hour, till disappearance of the 1-ethynyl-3,3-dimethyl-isoquinolin-4-one starting material. The reaction mixture was quenched with water, the organic phase was separated and washed with saturated aqueous $NH_4Cl$. The water phase was extracted with dichloromethane. The combined organic phases were washed with water and brine, dried over anhydrous $Na_2SO_4$, filtered and concentrated. Purification by flash chromatography gave 1-(6,7-dimethylpyrazolo[1,5-a]pyridin-3-yl)-3,3-dimethyl-isoquinolin-4-one (410 mg) as orange solid: mp=152°-153° C., LC-MS (Method G), Rt=0.86, UV Detection: 220 nm; MS: (M+1)=318; $^1$H NMR (400 MHz, CHLOROFORM-d) δ ppm 1.57 (s, 6H) 2.42 (s, 3H) 2.72 (s, 3H) 7.15 (d, 1H) 7.62-7.85 (m, 3H) 8.15 (d, 1H) 8.35 (s, 1H).

Step 6: Preparation of 1-(6,7-dimethylpyrazolo[1,5-a]pyridin-3-yl)-4,4-difluoro-3,3-dimethyl-isoquinoline A solution of 1-(6,7-dimethylpyrazolo[1,5-a]pyridin-3-yl)-3,3-dimethyl-isoquinolin-4-one (370 mg, 1.2 mmol) in 2,2-difluoro-1,3-dimethylimidazolidine (14 mmol, 1.8 ml) was stirred at 105° C. for 24 hours. The reaction mixture was allowed to cool down to room temperature, diluted with dichloromethane then quenched by slow addition to an ice cooled saturated aqueous $NaHCO_3$ solution. The 2 phases were separated, and the aqueous phase was extracted with DCM. The combined organic phases were washed with brine, dried over $Na_2SO_4$, filtered and concentrated. The residue was purified by flash chromatography to give 1-(6,7-dimethylpyrazolo[1,5-a]pyridin-3-yl)-4,4-difluoro-3,3-dimethyl-isoquinoline (328 mg) as a beige solid: mp=160-161° C., LC-MS (Method G) UV Detection: 220 nm, Rt=1.03, MS: (M+1)=340; $^1$H NMR (400 MHz, CHLOROFORM-d) δ ppm 1.42 (s, 6H) 2.40 (s, 3H) 2.79 (s, 3H) 7.15 (d, 1H) 7.57-7.68 (m, 2H) 7.72 (d, 1H) 7.85 (d, 1H) 7.94 (d, 1H) 8.21 (s, 1H). $^{19}$F NMR (400 MHz, CHLOROFORM-d) δ ppm −112.

Example 5: This Example Illustrate the Preparation of 1-(6,7-dimethylpyrazolo[1,5-a]pyridin-3-yl)-4,4,6-trifluoro-3,3-dimethyl-isoquinoline Step 1: Preparation of 6-fluoro-3,3-dimethyl-2H-isoquinoline-1,4-dione Preparation was performed via an analogous synthetic route to that described for 3,3-dimethyl-2H-isoquinoline-1,4-dione 6-fluoro-3,3-dimethyl-2H-isoquinoline-1,4-dione (example 4, step 1):
LC-MS (Method H) UV Detection: 220 nm, Rt=0.94; MS: (M+1)=208; 1H NMR (400 MHz, CHLOROFORM-d) δ ppm 1.56 (s, 6H) 7.35 (br. s, 1H) 7.43-7.50 (m, 1H) 7.68-7.74 (m, 1H) 8.25-8.30 (m, 1H). 19F (400 MHz, CHLOROFORM-d) δ ppm −103

Step 2: Preparation of 1-chloro-6-fluoro-3,3-dimethyl-isoquinolin-4-one

To a solution of N,N-dimethylformamide (1.6 mL, 21 mmol) in dichloromethane (36 mL) at room temperature was added oxalyl chloride (14 mmol, 1.6 mL) dropwise over a period of 30 min and the white suspension was vigorously stirred for 25 min until the gas evolution stopped. A solution of 6-fluoro-3,3-dimethyl-2H-isoquinoline-1,4-dione (2.0 g, 9.7 mmol) in dichloromethane (20 mL) was then added dropwise at 0° C. The mixture was allowed to warm to ambient temperature and stirred for 1 hour. The reaction mixture was poured into an ice-cooled mixture of saturated aqueous $NaHCO_3$ solution and pentane, and the organic phase was separated. The aqueous phase was then extracted with pentane, and the combined organic phases were washed with brine, dried over $Na_2SO_4$, filtered and concentrated to give 1-chloro-6-fluoro-3,3-dimethyl-isoquinolin-4-one (1.95 g) as a dark yellow oil, that was used without purification in the next synthetic step: LC-MS (Method H) UV Detection: 220 nm, Rt=1.42; MS: (M+1)=226-228

Step 3: Preparation of 6-fluoro-3,3-dimethyl-1-(2-trimethylsilylethynyl)isoquinolin-4-one To a solution of 1-chloro-6-fluoro-3,3-dimethyl-isoquinolin-4-one (1.4 g, 6.0 mmol) in triethylamine (12 mL) was added at room temperature CuI (116 mg, 0.6 mmol), bis-triphenylphosphine Palladium(II) dichloride (214 mg, 0.3 mmol) followed by dropwise addition of ethynyltrimethylsilane (1.3 mL, 9.1 mmol). The black solution was stirred at room temperature overnight. The reaction mixture was quenched with saturated aqueous $NH_4Cl$ and the extracted twice with ethyl acetate. The organic phase was washed with brine, dried over anhydrous $Na_2SO_4$, filtered and concentrated. Purification by flash chromatography gave 6-fluoro-3,3-dimethyl-1-(2-trimethylsilylethynyl)isoquinolin-4-one (1.25 g) as a orange solid: LC-MS (Method G), Rt=1.22 UV Detection: 220 nm; MS: (M+1)=288; $^1$H NMR (400 MHz, CHLOROFORM-d) δ ppm 0.32 (s, 9H) 1.52 (s, 6H) 7.47-7.52 (m, 1H) 7.70-7.76 (m, 1H) 8.0-8.05 (m, 1H). $^{19}$F (400 MHz, CHLOROFORM-d) δ ppm −104.

Step 4: Preparation of 1-ethynyl-6-fluoro-3,3-dimethyl-isoquinolin-4-one

To a solution of 6-fluoro-3,3-dimethyl-1-(2-trimethylsilylethynyl)isoquinolin-4-one (1.25, 4.3 mmol) in dichloromethane (17 mL) was added at room temperature potassium fluoride (0.56 g, 9.6 mmol) and 18-crown-6 (1.2 g, 4.3 mmol). The reaction mixture was stirred at room temperature for 30 min, quenched with saturated aqueous $NaHCO_3$, and extracted twice with dichloromethane. The combined organic phases were washed with brine, dried over anhydrous $Na_2SO_4$, filtered and concentrated. Purification by flash chromatography gave 1-ethynyl-6-fluoro-3,3-dimethyl-isoquinolin-4-one. (610 mg) as a brown oil: LC-MS (Method G), Rt=0.90, UV Detection: 220 nm; MS: (M+1)=216; $^1$H NMR (400 MHz, CHLOROFORM-d) δ ppm 1.53 (s, 6H) 3.31 (s, 1H) 7.46-7.52 (m, 1H) 7.70-7.75 (m, 1H) 8.02-8.07 (m, 1H). $^{19}$F (400 MHz, CHLOROFORM-d) δ ppm −103

Step 5: Preparation of 1-(6,7-dimethylpyrazolo[1,5-a]pyridin-3-yl)-6-fluoro-3,3-dimethyl-isoquinolin-4-one To a solution of 2,3-dimethylpyridin-1-ium-1-amine 2,4,6-trimethylbenzenesulfonate (750 mg, 2.3 mmol) in dimethylformamide (8 mL) was first added potassium carbonate (490 mg, 3.5 mmol) followed by dropwise addition of 1-ethynyl-6-fluoro-3,3-dimethyl-isoquinolin-4-one (600 mg, 2.8 mmol) dissolved in dimethylformamide (4 mL), over a period of 30 min. The resulting brown mixture was stirred at room temperature for 2 days, till disappearance of the 1-ethynyl-5-fluoro-3,3-dimethyl-isoquinolin-4-one starting material. The reaction mixture was quenched with water, and extracted twice with ethyl acetate. The combined organic phases were washed with water and brine, dried over anhydrous $Na_2SO_4$, filtered and concentrated. Purification by flash chromatography gave 1-(6,7-dimethylpyrazolo[1,5-a]pyridin-3-yl)-6-fluoro-3,3-dimethyl-isoquinolin-4-one (295 mg) as a brown solid: mp=168-170° C., LC-MS (Method G), Rt=0.92, UV Detection: 220 nm; MS: (M+1)=336; $^1$H NMR (400 MHz, CHLOROFORM-d) δ ppm 1.60 (s, 6H) 2.45 (s, 3H) 2.80 (s, 3H) 7.18 (d, 1H) 7.39-7.48 (m, 1H) 7.73-7.95 (m, 3H) 8.23 (br s, 1H). $^{19}$F NMR (400 MHz, CHLOROFORM-d) δ ppm −106

Step 6: Preparation of 1-(6,7-dimethylpyrazolo[1,5-a]pyridin-3-yl)-4,4,6-trifluoro-3,3-dimethyl-isoquinoline A solution of 1-(6,7-dimethylpyrazolo[1,5-a]pyridin-3-yl)-6-fluoro-3,3-dimethyl-isoquinolin-4-one (280 mg, 0.84 mmol) in 2,2-difluoro-1,3-dimethylimidazolidine (1.3 ml) was stirred at 105° C. for 24 hours. The reaction mixture was allowed to cool down to room temperature, diluted with dichloromethane then quenched by slow addition to an ice cooled saturated aqueous $NaHCO_3$ solution. The two phases were separated, and the aqueous phase was extracted with DCM. The combined organic phases were washed with brine, dried over $Na_2SO_4$, filtered and concentrated. The residue was purified by flash chromatography to give 1-(6,7-dimethylpyrazolo[1,5-a]pyridin-3-yl)-4,4,6-trifluoro-3,3-dimethyl-isoquinoline (235 mg) as a beige solid: mp=183-185° C., LC-MS (Method G) UV Detection: 220 nm, Rt=1.09, MS: (M+1)=358; $^1$H NMR (400 MHz, CHLOROFORM-d) δ ppm 1.45 (s, 6H) 2.45 (s, 3H) 2.80 (s, 3H) 7.19 (d, 1H) 7.22-7.27 (m, 1H) 7.55 (dd, 1H) 7.72-7.77 (m, 1H) 7.95 (d, 1H) 8.21 (br s, 1H). $^{19}$F NMR (400 MHz, CHLOROFORM-d) δ ppm −106, −113.

Example 6: This example illustrates the 1-(6,7-dimethylpyrazolo[1,5-a]pyridin-3-yl)-4,4,5-trifluoro-3,3-dimethyl-isoquinoline

Step 1: Preparation of 5-fluoro-3,3-dimethyl-2H-isoquinoline-1,4-dione

1) To a solution of 5-fluoro-3,3-dimethyl-2,4-dihydroisoquinolin-1-one (5.0 g, 25.9 mmol) in 0014 (100 mL) at room temperature was added N-bromosuccinimide (44 mmol, 7.9 g) and AIBN (2.6 mmol, 0.43 g) and the reaction mixture was stirred at 70° C. for 2 hours, until starting material has disappeared. The reaction mixture was allowed to cool down to room temperature, concentrated under vacuo and diluted with ethyl acetate, washed with water and brine, dried over $Na_2SO_4$, filtered and concentrated to give 4-bromo-5-fluoro-3,3-dimethyl-2,4-dihydroisoquinolin-1-one (6.6 g) as a light yellow solid which was used directly in the next step without further purification: LC-MS (Method G) UV Detection: 220 nm, Rt=0.83; MS: (M+1)=272-274; $^1$H NMR (400 MHz, CHLOROFORM-d) δ ppm 1.30 (s, 3H) 1.55 (s, 3H) 5.30 (s, 1H) 6.15 (br. s, 1H) 7.24-7.30 (m, 1H) 7.40-7.50 (m, 1H) 7.90 (d, 1H). $^{19}$F NMR (400 MHz, CHLOROFORM-d) δ ppm −119

2) A solution of 4-bromo-5-fluoro-3,3-dimethyl-2,4-dihydroisoquinolin-1-one (6.6 g) in a mixture of water (120 mL) and tetrahydrofuran (120 mL) was stirred at 90° C. overnight. The reaction mixture was allowed to cool down to room temperature, diluted with saturated aqueous $NaHCO_3$ to pH 7-8 and extracted with ethyl acetate. The combined organic extracts were dried over Na2SO4, filtered and concentrated. Purification by flash chromatography gave 5-fluoro-4-hydroxy-3,3-dimethyl-2,4-dihydroisoquinolin-1-one (3.54 g) as a white solid:

LC-MS (Method G) UV Detection: 220 nm, Rt=0.60; MS: (M+1)=210; $^1$H NMR (400 MHz, CHLOROFORM-d) δ ppm 1.20 (s, 3H) 1.50 (s, 3H) 2.5 (br. d, 1H) 4.7 (d, 1H) 5.75 (br. s, 1H) 7.27-7.30 (m, 1H) 7.40-7.48 (m, 1H) 7.85 (d, 1H). $^{19}$F NMR (400 MHz, CHLOROFORM-d) δ ppm −113

3) To a solution of 5-fluoro-4-hydroxy-3,3-dimethyl-2,4-dihydroisoquinolin-1-one (3.54 g, 16.9 mmol) in dichloromethane (200 ml) was added Dess-Martin periodinane (18.6 mmol, 8.15 g) at 0° C. The reaction mixture was stirred for 2 hour at temperature between 0 and 10° C. and quenched with saturated aqueous $NaHCO_3$. The organic phase was separated and washed with sodium thiosulfate solution and brine, dried over $Na_2SO_4$ and concentrated under reduced pressure. The residue was purified by flash chromatography to give 5-fluoro-3,3-dimethyl-2H-isoquinoline-1,4-dione (3.08 g) as a white solid: LC-MS (Method G) UV Detection: 220 nm, Rt=0.68; MS: (M+1)=208; $^1$H NMR (400 MHz, CHLOROFORM-d) δ ppm 1.53 (s, 6H) 2.5 (br. d, 1H) 4.7 (d, 1H) 6.52 (br. s, 1H) 7.38-7.43 (m, 1H) 7.72-7.8 (m, 1H) 8.10 (d, 1H).

Step 2: Preparation of 1-chloro-5-fluoro-3,3-dimethyl-isoquinolin-4-one

To a solution of dimethylformamide (1.0 mL, 13.5 mmol) in dichloromethane (25 mL), at room temperature, was added oxalyl chloride (1.2 mL, 13.5 mmol) dropwise over a period of 30 min the white suspension was vigorously stirred at the same temperature for 1 hour until the gas evolution stopped. A solution of 5-fluoro-3,3-dimethyl-2H-isoquinoline-1,4-dione (2.0 g, 9.65 mmol) in dichloromethane (25 mL) was then added dropwise and the mixture was stirred at room temperature for 1 hour. The reaction mixture was poured into an ice-cooled saturated aqueous $NaHCO_3$ solution and pentane, and the organic phase was separated. The aqueous phase was then extracted with pentane, and the combined organic phases were washed with brine, dried over $Na_2SO_4$, filtered and concentrated to give 1-chloro-5-fluoro-3,3-dimethyl-isoquinolin-4-one (2.05 g) as a yellow solid: LC-MS (Method G), Rt=0.91 UV Detection: 220 nm; MS: (M+1)=226-228; $^1$H NMR (400 MHz, CHLOROFORM-d) δ ppm 1.52 (s, 6H) 7.36-7.44 (m, 1H) 7.77-7.81 (m, 2H).

Step 3: Preparation of 5-fluoro-3,3-dimethyl-1-(2-trimethylsilylethynyl)isoquinolin-4-one To a solution of 1-chloro-5-fluoro-3,3-dimethyl-isoquinolin-4-one (2.04 g, 9.0 mmol) in triethylamine (18 mL) was added at room temperature CuI (174 mg, 0.90 mmol), bis-triphenylphosphine Palladium(II) dichloride (0.32 g, 0.45 mmol) followed by dropwise addition of ethynyltrimethylsilane (1.9 mL, 13.6 mmol). The black solution was stirred at room temperature for 1 hour. The reaction mixture was quenched with saturated aqueous $NH_4Cl$ and the extracted twice with ethyl acetate. The organic phase was washed with brine, dried over anhydrous $Na_2SO_4$, filtered and concentrated. Purification by flash chromatography gave 5-fluoro-3,3-dimethyl-1-(2-trimethylsilylethynyl)isoquinolin-4-one (2.25 g) as a yellow solid: LC-MS (Method G), Rt=1.16 UV Detection: 220 nm; MS: (M+1)=288; $^1$H NMR (400 MHz, CHLOROFORM-d) δ ppm 0.30 (s, 9H) 1.51 (s, 6H) 7.29-7.34 (m, 1H) 7.75-7.81 (m, 2H). $^{19}$F (400 MHz, CHLOROFORM-d) δ ppm −108.

Step 4: Preparation of 1-ethynyl-5-fluoro-3,3-dimethyl-isoquinolin-4-one

To a solution of 5-fluoro-3,3-dimethyl-1-(2-trimethylsilylethynyl)isoquinolin-4-one (2.25 g, 7.8 mmol) in dichloromethane (31 mL) was added at room temperature potassium fluoride (2.2 eq, 1.0 g, 17.2 mmol) and 18-crown-6 (2.09 g, 7.8 mmol). The reaction mixture was stirred at room temperature for 30 min, quenched with saturated aqueous $NaHCO_3$, and extracted twice with dichloromethane. The combined organic phases were washed with brine, dried over anhydrous $Na_2SO_4$, filtered and concentrated. Purification by flash chromatography gave 1-ethynyl-5-fluoro-3,3-dimethyl-isoquinolin-4-one (1.46 g) as a yellow solid: LC-MS (Method G), Rt=0.83, UV Detection: 220 nm; MS: (M+1)=216; $^1$H NMR (400 MHz, CHLOROFORM-d) δ ppm 1.50 (s, 6H) 3.28 (s, 1H) 7.32-7.37 (m, 1H) 7.75-7.83 (m, 2H).

Step 5: Preparation of 1-(6,7-dimethylpyrazolo[1,5-a]pyridin-3-yl)-5-fluoro-3,3-dimethyl-isoquinolin-4-one To a solution of 2,3-dimethylpyridin-1-ium-1-amine 2,4,6-trimethylbenzenesulfonate (1.0 g, 3.1 mmol) in dimethylformamide (16 mL) was first added potassium carbonate (650 mg, 4.6 mmol) followed by dropwise addition of 1-ethynyl-5-fluoro-3,3-dimethyl-isoquinolin-4-one (1.0 g, 4.65 mmol) dissolved in dimethylformamide (6 mL), over a period of 30 min. The resulting brown mixture was stirred at room temperature for 16 hours, till disappearance of the 1-ethynyl-5-fluoro-3,3-dimethyl-isoquinolin-4-one starting material. The reaction mixture was quenched with water, and extracted twice with ethyl acetate. The combined organic phases were washed with water and brine, dried over anhydrous $Na_2SO_4$, filtered and concentrated. Purification by flash chromatography gave 1-(6,7-dimethylpyrazolo[1,5-a]pyridin-3-yl)-5-fluoro-3,3-dimethyl-Isoquinolin-4-one (380 mg) as a brown solid: mp=139-141° C., LC-MS (Method G), Rt=0.95, UV Detection: 220 nm; MS: (M+1)=336; $^1$H NMR (400 MHz, CHLOROFORM-d) δ ppm 1.54 (s, 6H) 2.38 (s, 3H) 2.75 (s, 3H) 7.15 (d, 1H) 7.32 (t, 1H) 7.58 (d, 1H) 7.68-7.71 (m, 1H) 7.78 (d, 1H) 8.16 (s, 1H). $^{19}$F NMR (400 MHz, CHLOROFORM-d) δ ppm −112.

Step 6: Preparation of 1-(6,7-dimethylpyrazolo[1,5-a]pyridin-3-yl)-4,4,5-trifluoro-3,3-dimethyl-isoquinoline A solution of 1-(6,7-dimethylpyrazolo[1,5-a]pyridin-3-yl)-5-fluoro-3,3-dimethyl-isoquinolin-4-one (360 mg, 1.1 mmol) in 2,2-difluoro-1,3-dimethylimidazolidine (1.7 ml) was stirred at 105° C. for 24 hours. The reaction mixture was allowed to cool down to room temperature, diluted with dichloromethane then quenched by slow addition to an ice cooled saturated aqueous $NaHCO_3$ solution. The two phases were separated, and the aqueous phase was extracted with DCM. The combined organic phases were washed with brine, dried over $Na_2SO_4$, filtered and concentrated. The residue was purified by flash chromatography to give 1-(6,7-dimethylpyrazolo[1,5-a]pyridin-3-yl)-4,4,5-trifluoro-3,3-dimethyl-isoquinoline (310 mg) as a beige solid: mp=185-187° C., LC-MS (Method G) UV Detection: 220 nm, Rt=1.14, MS: (M+1)=358; $^1$H NMR (400 MHz, CHLOROFORM-d) δ ppm 1.45 (s, 6H) 2.40 (s, 3H) 2.78 (s, 3H) 7.17 (d, 1H) 7.31 (t, 1H) 7.51-7.60 (m, 2H) 7.90 (d, 1H) 8.15 (s, 1H). $^{19}$F NMR (400 MHz, CHLOROFORM-d) δ ppm −110, −113.

The following table gives analytical data for compounds of formula (I) prepared using synthetic techniques described above.

TABLE E

Physical data of compounds of formula (I)

| No. | Compound name | STRUCTURE | RT (min) | [M + H] (measured) | Method | MP ° C. |
|---|---|---|---|---|---|---|
| E-1 | 5-fluoro-1-imidazo[1,2-a]pyridin-3-yl-3,3,4,4-tetramethyl-isoquinoline | 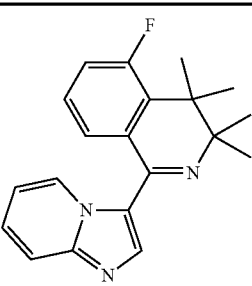 | 0.91 | 322 | G | 129-130 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-2 | 7-fluoro-1-imidazo[1,2-a]pyridin-3-yl-3,3,4,4-tetramethyl-isoquinoline | 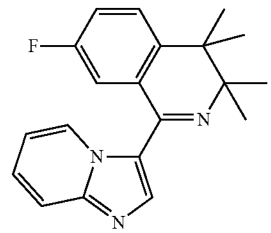 [SMILES: CC1(C)N=C(c2cnc3ccccn23)c2cc(F)ccc2C1(C)C] | 0.89 | 322 | G | |
| E-3 | 5-chloro-1-imidazo[1,2-a]pyridin-3-yl-3,3-dimethyl-4H-isoquinoline | 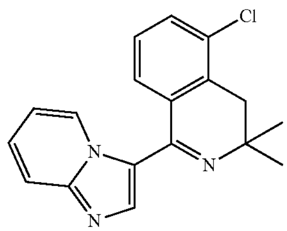 [SMILES: CC1(C)Cc2c(Cl)cccc2C(c2cnc3ccccn23)=N1] | 0.92 | 310 | G | |
| E-4 | 5-fluoro-1-(6-fluoroimidazo[1,2-a]pyridin-3-yl)-3,3,4,4-tetramethyl-isoquinoline | 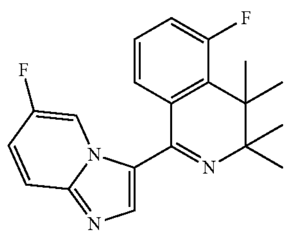 [SMILES: CC1(C)N=C(c2cnc3ccc(F)cn23)c2cccc(F)c2C1(C)C] | 1.13 | 340 | G | 200-202 |
| E-5 | 5-chloro-1-(6-fluoroimidazo[1,2-a]pyridin-3-yl)-3,3-dimethyl-4H-isoquinoline | 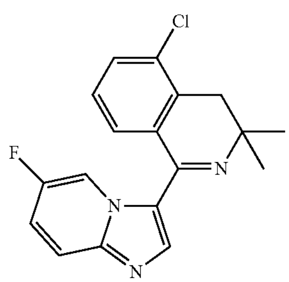 [SMILES: CC1(C)Cc2c(Cl)cccc2C(c2cnc3ccc(F)cn23)=N1] | 1.11 | 328 | G | 142-143 |
| E-6 | 5-fluoro-1-(8-fluoroimidazo[1,2-a]pyridin-3-yl)-3,3,4,4-tetramethyl-isoquinoline | 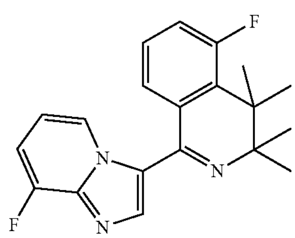 [SMILES: CC1(C)N=C(c2cnc3c(F)cccn23)c2cccc(F)c2C1(C)C] | 1.10 | 340 | G | 156-157 |
| E-7 | 1-[8-(difluoromethoxy)imidazo[1,2-a]pyridin-3-yl]-5-fluoro-3,3,4,4-tetramethyl-isoquinoline | 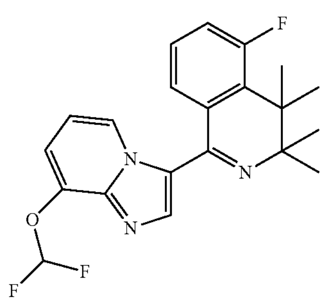 [SMILES: CC1(C)N=C(c2cnc3c(OC(F)F)cccn23)c2cccc(F)c2C1(C)C] | 1.15 | 388 | G | 121-122 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-8 | 1-(8-bromoimidazo[1,2-a]pyridin-3-yl)-5-fluoro-3,3,4,4-tetramethyl-isoquinoline | 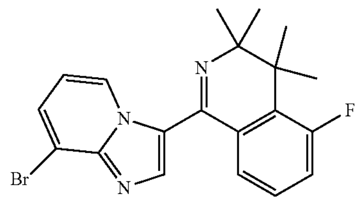 [SMILES: CC1(C)N=C(c2cnc3c(Br)cccn23)c2cccc(F)c2C1(C)C] | 1.15 | 402 | G | |
| E-9 | 5-fluoro-3,3,4,4-tetramethyl-1-(8-methylimidazo[1,2-a]pyridin-3-yl)isoquinoline | 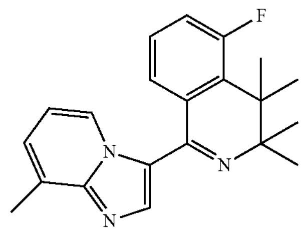 | 0.95 | 336 | G | 160-161 |
| E-10 | 5-fluoro-1-(8-fluoroimidazo[1,2-a]pyridin-3-yl)-3,3-dimethyl-4H-isoquinoline | 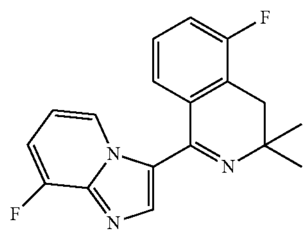 [SMILES: CC1(C)Cc2c(F)cccc2C(c2cnc3c(F)cccn23)=N1] | 0.99 | 312 | G | |
| E-11 | 5-chloro-1-(8-fluoroimidazo[1,2-a]pyridin-3-yl)-3,3-dimethyl-4H-isoquinoline | 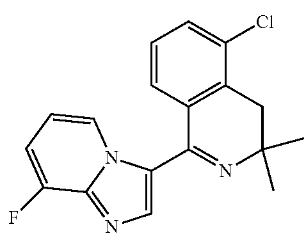 [SMILES: CC1(C)Cc2c(Cl)cccc2C(c2cnc3c(F)cccn23)=N1] | 1.09 | 328 | G | 122-123 |
| E-12 | 4-bromo-5-chloro-1-(8-fluoroimidazo[1,2-a]pyridin-3-yl)-3,3-dimethyl-4H-isoquinoline | 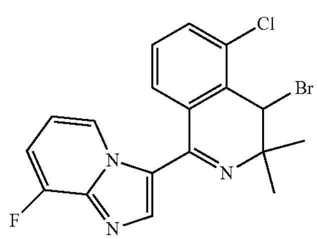 | 1.12 | 408 | G | 213-214 |
| E-13 | 4-bromo-5-fluoro-1-(8-fluoroimidazo[1,2-a]pyridin-3-yl)-3,3-dimethyl-4H-isoquinoline | 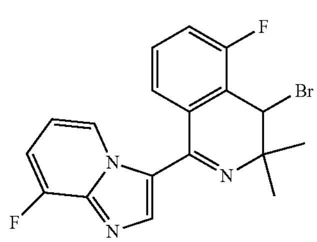 [SMILES: CC1(C)N=C(c2cnc3c(F)cccn23)c2cccc(F)c2C1Br] | 1.06 | 392 | G | 211-212 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-14 | 5-fluoro-1-(8-fluoroimidazo[1,2-a]pyridin-3-yl)-3,3-dimethyl-4H-isoquinolin-4-ol | 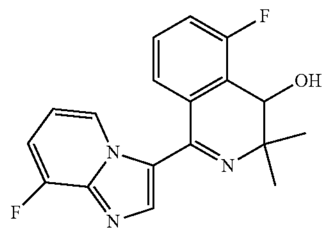 [SMILES: CC1(C)N=C(c2cnc3c(F)cccn23)c2cccc(F)c2C1O] | 0.77 | 328 | G | 219-219 |
| E-15 | 5-chloro-1-[8-(difluoromethoxy)imidazo[1,2-a]pyridin-3-yl]-3,3-dimethyl-4H-isoquinoline | 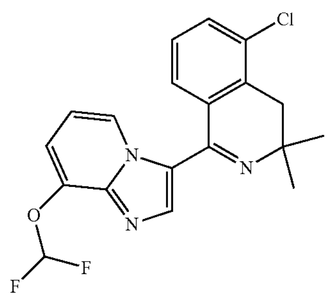 [SMILES: CC1(C)Cc2c(Cl)cccc2C(c2cnc3c(OC(F)F)cccn23)=N1] | 1.14 | 376 | G | 114-115 |
| E-16 | 1-(8-bromoimidazo[1,2-a]pyridin-3-yl)-5-fluoro-3,3-dimethyl-4H-isoquinoline | 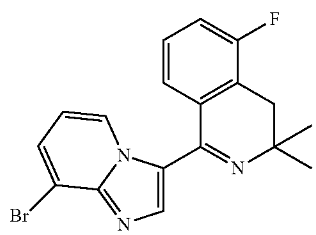 [SMILES: CC1(C)Cc2c(F)cccc2C(c2cnc3c(Br)cccn23)=N1] | 374 | 1.05 | G | 179-181 |
| E-17 | 5-fluoro-3,3-dimethyl-1-(8-methylsulfanyl-imidazo[1,2-a]pyridin-3-yl)-4H-isoquinoline | 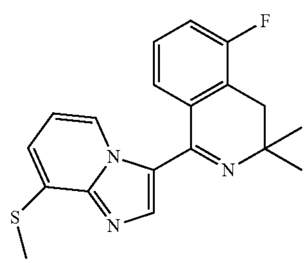 [SMILES: CSc1cccn2c(C3=NC(C)(C)Cc4c(F)cccc43)cnc12] | 340 | 0.96 | G | 119-120 |
| E-18 | 5-fluoro-1-(8-fluoroimidazo[1,2-a]pyridin-3-yl)-3,3-dimethyl-isoquinolin-4-one | 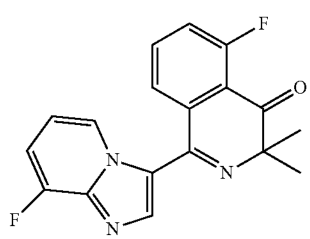 [SMILES: CC1(C)N=C(c2cnc3c(F)cccn23)c2cccc(F)c2C1=O] | 0.90 | 326 | G | 160-161 |
| E-19 | 4,4,5-trifluoro-1-(8-fluoroimidazo[1,2-a]pyridin-3-yl)-3,3-dimethyl-isoquinoline | 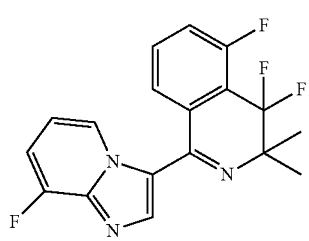 [SMILES: CC1(C)N=C(c2cnc3c(F)cccn23)c2cccc(F)c2C1(F)F] | 1.06 | 348 | G | 145-146 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-20 | 5-fluoro-1-(8-fluoroimidazo[1,2-a]pyridin-3-yl)-N-methoxy-3,3-dimethyl-isoquinolin-4-imine | 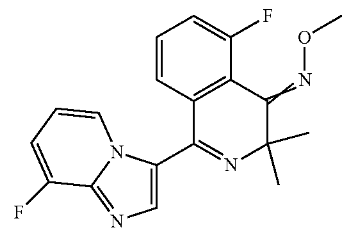 [SMILES: CON=C1c2c(F)cccc2C(c2cnc3c(F)cccn23)=NC1(C)C] | 1.08 | 355 | G | |
| E-21 | 1-(8-ethylimidazo[1,2-a]pyridin-3-yl)-5-fluoro-3,3,4,4-tetramethyl-isoquinoline | 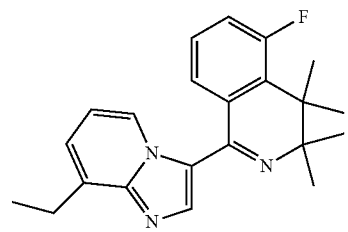 [SMILES: CCc1cccn2c(C3=NC(C)(C)C(C)(C)c4c(F)cccc43)cnc12] | 1.02 | 350 | G | |
| E-22 | 1-(8-cyclopropylimidazo[1,2-a]pyridin-3-yl)-5-fluoro-3,3,4,4-tetramethyl-isoquinoline | 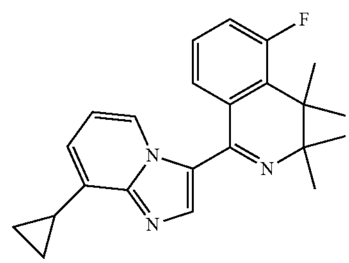 [SMILES: CC1(C)N=C(c2cnc3c(C4CC4)cccn23)c2cccc(F)c2C1(C)C] | 1.03 | 362 | G | |
| E-23 | 1-(8-ethynylimidazo[1,2-a]pyridin-3-yl)-5-fluoro-3,3,4,4-tetramethyl-isoquinoline | 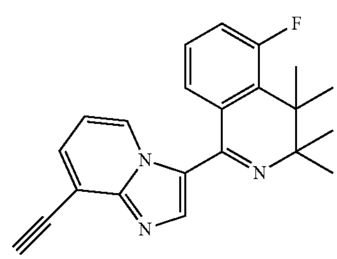 [SMILES: C#Cc1cccn2c(C3=NC(C)(C)C(C)(C)c4c(F)cccc43)cnc12] | 1.06 | 346 | G | 169-170 |
| E-24 | 5-fluoro-1-(8-methoxyimidazo[1,2-a]pyridin-3-yl)-3,3,4,4-tetramethyl-isoquinoline | 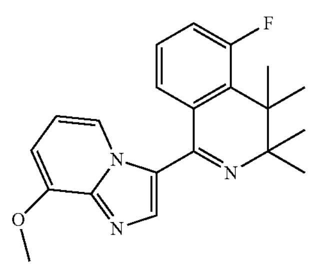 [SMILES: COc1cccn2c(C3=NC(C)(C)C(C)(C)c4c(F)cccc43)cnc12] | 0.92 | 352 | G | 130-130 |
| E-25 | 5-fluoro-1-(6-methoxyimidazo[1,2-a]pyridin-3-yl)-3,3,4,4-tetramethyl-isoquinoline | 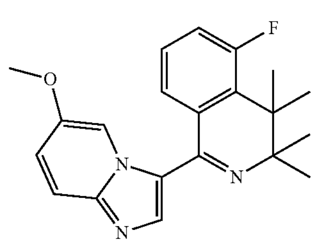 | 1.05 | 352 | G | 214-215 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-26 | 3-(5-fluoro-3,3,4,4-tetramethyl-1-isoquinolyl)imidazo[1,2-a]pyridin-6-ol | 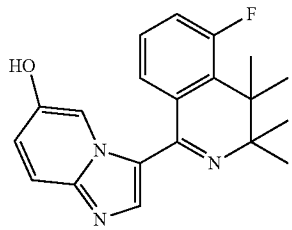 [SMILES: CC1(C)N=C(c2cnc3ccc(O)cn23)c2cccc(F)c2C1(C)C] | 0.85 | 338 | G | 321-322 |
| E-27 | 3-(5-fluoro-3,3,4,4-tetramethyl-1-isoquinolyl)imidazo[1,2-a]pyridin-8-ol | 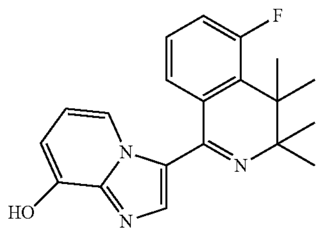 [SMILES: CC1(C)N=C(c2cnc3c(O)cccn23)c2cccc(F)c2C1(C)C] | 0.91 | 338 | G | 271-272 |
| E-28 | 5-fluoro-3,3,4,4-tetramethyl-1-(8-prop-2-ynoxyimidazo[1,2-a]pyridin-3-yl)isoquinoline | 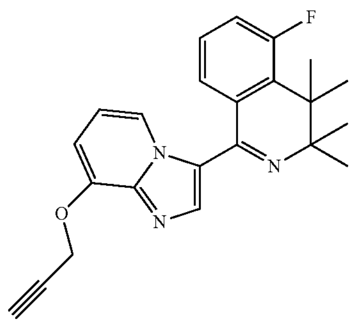 [SMILES: C#CCOc1cccn2c(C3=NC(C)(C)C(C)(C)c4c(F)cccc43)cnc12] | 1.01 | 376 | G | |
| E-29 | 5-fluoro-3,3,4,4-tetramethyl-1-[8-(trifluoromethyl)imidazo[1,2-a]pyridin-3-yl]isoquinoline | 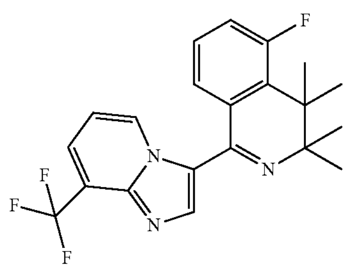 [SMILES: CC1(C)N=C(c2cnc3c(C(F)(F)F)cccn23)c2cccc(F)c2C1(C)C] | 1.22 | 390 | G | 141-142 |
| E-30 | 5-fluoro-3,3,4,4-tetramethyl-1-(5-methylimidazo[1,2-a]pyridin-3-yl)isoquinoline | 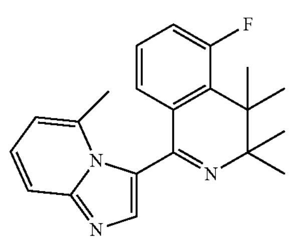 [SMILES: Cc1cccc2ncc(C3=NC(C)(C)C(C)(C)c4c(F)cccc43)n12] | 0.87 | 336 | G | 139-140 |
| E-31 | 5-fluoro-3,3,4,4-tetramethyl-1-(7-methylimidazo[1,2-a]pyridin-3-yl)isoquinoline | 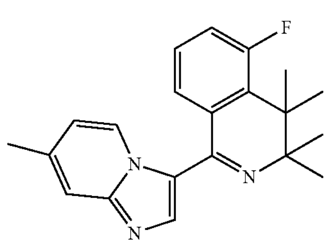 | 1.02 | 336 | G | |

TABLE E-continued

Physical data of compounds of formula (I)

| No. | Compound name | STRUCTURE | RT (min) | [M + H] (measured) | Method | MP ° C. |
|---|---|---|---|---|---|---|
| E-32 | 1-(8-chloroimidazo[1,2-a]pyridin-3-yl)-5-fluoro-3,3,4,4-tetramethyl-isoquinoline | 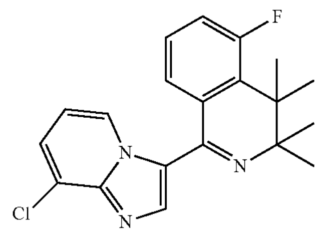 [SMILES: CC1(C)N=C(c2cnc3c(Cl)cccn23)c2cccc(F)c2C1(C)C] | 1.14 | 356 | G | 167-168 |
| E-33 | 3,3,4,4-tetramethyl-1-(8-methylimidazo[1,2-a]pyridin-3-yl)isoquinoline | 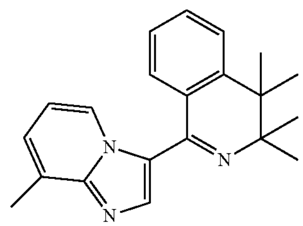 | 0.88 | 318 | G | |
| E-34 | 4-bromo-1-(8-bromoimidazo[1,2-a]pyridin-3-yl)-5-fluoro-3,3-dimethyl-4H-isoquinoline | 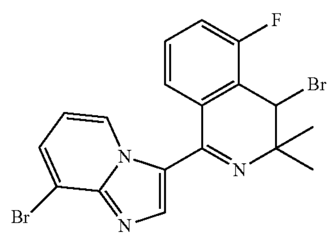 [SMILES: CC1(C)N=C(c2cnc3c(Br)cccn23)c2cccc(F)c2C1Br] | 1.11 | 452 | G | 217-218 |
| E-35 | 1-(8-bromoimidazo[1,2-a]pyridin-3-yl)-5-fluoro-3,3-dimethyl-4H-isoquinolin-4-ol | 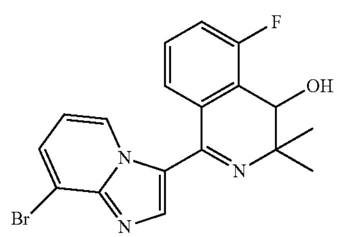 [SMILES: CC1(C)N=C(c2cnc3c(Br)cccn23)c2cccc(F)c2C1O] | 0.83 | 390 | G | 204-205 |
| E-36 | 1-(8-bromoimidazo[1,2-a]pyridin-3-yl)-5-fluoro-3,3-dimethyl-isoquinolin-4-one | 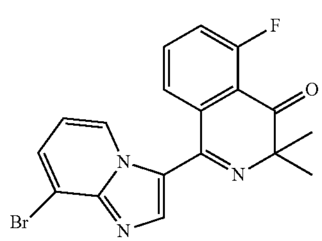 [SMILES: CC1(C)N=C(c2cnc3c(Br)cccn23)c2cccc(F)c2C1=O] | 0.95 | 388 | G | 146-147 |
| E-37 | 1-(8-bromoimidazo[1,2-a]pyridin-3-yl)-4,4,5-trifluoro-3,3-dimethyl-isoquinoline | 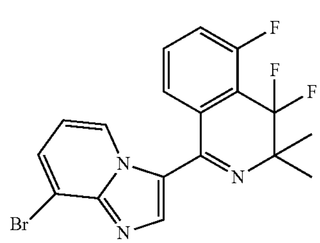 [SMILES: CC1(C)N=C(c2cnc3c(Br)cccn23)c2cccc(F)c2C1(F)F] | 1.10 | 309 | G | 209-210 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-38 | 3-(5-fluoro-3,3,4,4-tetramethyl-1-isoquinolyl)imidazo[1,2-a]pyridine-8-carbonitrile | 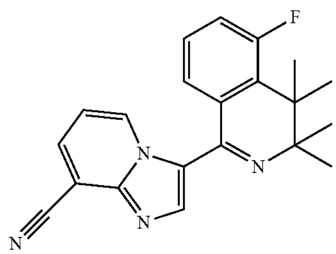 [SMILES: CC1(C)N=C(c2cnc3c(C#N)cccn23)c2cccc(F)c2C1(C)C] | 1.12 | 437 | G | 212-213 |
| E-39 | 4,4,5-trifluoro-3,3-dimethyl-1-(8-methylimidazo[1,2-a]pyridin-3-yl)isoquinoline | 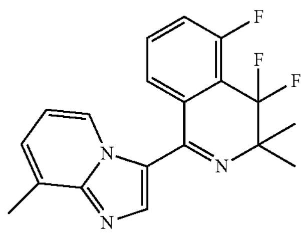 [SMILES: Cc1cccn2c(C3=NC(C)(C)C(F)(F)c4c(F)cccc43)cnc12] | 0.99 | 344 | G | |
| E-40 | 1-(2,8-dimethylimidazo[1,2-a]pyridin-3-yl)-5-fluoro-3,3,4,4-tetramethyl-isoquinoline | 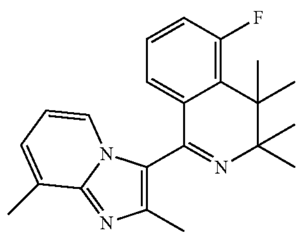 | 0.93 | 350 | G | |
| E-41 | 1-(8-bromoimidazo[1,2-a]pyridin-3-yl)-3,3-dimethyl-4H-isoquinoline | 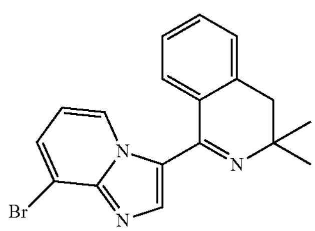 [SMILES: CC1(C)Cc2ccccc2C(c2cnc3c(Br)cccn23)=N1] | 0.84 | 356 | G | 132-133 |
| E-42 | 1-(8-bromoimidazo[1,2-a]pyridin-3-yl)-3,3-dimethyl-isoquinolin-4-one | 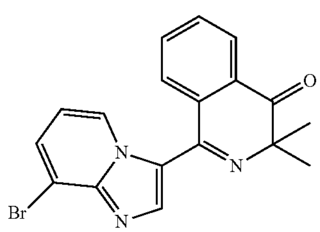 [SMILES: CC1(C)N=C(c2cnc3c(Br)cccn23)c2ccccc2C1=O] | 0.96 | 370 | G | 204-205 |
| E-43 | 1-(8-bromoimidazo[1,2-a]pyridin-3-yl)-4,4-difluoro-3,3-dimethyl-isoquinoline | 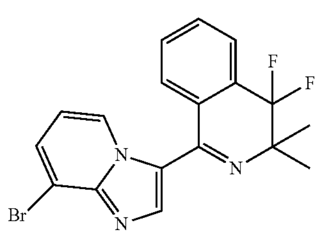 [SMILES: CC1(C)N=C(c2cnc3c(Br)cccn23)c2ccccc2C1(F)F] | 1.11 | 392 | G | 173-173 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-44 | 5-fluoro-1-(7-iodoimidazo[1,2-a]pyridin-3-yl)-3,3,4,4-tetramethyl-isoquinoline | 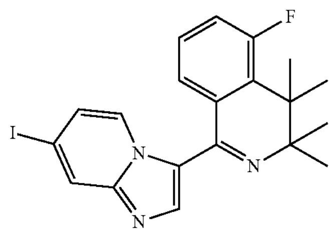 [SMILES: CC1(C)N=C(c2cnc3cc(I)ccn23)c2cccc(F)c2C1(C)C] | 1.21 | 448 | G | |
| E-45 | 4,4-difluoro-3,3-dimethyl-1-(8-methylimidazo[1,2-a]pyridin-3-yl)isoquinoline | 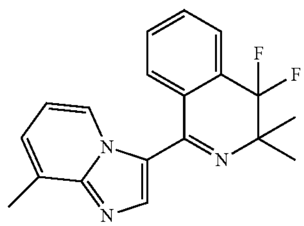 [SMILES: Cc1cccn2c(C3=NC(C)(C)C(F)(F)c4ccccc43)cnc12] | 0.95 | 326 | G | |
| E-46 | 3-(5-fluoro-3,3,4,4-tetramethyl-1-isoquinolyl)imidazo[1,2-a]pyridine-7-carbonitrile | 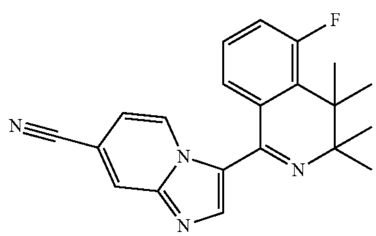 [SMILES: CC1(C)N=C(c2cnc3cc(C#N)ccn23)c2cccc(F)c2C1(C)C] | 1.12 | 347 | G | 193-194 |
| E-47 | 1-(8-chloro-7-methyl-imidazo[1,2-a]pyridin-3-yl)-5-fluoro-3,3,4,4-tetramethyl-isoquinoline | 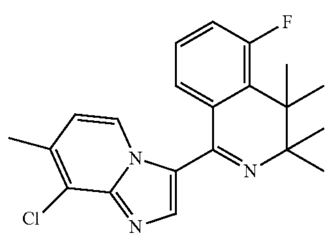 | 1.14 | 370 | G | 185-186 |
| E-48 | 5-fluoro-1-(7-methoxyimidazo[1,2-a]pyridin-3-yl)-3,3,4,4-tetramethyl-isoquinoline | 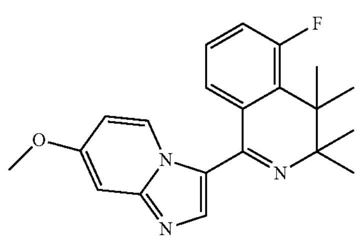 | 0.99 | 352 | G | 139-140 |
| E-49 | 3-(5-fluoro-3,3,4,4-tetramethyl-1-isoquinolyl)imidazo[1,2-a]pyridin-7-ol | 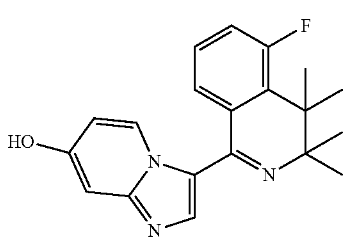 [SMILES: CC1(C)N=C(c2cnc3cc(O)ccn23)c2cccc(F)c2C1(C)C] | 0.88 | 338 | G | 246-247 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-50 | 1-(7,8-dimethylimidazo[1,2-a]pyridin-3-yl)-5-fluoro-3,3,4,4-tetramethyl-isoquinoline | 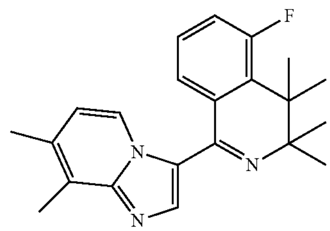 | 0.91 | 350 | G | 185-186 |
| E-51 | 4,4-dimethyl-1-(8-methylimidazo[1,2-a]pyridin-3-yl)-3H-isoquinoline | 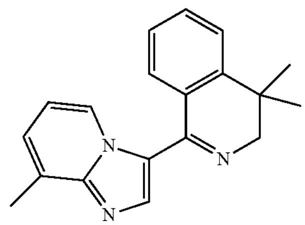 | 0.73 | 290 | G | |
| E-52 | 1-(8-methylimidazo[1,2-a]pyridin-3-yl)spiro[4H-isoquinoline-3,1'-cyclobutane] | 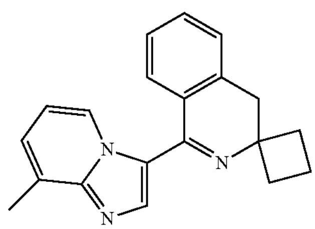 [SMILES: Cc1cccn2c(C3=NC4(CCC4)Cc4ccccc43)cnc12] | 0.80 | 302 | G | |
| E-53 | 1-(8-methylimidazo[1,2-a]pyridin-3-yl)spiro[3H-isoquinoline-4,1'-cyclobutane] | 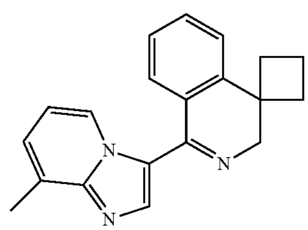 [SMILES: Cc1cccn2c(C3=NCC4(CCC4)c4ccccc43)cnc12] | 1.14 | 302 | G | 127-129 |
| E-54 | 1-(7-iodoimidazo[1,2-a]pyridin-3-yl)-3,3-dimethyl-4H-isoquinoline | 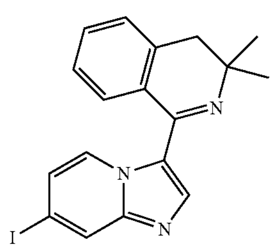 [SMILES: CC1(C)Cc2ccccc2C(c2cnc3cc(I)ccn23)=N1] | 1.57 | 402.1 | H | 190-193 |
| E-55 | 4,4-difluoro-3,3-dimethyl-1-(7-methylimidazo[1,2-a]pyridin-3-yl)isoquinoline | 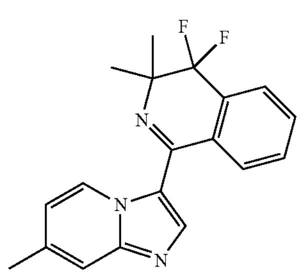 [SMILES: Cc1ccn2c(C3=NC(C)(C)C(F)(F)c4ccccc43)cnc2c1] | 1.26 | 326.3 | H | |

TABLE E-continued

Physical data of compounds of formula (I)

| No. | Compound name | STRUCTURE | RT (min) | [M + H] (measured) | Method | MP ° C. |
|---|---|---|---|---|---|---|
| E-56 | 1-(7,8-dichloroimidazo[1,2-a]pyridin-3-yl)-4,4-difluoro-3,3-dimethyl-isoquinoline | 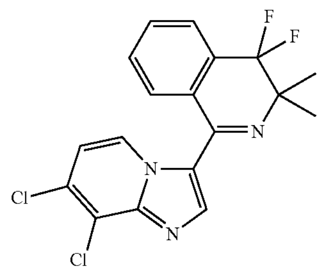 [SMILES: CC1(C)N=C(c2cnc3c(Cl)c(Cl)ccn23)c2ccccc2C1(F)F] | 1.19 | 381 | G | >210 |
| E-57 | 1-(7,8-dimethylimidazo[1,2-a]pyridin-3-yl)-4,4-difluoro-3,3-dimethyl-isoquinoline | 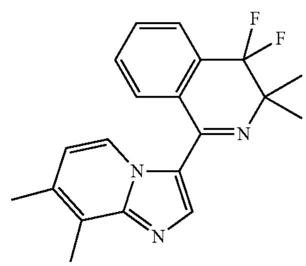 | 0.88 | 340 | G | 159-161 |
| E-58 | 5-fluoro-3,3,4,4-tetramethyl-1-pyrazolo[1,5-a]pyridin-3-yl-isoquinoline | 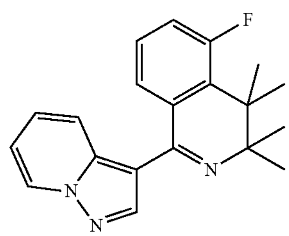 [SMILES: CC1(C)N=C(c2cnn3ccccc23)c2cccc(F)c2C1(C)C] | 0.74 | 322 | G | 124-126 |
| E-59 | 5-fluoro-3,3,4,4-tetramethyl-1-(7-methylpyrazolo[1,5-a]pyridin-3-yl)isoquinoline | 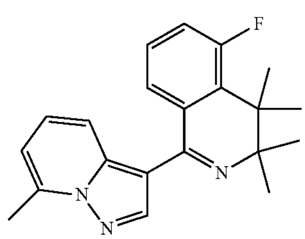 | 0.81 | 336 | G | 134-136 |
| E-60 | 5-bromo-3,3-dimethyl-1-pyrazolo[1,5-a]pyridin-3-yl-4H-isoquinoline | 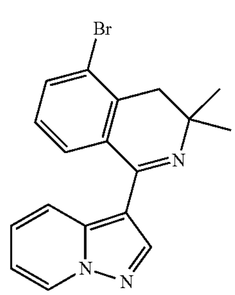 [SMILES: CC1(C)Cc2c(Br)cccc2C(c2cnn3ccccc23)=N1] | 0.78 | 354-356 | G | |

TABLE E-continued

Physical data of compounds of formula (I)

| No. | Compound name | STRUCTURE | RT (min) | [M + H] (measured) | Method | MP ° C. |
|---|---|---|---|---|---|---|
| E-61 | 5-fluoro-3,3-dimethyl-1-pyrazolo[1,5-a]pyridin-3-yl-4H-isoquinoline | 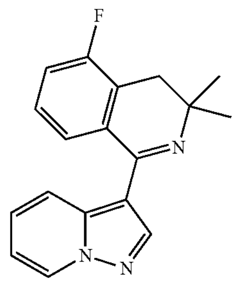 [SMILES: CC1(C)Cc2c(F)cccc2C(c2cnn3ccccc23)=N1] | 0.67 | 294 | G | |
| E-62 | 5-fluoro-3,3,4,4-tetramethyl-1-(2-methylpyrazolo[1,5-a]pyridin-3-yl)isoquinoline | 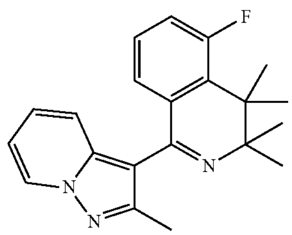 [SMILES: Cc1nn2ccccc2c1C1=NC(C)(C)C(C)(C)c2c(F)cccc21] | 0.77 | 335 | G | |
| E-63 | 1-(6,7-dimethylpyrazolo[1,5-a]pyridin-3-yl)-5-fluoro-3,3,4,4-tetramethyl-isoquinoline | 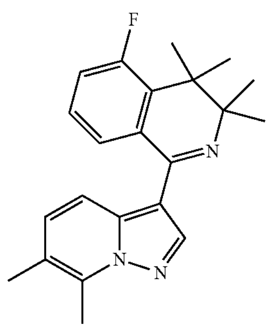 | 0.88 | 350 | G | 175-176 |
| E-64 | 1-(6,7-dimethylpyrazolo[1,5-a]pyridin-3-yl)-3,3-dimethyl-isoquinolin-4-one | 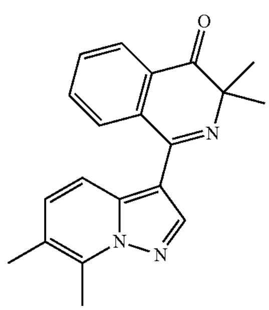 | 0.86 | 318 | G | 152-153 |
| E-65 | 1-(6,7-dimethylpyrazolo[1,5-a]pyridin-3-yl)-4,4-difluoro-3,3-dimethyl-isoquinoline | 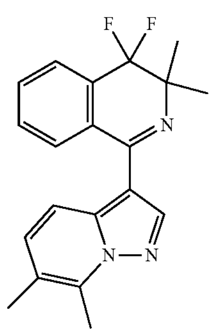 | 1.03 | 340 | G | 160-161 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-66 | 4,4-difluoro-3,3-dimethyl-1-(7-methylpyrazolo[1,5-a]pyridin-3-yl)isoquinoline | 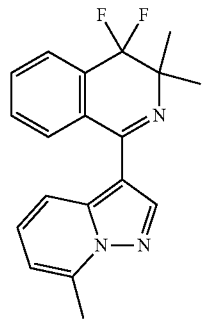 [SMILES: Cc1cccc2c(C3=NC(C)(C)C(F)(F)c4ccccc43)cnn12] | 0.97 | 326 | G | 105-107 |
| E-67 | 3,3-dimethyl-1-(7-methylpyrazolo[1,5-a]pyridin-3-yl)isoquinolin-4-one | 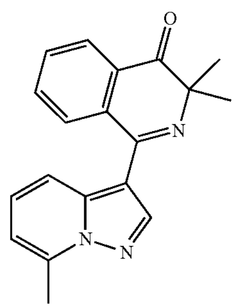 [SMILES: Cc1cccc2c(C3=NC(C)(C)C(=O)c4ccccc43)cnn12] | 0.77 | 304 | G | 110-112 |
| E-68 | 3,3-dimethyl-1-(4-methylpyrazolo[1,5-a]pyridin-3-yl)isoquinolin-4-one | 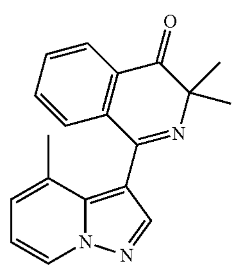 [SMILES: Cc1cccn2ncc(C3=NC(C)(C)C(=O)c4ccccc43)c12] | 0.83 | 304 | G | 140-141 |
| E-69 | 4,4-difluoro-3,3-dimethyl-1-(4-methylpyrazolo[1,5-a]pyridin-3-yl)isoquinoline | 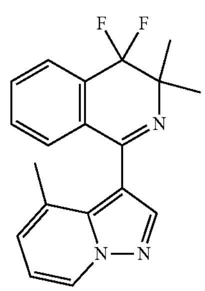 [SMILES: Cc1cccn2ncc(C3=NC(C)(C)C(F)(F)c4ccccc43)c12] | 0.99 | 326 | G | 113-114 |
| E-70 | 1-(6,7-dimethylpyrazolo[1,5-a]pyridin-3-yl)-4,4,6-trifluoro-3,3-dimethyl-isoquinoline | 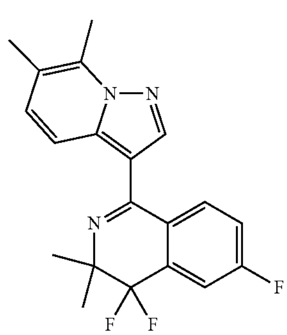 [SMILES: Cc1ccc2c(C3=NC(C)(C)C(F)(F)c4cc(F)ccc43)cnn2c1C] | 1.09 | 358 | G | 183-185 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-71 | 1-(6,7-dimethylpyrazolo[1,5-a]pyridin-3-yl)-4,4,5-trifluoro-3,3-dimethyl-isoquinoline | 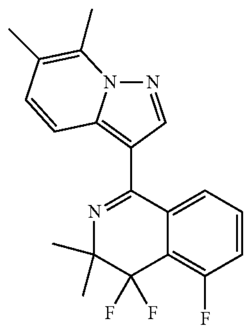 [SMILES: Cc1ccc2c(C3=NC(C)(C)C(F)(F)c4c(F)cccc43)cnn2c1C] | 1.14 | 358 | G | 185-187 |
| E-72 | 1-(6,7-dimethylpyrazolo[1,5-a]pyridin-3-yl)-5-fluoro-3,3-dimethyl-isoquinolin-4-one | 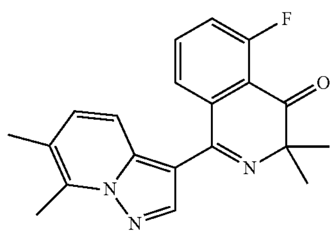 | 0.95 | 336 | G | 139-141 |
| E-73 | 5-fluoro-3,3-dimethyl-1-(4-methylpyrazolo[1,5-a]pyridin-3-yl)isoquinolin-4-one | 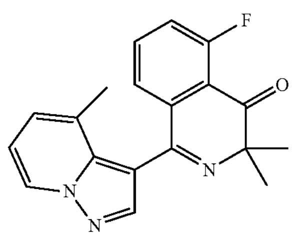 [SMILES: Cc1cccn2ncc(C3=NC(C)(C)C(=O)c4c(F)cccc43)c12] | 0.89 | 322 | G | 141-143 |
| E-74 | 1-(6,7-dimethylpyrazolo[1,5-a]pyridin-3-yl)-6-fluoro-3,3-dimethyl-isoquinolin-4-one | 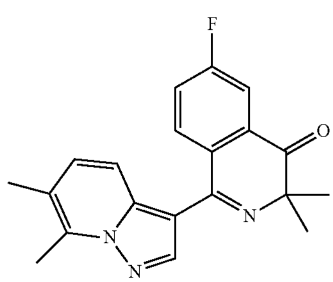 | 0.92 | 336 | G | 168-170 |
| E-75 | 6-fluoro-3,3-dimethyl-1-(4-methylpyrazolo[1,5-a]pyridin-3-yl)isoquinolin-4-one | 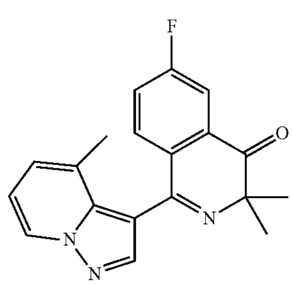 [SMILES: Cc1cccn2ncc(C3=NC(C)(C)C(=O)c4cc(F)ccc43)c12] | 0.89 | 322 | G | 180-183 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-78 | 1-(6-bromo-7-methyl-pyrazolo[1,5-a]pyridin-3-yl)-3,3-dimethyl-isoquinolin-4-one | 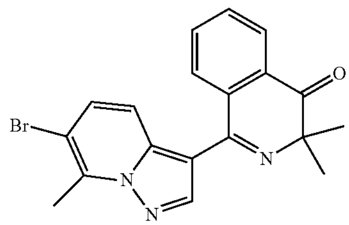 [SMILES: Cc1c(Br)ccc2c(C3=NC(C)(C)C(=O)c4ccccc43)cnn12] | 1.13 | 382-384 | G | 166-168 |
| E-79 | 1-(6-bromo-7-methyl-pyrazolo[1,5-a]pyridin-3-yl)-4,4-difluoro-3,3-dimethyl-isoquinoline | 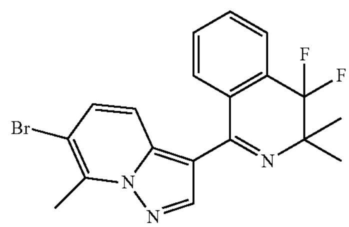 [SMILES: Cc1c(Br)ccc2c(C3=NC(C)(C)C(F)(F)c4ccccc43)cnn12] | 1.34 | 404-406 | G | 180-182 |
| E-80 | 4,4-difluoro-3,3-dimethyl-1-pyrazolo[1,5-a]pyridin-3-yl-isoquinoline | 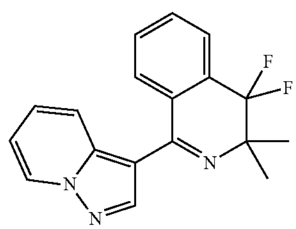 [SMILES: CC1(C)N=C(c2cnn3ccccc23)c2ccccc2C1(F)F] | 0.97 | 312 | G | 78-82 |
| E-81 | 1-(6-bromopyrazolo[1,5-a]pyridin-3-yl)-4,4-difluoro-3,3-dimethyl-isoquinoline | 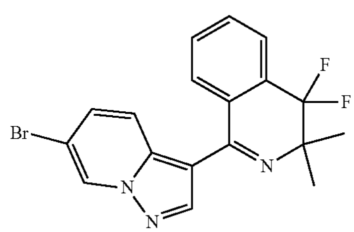 [SMILES: CC1(C)N=C(c2cnn3cc(Br)ccc23)c2ccccc2C1(F)F] | 1.17 | 390-392 | G | 127-129 |
| E-82 | 1-(6-bromopyrazolo[1,5-a]pyridin-3-yl)-3,3-dimethyl-isoquinolin-4-one | 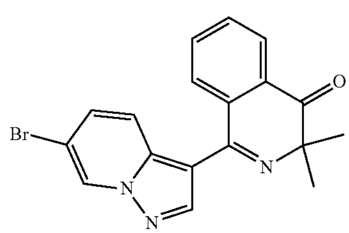 [SMILES: CC1(C)N=C(c2cnn3cc(Br)ccc23)c2ccccc2C1=O] | 0.96 | 368-370 | G | 147-149 |
| E-83 | 4,4-difluoro-3,3-dimethyl-1-(6-methylpyrazolo[1,5-a]pyridin-3-yl)isoquinoline | 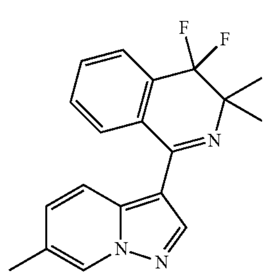 | 0.96 | 326 | G | 105-107 |

TABLE E-continued

Physical data of compounds of formula (I)

| No. | Compound name | STRUCTURE | RT (min) | [M + H] (measured) | Method | MP ° C. |
|---|---|---|---|---|---|---|
| E-84 | 1-(4-bromopyrazolo[1,5-a]pyridin-3-yl)-3,3-dimethyl-isoquinolin-4-one | 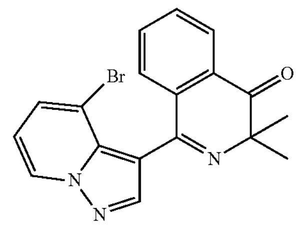 [SMILES: CC1(C)N=C(c2cnn3cccc(Br)c23)c2ccccc2C1=O] | 0.85 | 368-370 | G | 148-151 |
| E-85 | 3-(4,4-difluoro-3,3-dimethyl-1-isoquinolyl)pyrazolo[1,5-a]pyridine-6-carbonitrile | 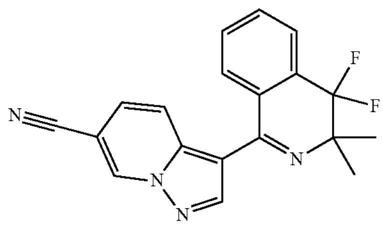 [SMILES: CC1(C)N=C(c2cnn3cc(C#N)ccc23)c2ccccc2C1(F)F] | 1.06 | 337 | G | 191-194 |
| E-86 | 1-(6-ethylpyrazolo[1,5-a]pyridin-3-yl)-4,4-difluoro-3,3-dimethyl-isoquinoline | 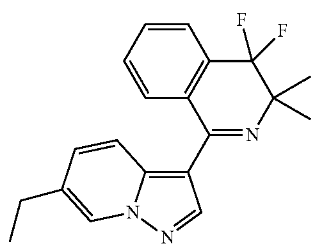 [SMILES: CCc1ccc2c(C3=NC(C)(C)C(F)(F)c4ccccc43)cnn2c1] | 1.04 | 340 | G | |
| E-87 | 1-(6-chloropyrazolo[1,5-a]pyridin-3-yl)-4,4-difluoro-3,3-dimethyl-isoquinoline | 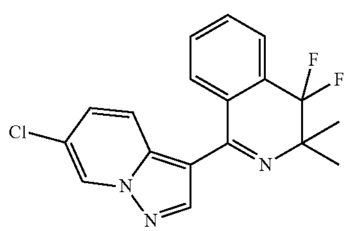 [SMILES: CC1(C)N=C(c2cnn3cc(Cl)ccc23)c2ccccc2C1(F)F] | 1.16 | 346-348 | G | 113-118 |
| E-88 | 4,4-difluoro-1-(6-fluoro-7-methyl-pyrazolo[1,5-a]pyridin-3-yl)-3,3-dimethyl-isoquinoline | 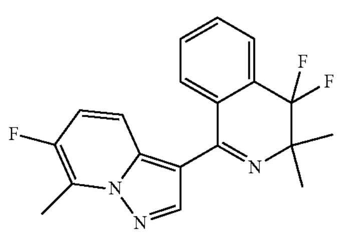 [SMILES: Cc1c(F)ccc2c(C3=NC(C)(C)C(F)(F)c4ccccc43)cnn12] | 1.13 | 344 | G | 115-118 |
| E-89 | 4,4-difluoro-1-(4-fluoropyrazolo[1,5-a]pyridin-3-yl)-3,3-dimethyl-isoquinoline | 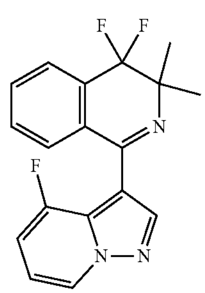 [SMILES: CC1(C)N=C(c2cnn3cccc(F)c23)c2ccccc2C1(F)F] | 0.89 | 330 | G | |

TABLE E-continued

Physical data of compounds of formula (I)

| No. | Compound name | STRUCTURE | RT (min) | [M + H] (measured) | Method | MP ° C. |
|---|---|---|---|---|---|---|
| E-90 | 1-(6-ethynylpyrazolo[1,5-a]pyridin-3-yl)-4,4-difluoro-3,3-dimethyl-isoquinoline | 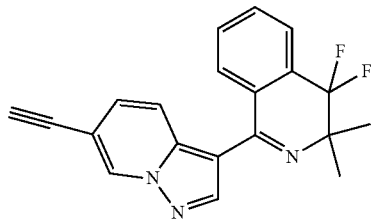 [SMILES: C#Cc1ccc2c(C3=NC(C)(C)C(F)(F)c4ccccc43)cnn2c1] | 1.10 | 336 | G | 145-147 |
| E-91 | 1-(6-chloro-7-methyl-pyrazolo[1,5-a]pyridin-3-yl)-4,4-difluoro-3,3-dimethyl-isoquinoline | 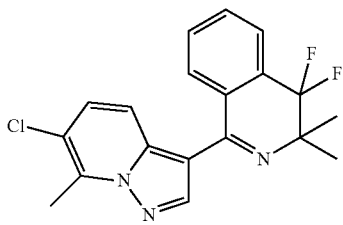 [SMILES: Cc1c(Cl)ccc2c(C3=NC(C)(C)C(F)(F)c4ccccc43)cnn12] | 1.23 | 360-362 | G | 166-168 |
| E-92 | 4,4-difluoro-1-(7-methoxypyrazolo[1,5-a]pyridin-3-yl)-3,3-dimethyl-isoquinoline | 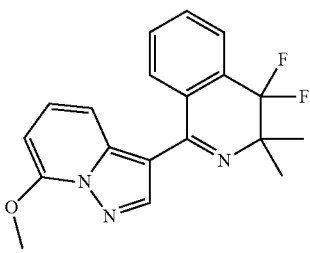 [SMILES: COc1cccc2c(C3=NC(C)(C)C(F)(F)c4ccccc43)cnn12] | 0.87 | 342 | G | 120-124 |
| E-93 | 1-(7-chloropyrazolo[1,5-a]pyridin-3-yl)-4,4-difluoro-3,3-dimethyl-isoquinoline | 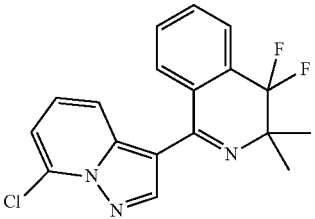 [SMILES: CC1(C)N=C(c2cnn3c(Cl)cccc23)c2ccccc2C1(F)F] | 1.11 | 346-348 | G | 129-132 |
| E-94 | | 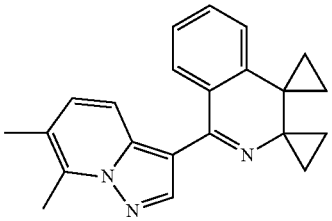 [SMILES: Cc1ccc2c(C3=NC4(CC4)C4(CC4)c4ccccc43)cnn2c1C] | 0.82 | 328 | G | 124-126 |
| E-95 | | 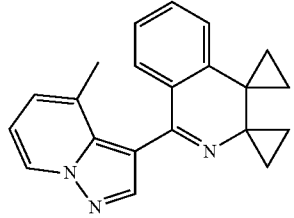 [SMILES: Cc1cccn2ncc(C3=NC4(CC4)C4(CC4)c4ccccc43)c12] | 0.77 | 314 | G | |

BIOLOGICAL EXAMPLES

*Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application. The following compounds gave at least 80% control of *Botryotinia fuckeliana* at 20 ppm when compared to untreated control under the same conditions, which showed extensive disease development:
E-1, E-6, E-7, E-8, E-9, E-10, E-11, E-19, E-21, E-22, E-23, E-24, E-27, E-29, E-30, E-31, E-32, E-33, E-38, E-39, E-40, E-44, E-45, E-46, E-47, E-48, E-49, E-50, E-51, E-52, E-53, E-55, E-56, E-57, E-58, E-59, E-60, E-62, E-63, E-64, E-65, E-66, E-67, E-68, E-69, E-70, E-71, E-72, E-74, E-75, E-76, E-77, E-78, E-79, E-80, E-81, E-82, E-83, E-85, E-86, E-87, E-88, E-89, E-91, E-92, E-93, E-95, E-95.

*Glomerella Lagenarium* (*Colletotrichum lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds gave at least 80% control of *Glomerella lagenarium* at 20 ppm when compared to untreated control under the same conditions, which showed extensive disease development:
E-1, E-2, E-3, E-6, E-7, E-8, E-9, E-10, E-11, E-14, E-16, E-17, E-19, E-21, E-22, E-24, E-27, E-29, E-30, E-31, E-32, E-33, E-37, E-38, E-39, E-40, E-44, E-45, E-46, E-47, E-48, E-49, E-50, E-52, E-55, E-57, E-58, E-59, E-62, E-63, E-64, E-65, E-66, E-67, E-69, E-70, E-71, E-72, E-74, E-76, E-77, E-78, E-79, E-80, E-81, E-82, E-83, E-86, E-87, E-88, E-89, E-90, E-91, E-92, E-93, E-94, E-95.

*Fusarium culmorum*/Liquid Culture (Head Blight)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Fusarium culmorum* at 20 ppm when compared to untreated control under the same conditions, which showed extensive disease development:
E-1, E-6, E-8, E-9, E-21, E-31, E-32, E-33, E-39, E-44, E-45, E-47, E-50, E-55, E-57, E-59, E-63, E-64, E-65, E-66, E-67, E-69, E-70, E-71, E-72, E-74, E-76, E-78, E-79, E-80, E-81, E-82, E-83, E-86, E-87, E-88, E-89, E-91, E-92, E-93, E-94.

*Gaeumannomyces graminis*/Liquid Culture (Take-all of Cereals)

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Gaeumannomyces graminis* at 20 ppm when compared to untreated control under the same conditions, which showed extensive disease development:
E-1, E-6, E-9, E-25, E-37, E-38, E-39, E-41, E-58, E-63, E-64, E-65, E-66, E-69, E-71, E-76, E-79, E-80, E-81, E-82, E-83, E-86, E-87, E-88, E-90, E-91, E-92, E-94.

*Monographella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Monographella nivalis* at 20 ppm when compared to untreated control under the same conditions, which showed extensive disease development:
E-6, E-9, E-15, E-21, E-22, E-24, E-29, E-33, E-38, E-39, E-44, E-45, E-52, E-53, E-57, E-59, E-64, E-65, E-66, E-67, E-69, E-70, E-71, E-72, E-76, E-78, E-80, E-81, E-82, E-83, E-88, E-89, E-90, E-91, E-92, E-93, E-94.

*Mycosphaerella graminicola* (*Septoria tritici*)/Liquid Culture (*Septoria* Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Mycosphaerella graminicola* at 20 ppm when compared to untreated control under the same conditions, which showed extensive disease development:
E-22, E-39, E-44, E-80, E-81, E-82, E-83, E-86, E-87, E-88, E-93

*Magnaporthe grisea* (*Pyricularia oryzae*)/Rice/Leaf Disc Preventative (Rice Blast)

Rice leaf segments cv. Ballila are placed on agar in a multiwell plate (24-well format) and sprayed with the formulated test compound diluted in water. The leaf segments are inoculated with a spore suspension of the fungus 2 days after application. The inoculated leaf segments are incubated at 22° C. and 80% r.h. under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application).

The following compounds gave at least 50% control of *Magnaporthe grisea* at 200 ppm when compared to untreated control under the same conditions, which showed extensive disease development:
E-6, E-8, E-9, E-31, E-33, E-39, E-45, E-57, E-59, E-63, E-66, E-69, E-70, E-71, E-81, E-83, E-86, E-87, E-88, E-91, E-92, E-93, E-94, E-95.

*Magnaporthe grisea* (*Pyricularia Oryzae*)/Liquid Culture (Rice Blast)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application. The following compounds gave at least 80% control of *Magnaporthe grisea* at 60 ppm when compared to untreated control under the same conditions, which showed extensive disease development:

E-50, E-51, E-52, E-53, E-55, E-56, E-57, E-63, E-64, E-65, E-66, E-67, E-69, E-70, E-71, E-72, E-74, E-76, E-77, E-78, E-79, E-80, E-81, E-82, E-83, E-85, E-86, E-87, E-88, E-89, E-90, E-91, E-92, E-93, E-94, E-95.

*Sclerotinia sclerotiorum*/Liquid Culture (Cottony Rot)

Mycelia fragments of a newly grown liquid culture of the fungus are directly mixed into 5 nutrient broth (Vogels broth). After placing a (DMSO) solution of test compound into a microtiter plate (96-well format) the nutrient broth containing the fungal material is added. The test plates are incubated at 24° C. and the inhibition of growth is determined photometrically 3-4 days after application. The following compounds gave at least 80% control of *Sclerotinia sclerotiorum* at 20 ppm when compared to untreated control under the 10 same conditions, which showed extensive disease development:

E-50, E-51, E-52, E-55, E-57, E-64, E-65, E-66, E-67, E-69, E-70, E-71, E-72, E-79, E-80, E-81, E-82, E-83, E-86, E-87, E-88, E-89, E-91, E-93.

The invention claimed is:

1. A compound of formula (I):

(I)

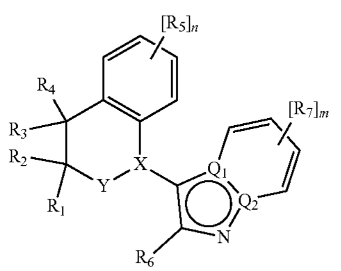

Wherein $Q_1$ is a carbon atom and $Q_2$ is a nitrogen atom;

Y—X represents:

G1

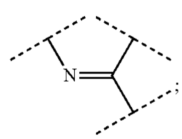

$R_1$ and $R_2$ are each independently selected from hydrogen, cyano, $C_1$-$C_6$ alkyl, $C_3$-$C_7$ cycloalkyl, $C_2$-$C_6$ alkenyl and $C_2$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio;

$R_3$ and $R_4$ are each independently selected from hydrogen, halogen, hydroxyl, $C_1$-$C_6$ alkyl, $C_1$-$C_6$ alkoxy, $C_3$-$C_7$ cycloalkyl, $C_2$-$C_6$ alkenyl and $C_2$-$C_6$ alkynyl, in which the alkyl, alkoxy, cycloalkyl, alkenyl and alkynyl groups may be optionally substituted with 1 to 3 substituents independently selected from halogen, $C_1$-$C_6$ alkoxy and $C_1$-$C_6$ alkylthio; or $R_3$ and $R_4$ together with the carbon atom to which they are attached represent C═O, C═NOR$_d$, or C═C($R_b$)($R_c$); where $R_b$ and $R_c$ are each independently selected from hydrogen, halogen, cyano, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy and $C_1$-$C_6$ alkylthio, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio, and where $R_d$ is selected from hydrogen, $C_1$-$C_6$ alkyl, $C_3$-$C_7$ cycloalkyl, $C_3$-$C_6$ alkenyl and $C_3$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio;

each $R_5$ independently represents halogen, hydroxyl, mercapto, nitro, cyano, formyl, $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(═NOR$_a$)$C_1$-$C_6$alkyl, $C_1$-$C_6$ alkylcarbonyl, aryl or phenoxy, in which the alkyl, cycloalkyl, alkenyl, alkynyl, alkoxy, alkenyloxy, alkynyloxy, and aryl groups may be optionally substituted with 1 to 5 substituents independently selected from halogen, $C_1$-$C_6$ alkyl, $C_1$-$C_6$ alkoxy, cyano and $C_1$-$C_6$ alkylthio; n is 0, 1, 2, 3 or 4;

$R_6$ is hydrogen, halogen, $C_1$-$C_6$ alkyl, $C_1$-$C_6$ alkoxy or hydroxyl;

each $R_7$ independently represents hydroxyl, mercapto, cyano, halogen, $C_1$-$C_6$ alkyl, $C_1$-$C_6$ haloalkyl, $C_2$-$C_6$ alkenyl, $C_2$-$C_6$ alkynyl, $C_2$-$C_6$ haloalkenyl, $C_3$-$C_6$ haloalkynyl, $C_1$-$C_6$ alkylthio, $C_1$-$C_6$ haloalkoxy, $C_1$-$C_6$ haloalkylthio, $C_1$-$C_6$ alkoxycarbonyl, $C_1$-$C_6$ alkylcarbonyl, $C_3$-$C_7$ cycloalkyl, $C_1$-$C_6$ alkoxy, $C_3$-$C_6$ alkenyloxy or $C_3$-$C_6$ alkynyloxy; m is 0, 1, 2, 3 or 4; and $R_a$ is $C_1$-$C_6$ alkylcarbonyl or $C_1$-$C_6$ alkyl, which may be optionally substituted with 1 to 3 substituents independently selected from the group consisting of halogen, $C_1$-$C_6$ alkoxy, $C_1$-$C_6$ alkylthio and phenoxy; or a salt or N-oxide thereof.

2. The compound according to claim 1 wherein $R_1$ and $R_2$ are each independently selected from hydrogen, $C_1$-$C_6$ alkyl, $C_3$-$C_7$ cycloalkyl, in which the alkyl and cycloalkyl groups may be optionally substituted with 1 to 3 substituents independently selected from halogen, $C_1$-$C_6$ alkoxy and $C_1$-$C_6$ alkylthio.

3. The compound according to claim 1 wherein:

$R_3$ and $R_4$ are each independently selected from hydrogen, halogen, hydroxyl, $C_1$-$C_6$ alkyl, $C_1$-$C_6$ alkoxy and $C_3$-$C_7$ cycloalkyl, in which the alkyl, alkoxy and cycloalkyl groups may be optionally substituted with 1 to 3 substituents independently selected from halogen, $C_1$-$C_6$ alkoxy and $C_1$-$C_6$ alkylthio; or $R_3$ and $R_4$ together with the carbon atom to which they are attached represent C═O, C═NOR$_d$, or C═C($R_b$)($R_c$), where $R_b$ and $R_c$ are each independently selected from hydrogen, halogen, cyano, $C_1$-$C_6$ alkyl, $C_3$-$C_7$ cycloalkyl, $C_2$-$C_6$ alkenyl, $C_2$-$C_6$ alkynyl, $C_1$-$C_6$ alkoxy and $C_1$-$C_6$ alkylthio, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio, and where $R_d$ is selected from hydrogen, $C_1$-$C_6$ alkyl, $C_3$-$C_7$ cycloalkyl, $C_3$-$C_6$ alkenyl and $C_3$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio.

4. The compound according to claim 1 wherein each $R_5$ independently represents halogen, cyano, $C_1$-$C_6$ alkyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(=NOR$_a$)$C_1$-$C_6$alkyl, phenyl or phenoxy in which the alkyl, cycloalkyl, alkenyl, alkynyl, alkoxy, alkenyloxy, alkynyloxy, and phenyl groups may be optionally substituted with 1 to 5 substituents independently selected from halogen, $C_1$-$C_6$ alkyl, $C_1$-$C_6$ alkoxy, cyano and $C_1$-$C_6$ alkylthio;

n is 0, 1, 2, 3 or 4.

5. The compound according to claim 1 wherein $R_6$ is hydrogen, halogen, or $C_1$-$C_2$ alkyl.

6. The compound according to claim 1 wherein each $R_7$ independently represents cyano, halogen, $C_1$-$C_6$ alkyl, $C_1$-$C_6$ haloalkyl, $C_2$-$C_6$ alkenyl, $C_2$-$C_6$ alkynyl, $C_2$-$C_6$ haloalkenyl, $C_3$-$C_6$ haloalkynyl, $C_1$-$C_6$ alkylthio, $C_1$-$C_6$ haloalkoxy, $C_1$-$C_6$ haloalkylthio, $C_3$-$C_7$ cycloalkyl, $C_1$-$C_6$ alkoxy, $C_3$-$C_6$ alkenyloxy or $C_3$-$C_6$ alkynyloxy; m is 0, 1, 2, 3 or 4.

7. The compound according to claim 1 wherein:

$R_1$ and $R_2$ are each independently a hydrogen or $C_1$-$C_4$ alkyl group, in which the alkyl group may be optionally substituted with 1 to 3 substituents independently selected from halogen, and $C_1$-$C_6$ alkoxy; or $R_3$ and $R_4$ are each independently selected from hydrogen, halogen, $C_1$-$C_4$ alkyl and $C_3$-$C_4$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio; or $R_3$ and $R_4$ together with the carbon atom to which they are attached represent C=O or C=NOR$_d$, where $R_d$ is selected from hydrogen, $C_1$-$C_4$ alkyl and $C_3$-$C_5$ cycloalkyl, in which the alkyl and cycloalkyl groups may be optionally substituted with 1 to 3 substituents independently selected from halogen, $C_1$-$C_3$ alkoxy and $C_1$-$C_3$ alkylthio;

each $R_5$ independently represents halogen, cyano, $C_1$-$C_4$ alkyl, $C_3$-$C_4$ cycloalkyl, $C_1$-$C_3$ alkoxy, $C_3$-$C_6$ alkenyloxy, $C_3$-$C_6$ alkynyloxy, phenyl, in which the alkyl, cycloalkyl, alkoxy, alkenyloxy, alkynyloxy, and phenyl groups may be optionally substituted with 1 to 3 substituents independently selected from halogen, $C_1$-$C_3$ alkyl and $C_1$-$C_3$ alkoxy;

n is 0, 1 or 2;

$R_6$ is hydrogen, fluoro, chloro, or methyl;

each $R_7$ independently represents cyano, halogen, $C_1$-$C_4$ alkyl, $C_1$-$C_4$ haloalkyl, $C_2$-$C_3$ alkynyl, $C_1$-$C_4$ alkylthio or $C_3$-$C_4$ cycloalkyl; and m is 0, 1 or 2; or a salt or N-oxide thereof.

8. The compound according to claim 1 wherein:

$R_1$ and $R_2$ are each independently a $C_1$-$C_3$ alkyl;

$R_3$ and $R_4$ are each independently selected from hydrogen, halogen and $C_1$-$C_4$ alkyl; or $R_3$ and $R_4$ together with the carbon atom to which they are attached represent C=O;

each $R_5$ independently represents halogen, cyano, $C_1$-$C_3$ alkyl, $C_3$-$C_3$ cycloalkyl;

n is 0, 1 or 2;

$R_6$ is hydrogen, fluoro, chloro, or methyl;

each $R_7$ independently represents cyano, halogen, $C_1$-$C_3$ alkyl, $C_1$-$C_3$ haloalkyl or $C_3$-$C_4$ cycloalkyl; and m is 0, 1 or 2; or a salt or N-oxide thereof.

9. The compound according to claim 1 wherein:

$R_1$ and $R_2$ are each independently a $C_1$-$C_2$ alkyl group;

$R_3$ and $R_4$ are each independently selected from hydrogen, fluoro and $C_1$-$C_2$ alkyl; or each $R_5$ independently represents fluoro, chloro, bromo, cyano, or $C_1$-$C_2$ alkyl;

n is 0, 1 or 2;

$R_6$ is hydrogen;

each $R_7$ independently represents fluoro, chloro or $C_1$-$C_3$ alkyl; and m is 1 or 2; or a salt or N-oxide thereof.

10. The compound according to claim 1 wherein the compound is a compound of formula (IK):

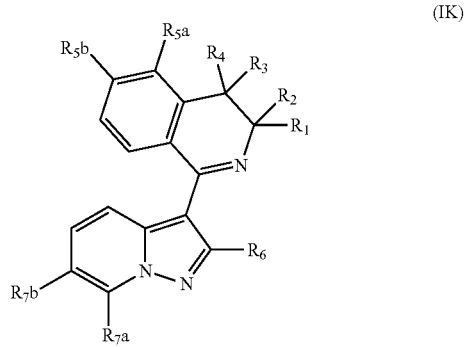

(IK)

wherein $R_1$ is methyl; $R_2$ is methyl; $R_3$ is methyl or fluoro; $R_4$ is methyl or fluoro; $R_5$a is fluoro or hydrogen; $R_5$b is fluoro or hydrogen; $R_6$ is hydrogen; $R_7$a is methyl or hydrogen;

and $R_7$b is methyl, fluoro or hydrogen;

or wherein $R_1$ is methyl, $R_2$ is methyl, $R_6$ is hydrogen and $R_3$, $R_4$, $R_5$a, $R_5$b, $R_7$a and $R_7$b are as defined below:

| Compound | $R_3$ | $R_4$ | $R_5$a | $R_5$b | $R_7$a | $R_7$b |
|---|---|---|---|---|---|---|
| IK-1 | methyl | methyl | fluoro | hydrogen | methyl | methyl |
| IK-2 | fluoro | fluoro | fluoro | hydrogen | methyl | methyl |
| IK-3 | fluoro | fluoro | hydrogen | fluoro | methyl | methyl |
| IK-4 | fluoro | fluoro | hydrogen | hydrogen | methyl | methyl |
| IK-5 | fluoro | fluoro | hydrogen | hydrogen | methyl | fluoro |
| IK-6 | fluoro | fluoro | hydrogen | hydrogen | methyl | hydrogen |
| IK-7 | fluoro | fluoro | hydrogen | hydrogen | hydrogen | methyl |
| IK-8 | methyl | methyl | fluoro | hydrogen | methyl | hydrogen |
| IK-9 | fluoro | fluoro | hydrogen | fluoro | methyl | hydrogen |
| IK-10 | fluoro | fluoro | hydrogen | fluoro | hydrogen | methyl | or a salt or N-oxide thereof.

11. The compound according to claim 1, wherein each $R_5$ independently represents halogen, hydroxyl, mercapto, nitro, cyano, formyl, $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_3$-$C_6$ alkenyloxy, $C_3$-$C_6$ alkynyloxy, $C_1$-$C_6$ alkylthio, —C(=NOR$_a$)C$_1$-C$_6$alkyl, and $C_1$-$C_6$ alkylcarbonyl.

12. The compound of claim 9, wherein:
$R_1$ and $R_2$ are both methyl;
$R_3$ and $R_4$ are methyl or fluoro;
n is 0 or 1;
each $R_5$ is fluoro; and
each $R_7$ is fluoro or methyl.

13. The compound of claim 1, wherein $R_1$ and $R_2$ are each independently selected from hydrogen, cyano, $C_1$-$C_6$ alkyl, $C_3$-$C_7$ cycloalkyl, $C_2$-$C_6$ alkenyl and $C_2$-$C_6$ alkynyl, in which the alkyl, cycloalkyl, alkenyl and alkynyl groups may be optionally substituted with 1 to 3 substituents independently selected from halogen, $C_1$-$C_6$ alkoxy and $C_1$-$C_6$ alkylthio; and $R_3$ and $R_4$ are each independently selected from hydrogen, halogen, hydroxyl, $C_1$-$C_6$ alkyl, $C_1$-$C_6$ alkoxy, $C_3$-$C_7$ cycloalkyl, $C_2$-$C_6$ alkenyl and $C_2$-$C_6$ alkynyl, in which the alkyl, alkoxy, cycloalkyl, alkenyl and alkynyl groups may be optionally substituted with 1 to 3 substituents independently selected from halogen, $C_1$-$C_6$ alkoxy and $C_1$-$C_6$ alkylthio.

\* \* \* \* \*